(12) United States Patent
Ignatyev et al.

(10) Patent No.: US 9,058,935 B2
(45) Date of Patent: Jun. 16, 2015

(54) COMPOUNDS CONTAINING ALKYL-CYANO-BORATE OR ALKYL-CYANO-FLUOROBORATE ANIONS

(75) Inventors: Nikolai (Mykola) Ignatyev, Duisburg (DE); Michael Schulte, Bischofsheim (DE); Kentaro Kawata, Kanagawa (JP); Tomohisa Goto, Kanagawa (JP); Jan Sprenger, Rommerskirchen (DE); Maik Finze, Kleinrinderfeld (DE); Walter Frank, Wuppertal (DE)

(73) Assignee: Merc Patent GmbH, Darmstadt (DE)

( * ) Notice: Subject to any disclaimer, the term of this patent is extended or adjusted under 35 U.S.C. 154(b) by 0 days.

(21) Appl. No.: 14/131,990

(22) PCT Filed: Jul. 6, 2012

(86) PCT No.: PCT/EP2012/002859
§ 371 (c)(1),
(2), (4) Date: Jan. 10, 2014

(87) PCT Pub. No.: WO2013/010641
PCT Pub. Date: Jan. 24, 2013

(65) Prior Publication Data
US 2014/0155566 A1    Jun. 5, 2014

(30) Foreign Application Priority Data
Jul. 15, 2011   (EP) ................................... 11005798

(51) Int. Cl.
| | |
|---|---|
| *C08F 16/12* | (2006.01) |
| *C08F 12/02* | (2006.01) |
| *C08F 10/00* | (2006.01) |
| *C07C 255/00* | (2006.01) |
| *C07D 233/00* | (2006.01) |
| *C07D 295/00* | (2006.01) |
| *C07D 305/00* | (2006.01) |
| *C07F 5/02* | (2006.01) |
| *H01G 9/20* | (2006.01) |
| *H01M 10/0525* | (2010.01) |
| *H01M 10/0568* | (2010.01) |
| *H01M 14/00* | (2006.01) |

(52) U.S. Cl.
CPC ............... *H01G 9/2013* (2013.01); *C07F 5/02* (2013.01); *H01M 10/0525* (2013.01); *H01M 10/0568* (2013.01); *H01M 14/005* (2013.01); *Y02E 60/122* (2013.01)

(58) Field of Classification Search
CPC ... C07F 5/02; H01M 10/0525; H01M 14/005; H01M 10/0568; H01G 9/2013; Y02E 60/122
USPC ........................ 526/332, 346, 348.7; 558/384; 548/335.1, 405; 549/213; 546/13
See application file for complete search history.

(56) References Cited

U.S. PATENT DOCUMENTS

| | | | |
|---|---|---|---|
| 4,307,182 A | | 12/1981 | Dalzell et al. |
| 4,647,440 A | * | 3/1987 | Blasius et al. ................. 423/181 |
| 7,645,434 B2 | | 1/2010 | Welz-Biermann et al. |
| 2006/0222584 A1 | * | 10/2006 | Welz-Biermann et al. ... 423/377 |

FOREIGN PATENT DOCUMENTS

WO    2005021661 A1    3/2005

OTHER PUBLICATIONS

International Search Report from PCT/EP2012/002859 dated Nov. 6, 2012.
Haijun Yao et al. "Organo-Tricyanoborates as Tectons: Illustrative Coordination Polymers Based on Copper(I) Derivatives" Inorganic Chemistry, [2005], vol. 44, No. 18, pp. 6256-6264.
Nagatoshi Koumura et al. "Alkyl-Functionalized Organic Dyes for Efficient Molecular Photovoltaics" J. Am. Chem. Soc., vol. 128, [2006], pp. 14256-14257.
H. Witte, et al. "Trialkylcyanoborates K[BR3CN]" J. Org. Chemistry, [1967], 2 pages.
Roland Koster et al. "Organosubstituierte cis-1,2-Diborylalkene als elektrophile Chelatbildner" Chem. Ber., vol. 126, [1993], pp. 305-317.
D. Gabel et al. "Organometallics" Science of Synthesis, vol. 6, [2004], pp. 541-560.

* cited by examiner

*Primary Examiner* — William Cheung
(74) *Attorney, Agent, or Firm* — Millen, White, Zelano, Branigan, P.C.

(57) ABSTRACT

The invention relates to new compounds containing alkyl/alkenyl-cyano-borate or alkyl/alkenyl-cyano-fluoroborate anions, their preparation and their use, in particular as part of electrolyte formulations for electrochemical or optoelectronic devices.

26 Claims, No Drawings

COMPOUNDS CONTAINING ALKYL-CYANO-BORATE OR ALKYL-CYANO-FLUOROBORATE ANIONS

This application is a U.S. National Stage Application of PCT Application No. PCT/EP2012/002859 filed Jul. 6, 2012, which claims priority on European Patent Application No. 11005798.1 filed Jul., 15 2011. Both of which are incorporated herein in their entirety.

The invention relates to new compounds containing alkyl/alkenyl-cyano-borate or alkyl/alkenyl-cyano-fluoroborate anions, their preparation and their use, in particular as part of electrolyte formulations for electrochemical or optoelectronic devices.

The salts according to the invention can on the one hand be used for the synthesis of ionic liquids, on the other hand the salts can be employed per se as ionic liquid.

Ionic liquids or liquid salts are ionic species which consist of an organic cation and a generally inorganic anion. They do not contain any neutral molecules and usually have melting points below 373 K.

The area of ionic liquids is currently the subject of intensive research since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227.

The properties of ionic liquids, for example melting point, thermal and electrochemical stability, viscosity, are strongly influenced by the nature of the anion.

E. Bernhardt et al, Z. Anorg. Allg. Chem. 2000, 626, 560, E. Bernhardt et al, Chem. Eur. J. 2001, 7, 4696 and E. Bernhardt et al, Z. Anorg. Allg. Chem. 2003, 629, 1229 disclose the novel chemically and electrochemically stable borate anions $[B(CN)_4]^-$, $[F_xB(CN)_{4-x}]^-$, where x=1 to 3, and $[B(CF_3)_4]^-$.

EP 1205480 A1 describes tetrakisfluoroalkylborate salts and the use thereof as conductive salts or ionic liquids.

WO 2005/021661 describes cationic dyes having alkylcyanofluoroborate anions in which the dye is selected from the group of the azine, xanthene, polymethine, styryl, azo, tetrazolium, pyrylium, benzopyrylium, thiopyrylium, benzothiopyrylium, thiazine, oxazine, triarylmethane, diarylmethane, acridine, quinoline, isoquinoline or quaternised azafluorenone dyes.

Roland Köster et al, Chem. Ber. 1993, 126, 305 describes the synthesis of solvated $K[(C_2H_5)_3BCN]$ through reaction of KCN with $B(C_2H_5)_3$ in toluene.

H. Witte et al, Z. für Naturforschung, 22b (1967), 1083 presents the preparation of $K[(Alk)_3BCN]$ and $[(CH_3)_4N][(Alk)_3BCN]$ through reaction of KCN with $B(Alk)_3$ in diethyl ether in which Alk denotes $CH_3$, $C_2H_5$, n-$C_3H_7$ and n-$C_4H_9$.

Haijun Yao et al, Inorganic Chemistry (2005), 44(18), 6256-6264 describes the synthesis of potassium(18-crone-6) [(n-$C_8H_{17}$)$_3$B(CN]-anion and tetraethylammonium [(phenyl)$_3$ B(CN)] for further application in coordination chemistry.

The object of the present invention was to provide alternative compounds which are novel, thermally and electrochemically stable which can be used for the synthesis of ionic liquids or as ionic liquids or as conductive salts, and which are in particular useful for the synthesis of ionic liquids or as ionic liquids or organic salts for application in electrochemical or optoelectronic devices. The object of the present invention was furthermore to provide a method for the preparation of the alternative salts, especially the compounds of formula I, as described below, which can be produced in economical way on industrial scale.

The object is achieved by the salts of the formula I according to the invention with alkyl-cyano-, alkenyl-cyano-, alkenyl-cyano-fluoro- or alkyl-cyano-fluoro-borate anions and the described methods for their preparation.

The invention therefore relates to compounds of formula I $$[Kt]^{z+}{}_z[(R^1)_{4-x-y-v}B(CN)_x(NC)_yF_v]^- \qquad I$$

in which $R^1$ each independently denotes a straight-chain or branched alkyl group having 1 to 20 C atoms, which optionally may contain at least one Cl, Br or I atom, at least one CN group and/or one or more oxygen or sulphur atoms, a straight-chain or branched alkenyl group having 2 to 20 C atoms having one or more double bonds, which optionally may contain at least one Cl, Br or I atom and/or one or more oxygen or sulphur atoms, a straight-chain or branched alkinyl group having 1 to 20 C atoms having one or more triple bonds, which optionally may contain at least one Cl, Br or I atom and/or one or more oxygen or sulphur atoms and optionally may have a double bond, or unsubstituted phenyl, z is 1, 2, 3 or 4, x is 1, 2 or 3, y is 0, 1 or 2, v is 0, 1 or 2 and the sum of x+y+v is 2 or 3 and in which $Kt^{z+}$ denotes an inorganic cation selected from the group of $NO^+$, $H^+$, $Li^+$, $Na^+$, $K^+$, $Rb^+$, $Cs^+$, or $Mg^{2+}$, $Cu^+$, $Cu^{2+}$, $Zn^{2+}$, $Ag^+$, $Ca^{2+}$, $Y^{+3}$, $Yb^{+3}$, $La^{+3}$, $Sc^{+3}$, $Ce^{+3}$, $Nd^{+3}$, $Tb^{+3}$, $Sm^{+3}$ or complex (ligands containing) metal cations which include rare-earths, transitions or noble metals like rhodium, ruthenium, iridium, palladium, platinum, osmium, cobalt, nickel, iron, chromium, molybdenum, tungsten, vanadium, titanium, zirconium, hafnium, thorium, uranium, gold, or an organic cation selected from the group of a tritylium cation, in which the phenyl groups may be substituted by straight-chain or branched alkyl groups having 1 to 20 C atoms, straight-chain or branched alkenyl having 2 to 20 C atoms and one or more double bonds or straight-chain or branched alkynyl having 2 to 20 C atoms and one or more triple bonds, an oxonium cation of formula (1) or a sulfonium cation of formula (2))

$$[(R^o)_3O]^+ \qquad (1)$$

$$[(R^o)_3S]^+ \qquad (2),$$

where $R^o$ each independently of one another denotes a straight-chain or branched alkyl group having 1-8 C atoms, non-substituted phenyl or phenyl which is substituted by $R^{1*}$, $OR'$, $N(R')_2$, CN or halogen and in case of sulfonium cations of formula (2) additionally denotes each independently $(R''')_2$ N and R' is independently of each other H, non-fluorinated, partially fluorinated or perfluorinated straight-chain or branched $C_1$- to $C_{18}$-alkyl, saturated $C_3$- to $C_7$-cycloalkyl, non-substituted or substituted phenyl, $R^{1*}$ is independently of each other non-fluorinated, partially fluorinated or perfluorinated straight-chain or branched $C_1$- to $C_{18}$-alkyl, saturated $C_3$- to $C_7$-cycloalkyl, non-substituted or substituted phenyl and R''' is independently of each other straight-chain or branched $C_1$ to $C_6$ alkyl;

an ammonium cation, which conforms to the formula (3)

$$[NR_4]^+ \tag{3}$$

where
R in each case, independently of one another, denotes
H, OR', N(R')$_2$, with the proviso that a maximum of one R in formula (3) is OR' or N(R')$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms, where one or two R may be fully substituted by halogens, in particular —F and/or —Cl, and one or more of the substituents R may be partially substituted by halogens, in particular —F and/or —Cl, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', —SO$_2$R' and where one or two non-adjacent carbon atoms in R which are not in the α-position may be replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(F)$_2$=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a phosphonium cation, which conforms to the formula (4)

$$[P(R^2)_4]^+ \tag{4}$$

where
$R^2$ in each case, independently of one another, denotes
H, OR' or N(R')$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two $R^2$ may be fully substituted by halogens, in particular —F and/or —Cl, and one or more of the substituents $R^2$ may be partially substituted by halogens, in particular —F and/or —Cl, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', —SO$_2$R' and where one or two non-adjacent carbon atoms in $R^2$ which are not in the α-position may be replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(F)$_2$=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a uronium cation, which conforms to the formula (5)

$$[C(NR^3R^4)(OR^5)(NR^6R^7)]^+ \tag{5}$$

where
$R^3$ to $R^7$ each, independently of one another, denote
H, where H is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms, where one or two of the substituents $R^3$ to $R^7$ may be fully substituted by halogens, in particular —F and/or —Cl, and one or more of the substituents $R^3$ to $R^7$ may be partially substituted by halogens, in particular —F and/or —Cl, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', —NO$_2$ and where one or two non-adjacent carbon atoms in $R^3$ to $R^7$ which are not in the α-position may be replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(F)$_2$=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a thiouronium cation, which conforms to the formula (6)

$$[C(NR^3R^4)(SR^5)(NR^6R^7)]^+ \tag{6}$$

where
$R^3$ to $R^7$ each, independently of one another, denote
H, where H is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms, where one or two of the substituents $R^3$ to $R^7$ may be fully substituted by halogens, in particular —F and/or —Cl, and one or more of the substituents $R^3$ to $R^7$ may be partially substituted by halogens, in particular —F and/or —Cl, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', —NO$_2$ and where one or two non-adjacent carbon atoms in $R^3$ to $R^7$ which are not in the α-position may be replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(F)$_2$=N— or —P(O)R'— where R' each independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl and X each independently is halogen;

a guanidinium cation, which conforms to the formula (7)

$$[C(NR^8R^9)(NR^{10}R^{11})(NR^{12}R^{13})]^+ \tag{7}$$

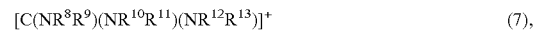

where
$R^8$ to $R^{13}$ each, independently of one another, denote
H, —CN, N(R')$_2$, —OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms, where one or two of the substituents $R^8$ to $R^{13}$ may be fully substituted by halogens, in particular —F and/or —Cl, and one or more of the substituents $R^8$ to $R^{13}$ may be partially substituted by halogens, in particular —F and/or —Cl, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', —NO$_2$ and where one or two non-adjacent carbon atoms in $R^8$ to $R^{13}$ which are not in the α-position may be replaced by atoms and/or atom groups selected from the group —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O) R'O—, —P(O)(N(R')$_2$)NR'—, —P(F)$_2$=N— or —P(O) R'—, where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl and X each independently is halogen;
a heterocyclic cation which conforms to the formula (8)

$$[HetN]^{z+} \quad (8)$$

where
HetN$^{z+}$ denotes a heterocyclic cation selected from the group

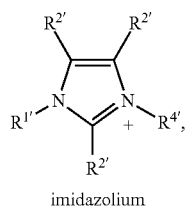

imidazolium

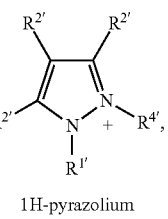

1H-pyrazolium

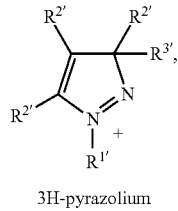

3H-pyrazolium

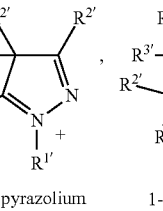

4H-pyrazolium 1-pyrazolinium

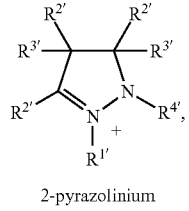

2-pyrazolinium

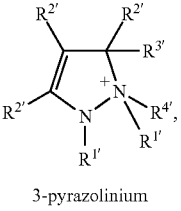

3-pyrazolinium

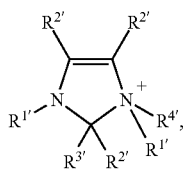

2,3-dihydroimidazolinium

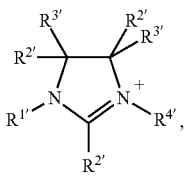

4,5-dihydroimidazolinium

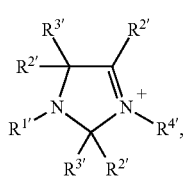

2,5-dihydroimidazolinium

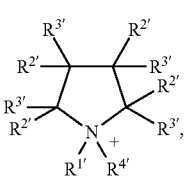

pyrrolidinium

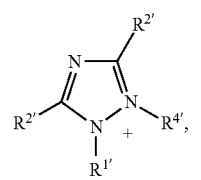

1,2,4-triazolium

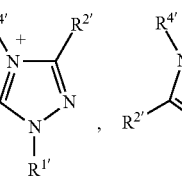

1,2,4-triazolium

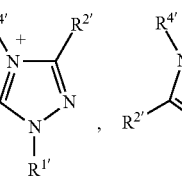

1,2,3-triazolium

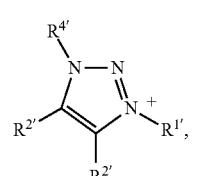

1,2,3-triazolium

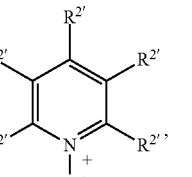

pyridinium

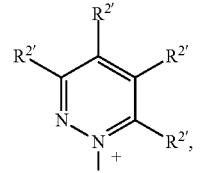

pyridazinium

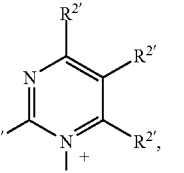

pyrimidinium

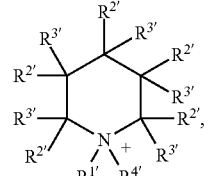

piperidinium

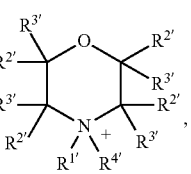

morpholinium

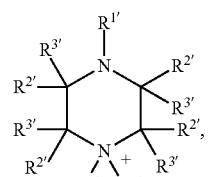

piperazinium

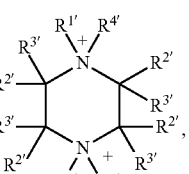

piperazinium

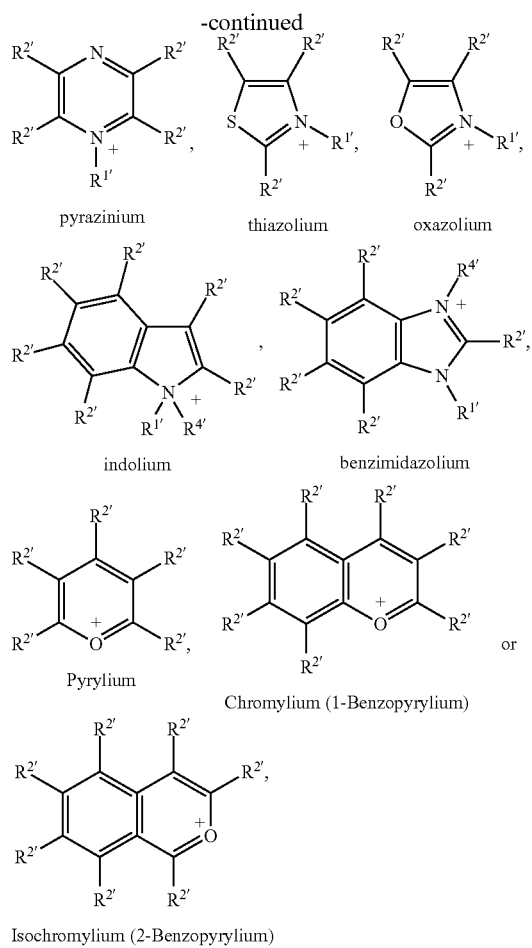

pyrazinium   thiazolium   oxazolium indolium   benzimidazolium

Pyrylium   Chromylium (1-Benzopyrylium)

Isochromylium (2-Benzopyrylium)

where the substituents
R¹' to R⁴' each, independently of one another, denote
H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
and
R²' denote additionally F, Cl, Br, I, —CN, —OR', —N(R')$_2$, —P(O)(R')$_2$, —P(O)(OR')$_2$, —P(O)(N(R')$_2$)$_2$, —C(O)R', —C(O)OR', —C(O)X, —C(O)N(R')$_2$, —SO$_2$N(F)$_2$, —SO$_2$OH, —SO$_2$X, —SR', —S(O)R', —SO$_2$R' and/or NO$_2$, with the proviso that R¹', R³', R⁴' are in this case independently of each other H and/or a straight-chain or branched alkyl having 1-20 C atoms, straight-chain or branched alkenyl having 2-20 C atoms and one or more double bonds,
where one to three substituents R¹' to R⁴' may be fully substituted by halogens, in particular —F and/or —Cl, and one or more substituents R¹' to R⁴' may be partially substituted by halogens, in particular —F and/or —Cl, and/or by —OH, —OR', N(R')$_2$, —CN, —C(O)OH, —C(O)OR', —C(O)R', —C(O)N(R')$_2$, —SO$_2$N(F)$_2$, —C(O)X, —SO$_2$OH, —SO$_2$X, —SR', —S(O)R', —SO$_2$R', —NO$_2$, but where R¹' and R⁴' cannot simultaneously be fully substituted by halogens and where, in the substituents R¹' to R⁴', one or two non-adjacent carbon atoms which are not bonded to the heteroatom may be replaced by atoms and/or atom groups selected from the —O—, —S—, —S(O)—, —SO$_2$—, —SO$_2$O—, —C(O)—, —C(O)O—, —N⁺(R')$_2$—, —P(O)R'O—, —C(O)NR'—, —SO$_2$NR'—, —OP(O)R'O—, —P(O)(N(R')$_2$)NR'—, —P(F)$_2$=N— or —P(O)R'—, where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl and X each independently is halogen or a iodonium cation which conforms to the formula (9)

where
the aryl group Ar denotes each independently of each other aryl with 6 to 30 C atoms which is non-substituted or substituted with at least a straight-chain or branched alkyl group having 1 to 20 C atoms, a straight-chain or branched alkenyl group having 2 to 20 C atoms and one or more double bonds, a straight-chain or branched alkynyl group having 2 to 20 C atoms and one or more triple bonds, R¹*, NO$_2$, SR', N(R')$_2$, CN and/or halogen and
where R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl and
where R¹* each independently is non-fluorinated, partially fluorinated or perfluorinated straight-chain or branched C$_1$- to C$_{18}$-alkyl, saturated C$_3$- to C$_7$-cycloalkyl, non-substituted or substituted phenyl
and halogen is F, Cl, Br or I,
with the proviso that potassium(18-crone-6)tricyano-n-octylborate and tetraethylammonium phenyl-tricyanoborate are excluded.

Halogen is preferably F, Cl or Br, particularly preferably F or Cl.

R¹ preferably each independently denotes a straight-chain or branched alkyl group having 1 to 4 C atoms, which optionally may contain at least one Br atom or at least one CN group or at least one oxygen atom or a straight-chain or branched alkenyl having 2 to 4 C atoms. R¹ is particularly preferably each independently methyl, ethyl, n-butyl, bromomethyl, cyanomethyl, methoxymethyl, ethoxymethyl, vinyl or allyl. R¹ is very particularly preferably each independently methyl, ethyl, n-butyl, vinyl or allyl or very particularly preferably methyl, ethyl, vinyl or allyl or very particularly preferably methyl, ethyl or vinyl.

Particularly preferred compounds are compounds of formula IA, in which v is 1, y is 0 and x is 2

in which [Kt]$^{z+}$, z and R¹ has a meaning as defined above; formula IB, in which v is 0, y is 0 and x is 3

in which [Kt]$^{z+}$, z and R¹ has a meaning as defined above; formula IC, in which v is 0, y is 1 and x is 2

in which [Kt]$^{z+}$, z and R¹ has a meaning as defined above; formula ID, in which v is 2, y is 0 and x is 1

in which [Kt]$^{z+}$, z and R¹ has a meaning as defined above or formula IE, in which v is 0, y is 0 and x is 2

in which [Kt]$^{z+}$, z and R$^1$ has a meaning as defined above.

R$^1$ in a compound of formula IA preferably denotes an alkyl group having 1 to 4 C atoms which optionally may contain at least one Br atom or at least one CN group or at least one oxygen atom, particularly preferably methyl, ethyl, n-butyl, bromomethyl, cyanomethyl, methoxymethyl or ethoxymethyl, very particularly preferably methyl.

In another embodiment, R$^1$ in compound of formula IA preferably denotes an alkenyl group having 2 to 4 C atoms, particularly preferably vinyl or allyl.

R$^1$ in a compound of formula IB preferably denotes an alkyl group having 1 to 4 C atoms which optionally may contain at least one Br atom or at least one CN group or at least one oxygen atom or an alkenyl group having 2 to 4 C atoms, particularly preferably methyl, ethyl, n-butyl, bromomethyl, cyanomethyl, methoxymethyl, ethoxymethyl, vinyl or allyl, very particularly preferably methyl, ethyl or allyl or very particularly preferably methyl or allyl.

R$^1$ in a compound of formula IC preferably denotes an alkyl group having 1 to 4 C atoms or an alkenyl group having 2 to 4 C atoms, particularly preferably methyl, ethyl, n-butyl, vinyl or allyl, very particularly preferably methyl, n-butyl or vinyl or very particularly preferably methyl, ethyl, vinyl or allyl.

R$^1$ in a compound of formula ID preferably denotes an alkyl group having 1 to 4 C atoms which optionally may contain at least one Br atom or at least one CN group or at least one oxygen atom, particularly preferably methyl, ethyl, n-butyl, bromomethyl, cyanomethyl, methoxymethyl or ethoxymethyl, very particularly preferably methyl or ethyl or very particularly preferably methyl.

R$^1$ in a compound of formula IE preferably denotes an alkyl group having 1 to 4 C atoms which optionally may contain at least one Br atom or at least one CN group or at least one oxygen atom, particularly preferably methyl, ethyl, n-butyl, bromomethyl, cyanomethyl, methoxymethyl or ethoxymethyl, very particularly preferably methyl and ethyl or methyl or ethyl.

In another embodiment, R$^1$ in compound of formula IE preferably denotes an alkenyl group having 2 to 4 C atoms, particularly preferably vinyl or allyl.

Preferred anions according to the invention are methyltricyanoborate, ethyltricyanoborate, allyltricyanoborate, methylethyldicyanoborate, dimethyldicyanoborate and diethyldicyanoborate.

The compounds of formula I, preferably the compounds of formula IA to IE having organic cations are possessing good thermal and electrochemical stabilities and are of interest for practical applications, for example in dye or quantum dot sensitized solar cells (DSSCs). Some compounds of formula IA to IE having organic cations are even less viscous compared to the corresponding tetracyanoborates having the same organic cation. For example, 1-ethyl-3-methyl-imidazolium tetracyanoborate (emim TCB) has the dynamic viscosity of 22 mPas (at 20° C.) and the corresponding 1-ethyl-3-methyl-imidazolium methyl-tricyano-borate has a viscosity of 21.1 mPas (at 20° C.). The positive influence of the replacement of one cyano-group with an alkyl group on the viscosity of compounds of formula I having organic cations compared to the compounds with tetracyanoborate anions having the same organic cation is unexpected. In comparison to electron-withdrawing groups like fluor, perfluoroalkyl or cyano groups which are able to effectively delocalise the negative charge of borate anions, an alkyl group practically does not participate in the stabilization of the borate-anion. The introduction of one alkyl group to Boron should increase the coordination ability of the alkyl-tricyano borate anion, causing increase in the viscosity of ionic liquids with this anion. But the experimental results are totally opposite from the theoretical point of view.

Not being bound by that theory, it seems that the introduction of one alkyl group to Boron breaks the symmetry of tetracyano-borate anion resulting in decreasing of ionic liquids viscosity.

Another advantage of compounds of formula I is that they can be prepared from commercially available starting materials via a simple reaction protocol.

Preferred inorganic cations [Kt]$^{z+}$ are metal cations, such as Li$^+$, Na$^+$, K$^+$, Rb$^+$, Cs$^+$, or Mg$^{2+}$, Cu$^{2+}$, Cu$^{2+}$, Zn$^{2+}$, Ag$^+$, Ca$^{2+}$, wherein copper-tricyano-n-octylborate is excluded from the protection as a compound and z is 1 or 2. The alkali metal is preferably lithium which is preferably used as conducting salt and/or component of electrolytes for application in batteries, capacitors, sensors or for electrochemical processes, and sodium or potassium which is preferably used for the synthesis of compounds of formula I as described above and below in which the cation [Kt]$^{z+}$ is a cation other than the used sodium or the used potassium, especially preferably for compounds of formula I in which the cation [Kt]$^{z+}$ is an organic cation.

If [Kt]$^{z+}$ is an organic cation, the organic cation is preferably selected from the group comprising iodonium, tritylium, sulfonium, oxonium, ammonium, phosphonium, uronium, thiouronium, guanidinium cations or heterocyclic cations.

Examples of organic cations are also polyammonium ions having a degree of charging of 4 which means z denotes 4.

For organic cations, the following apply:

R$^o$ of the [(R$^o$)$_3$O]$^+$ cation (formula (1)) is preferably straight-chain alkyl having 1-8 C atoms, preferably having 1-4 C atoms, in particular methyl or ethyl, very particularly preferably ethyl.

R$^o$ of the [(R$^o$)$_3$S]$^+$ cation (formula (2)) is preferably straight-chain alkyl having 1-8 C atoms, preferably having 1-4 C atoms, in particular methyl or ethyl, very particularly preferably ethyl. This definition is preferably for the technical application as component of an electrolyte, e.g. for DSSC. Preferred cations for this application are diethyl-methylsulfonium and triethylsulfonium.

At least one substitutent R$^0$ within the sulfonium cations of formula (2) is preferably phenyl or substituted phenyl in case the sulfonium cation is chosen together with the inventive anion as cationic polymerization initiator, photo-polymerization initiator or photo-acid generator. Particularly preferably all substituents R$^0$ in formula (2) are for this application each independently phenyl and/or phenyl substituted with SR' where R' has a meaning as described before.

Preferred cations of formula (2) for this application are triphenylsulfonium, diphenyltolylsulfonium, diphenylethylsulfonium, diphenyl-2,2,2-trifluorethyl sulfonium, diphenyl-2-ethoxy-ethylsulfonium, diphenyl-2-chlorethylsulfonium, diphenyl-3-brompropylsulfonium, diphenyl-3-chlorpropylsulfonium, diphenyl-3-cyanopropylsulfonium, diphenylallylsulfonium, diphenyl-4-pentenylsulfonium, diphenylpropargylsulfonium, diphenylbenzylsulfonium, diphenyl(p-cyanobenzyl)sulfonium, diphenyl(p-methylbenzyl)sulfonium, diphenyl(p-phenylthiobenzyl)sulfonium, diphenyl(3,3-dicyano-2-phenyl-2-propenyl)sulfonium, diphenyl(p-methylphenacyl)sulfonium, diphenyl(ethylcarboxy)methylsulfonium, diphenyl(n-octyl)sulfonium, diphenyl(n-octadecyl)sulfonium, diphenyl(w-carboxytridecyl)sulfonium, diphenyl(3-oxypropyl)sulfonium, diphenyl(w-carboxydodecyl)sulfonium, dihexyl-phenylsulfonium, ditolylphenylsulfonium, tritolylsulfonium, m- or p-(tert-butyl)phenyl-diphenylsulfonium, m- or p-methoxyphenyldiphenylsulfonium, m- or p-CN-phenyl-diphenylsulfonium, m- or p-$C_6H_{13}$S-phenyl-diphenylsulfonium, m- or p-$C_6H_5$S-phenyl-diphenylsulfonium, Tri(p-methoxyphenyl)sulfonium, tri[4-(4-acetyl-phenylsulfanyl)phenyl]sulfonium, tri(4-tert.-butylphenyl)sulfonium.

For the purposes of the present invention, fully unsaturated cycloalkyl substituents are also taken to mean aromatic substituents.

In accordance with the invention, suitable substituents R and $R^2$ to $R^{13}$ of the compounds of the formulae (3) to (7) are preferably: H, $C_1$- to $C_{20}$-, in particular $C_1$- to $C_{14}$-alkyl groups, and saturated or unsaturated, i.e. also aromatic $C_3$- to $C_7$-cycloalkyl groups, which may be substituted by $C_1$- to $C_6$-alkyl groups, in particular phenyl which may be substituted by $C_1$- to $C_6$-alkyl groups.

The substituents R and $R^2$ in the compounds of the formula (3) or (4) may be identical or different. The substituents R and $R^2$ are preferably different.

The substituents R and $R^2$ are particularly preferably methyl, ethyl, iso-propyl, propyl, n-butyl, sec-butyl, pentyl, hexyl, octyl, decyl or tetradecyl.

Up to four substituents of the guanidinium cation $[C(NR^8R^9)(NR^{13}R^{11})(NR^{12}R^{13})]^+$ may also be bonded in pairs in such a way that mono-, bi- or polycyclic cations are formed.

Without restricting generality, examples of such guanidinium cations are:

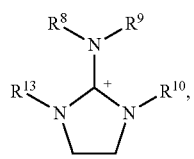
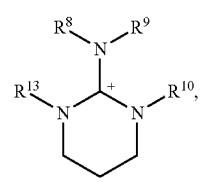
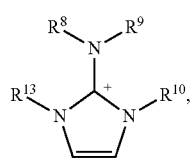
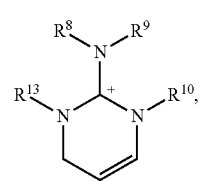
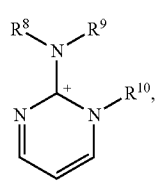
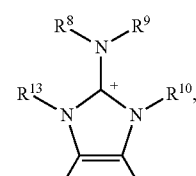
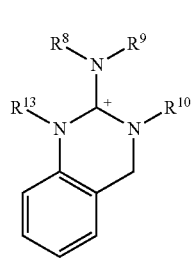
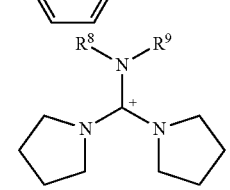

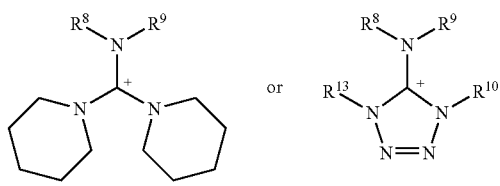

where the substituents $R^8$ to $R^{10}$ and $R^{13}$ can have a meaning or particularly preferred meaning indicated above.

If desired, the carbocycles or heterocycles of the guanidinium cations indicated above may also be substituted by straight-chain or branched $C_1$- to $C_6$-alkyl, straight-chain or branched $C_1$- to $C_6$-alkenyl, —CN, —$NO_2$, F, Cl, Br, I, OH, straight-chain or branched $C_1$-$C_6$-alkoxy, —N(R')$_2$, —SR', —S(O)R', —$SO_2$R', —COOH, —C(O)OR', —C(O)R', —C(O)N(R')$_2$, —$SO_2$N(R')$_2$, —C(O)X, —$SO_2$X, —$SO_3$H, substituted or non-substituted phenyl or a non-substituted or substituted heterocycle, where X and R' have a meaning indicated above.

Up to four substituents of the uronium cation $[C(NR^3R^4)(OR^8)(NR^8R^7)]^+$ or thiouronium cation $[C(NR^3R^4)(SR^8)(NR^8R^7)]^+$ may also be bonded in pairs in such a way that mono-, bi- or polycyclic cations are formed.

Without restricting generality, examples of such cations are indicated below, where Y=O or S:

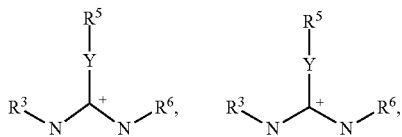
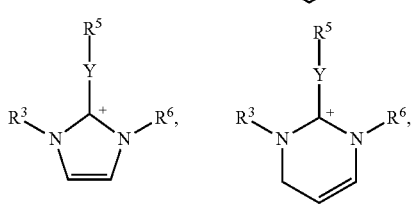
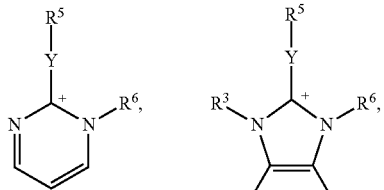
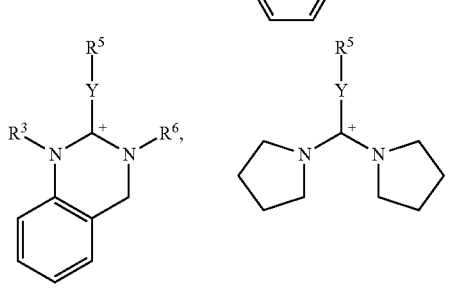

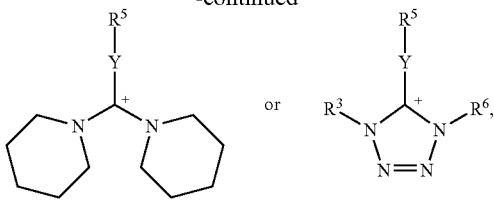

where the substituents $R^3$, $R^5$ and $R^6$ can have a meaning or particularly preferred meaning indicated above.

If desired, the carbocycles or heterocycles of the cations indicated above may also be substituted by straight-chain or branched $C_1$- to $C_6$-alkyl, straight-chain or branched $C_1$- to $C_6$-alkenyl, —CN, —$NO_2$, F, Cl, Br, I, OH, straight-chain or branched $C_1$-$C_6$-alkoxy, —N(R')$_2$, —SR', —S(O)R', —SO$_2$R', —COOH, —C(O)OR', —C(O)R', —C(O)N(R')$_2$, —SO$_2$N(R')$_2$, —C(O)X, —SO$_2$X, —SO$_3$H, substituted or non-substituted phenyl or a non-substituted or substituted heterocycle, where X and R' have a meaning indicated above.

The substituents $R^3$ to $R^{13}$ are each, independently of one another, preferably a straight-chain or branched alkyl group having 1 to 16 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formula (5) to (7) may be identical or different. $R^3$ to $R^{13}$ are particularly preferably each, independently of one another, methyl, ethyl, n-propyl, iso-propyl, n-butyl, tert-butyl, sec-butyl, phenyl, hexyl or cyclohexyl, very particularly preferably methyl, ethyl, n-propyl, iso-propyl, n-butyl or hexyl.

In accordance with the invention, suitable substituents $R^{1'}$ to $R^{4'}$ of compounds of the formula (8) are each, independently of one another, preferably,
H,
straight-chain or branched alkyl having 1 to 20 C atoms, which optionally may be fluorinated or perfluorinated,
straight-chain or branched alkenyl having 2 to 20 C atoms and one or more double bonds, which optionally may be fluorinated,
straight-chain or branched alkynyl having 2 to 20 C atoms and one or more triple bonds which optionally may be fluorinated or
straight-chain or branched alkoxyalkyl having 2 to 8 C atoms, with the assumption that $R^{1'}$ and $R^{4'}$ are not simultaneously be perfluorinated.

The substituents $R^{1'}$ and $R^{4'}$ are each, independently of one another, particularly preferably straight-chain or branched alkyl having 1 to 20 C atoms, which optionally may be fluorinated or perfluorinated or straight-chain or branched alkoxyalkyl having 2 to 8 C atoms with the assumption that $R^{1'}$ and $R^{4'}$ are not perfluorinated at the same time.

The substituents $R^{1'}$ and $R^{4'}$ are each, independently of one another, particularly preferably methyl, ethyl, allyl, iso-propyl, propyl, n-butyl, sec-butyl, tert-butyl, n-pentyl, n-hexyl, n-octyl, n-decyl, cyclohexyl, methoxyethyl, methoxymethyl, ethoxyethyl or ethoxymethyl. They are very particularly preferably methyl, ethyl, propyl, n-butyl or methoxyethyl. In pyrrolidinium, piperidinium or indolinium compounds, the two substituents $R^{1'}$ and $R^{4'}$ are preferably different.

In accordance with the invention, suitable substituents $R^{2'}$ and $R^{3'}$ of compounds of formula (8) are particularly preferably: H, straight-chain or branched $C_1$- to $C_{20}$-, in particular $C_1$- to $C_{12}$-alkyl groups.

The substituent $R^{2'}$ or $R^{3'}$ is in each case, independently of one another, in particular H, methyl, ethyl, iso-propyl, propyl, n-butyl, sec-butyl or tert-butyl. $R^{2'}$ is particularly preferably H, methyl, ethyl, iso-propyl, propyl, n-butyl or sec-butyl. $R^{3'}$ is particularly preferably H. $R^{2'}$ and $R^{3'}$ are very particularly preferably H.

A straight-chain or branched alkyl having 1-20 C atoms denotes an alkyl group having 1, 2, 3, 4, 5, 6, 7, 8, 9, 10, 11, 12, 13, 14, 15, 16, 17, 18, 19 or 20 C atoms, for example methyl, ethyl, iso-propyl, n-propyl, iso-butyl, n-butyl, tert-butyl, n-pentyl, 1-, 2- or 3-methylbutyl, 1,1-, 1,2- or 2,2-dimethylpropyl, 1-ethylpropyl, n-hexyl, n-heptyl, n-octyl, ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or eicosyl, which optionally may be fluorinated or perfluorinated. The term "perfluorinated" means that all H atoms are substituted by F atoms in the given alkyl group. The term "fluorinated" means that at least one H atom of the given alkyl group is substituted by an F atom.

A straight-chain or branched alkenyl having 2 to 20 C atoms, in which a plurality of double bonds may also be present, is, for example, allyl, 2- or 3-butenyl, iso-butenyl, sec-butenyl, furthermore 4-pentenyl, iso-pentenyl, hexenyl, heptenyl, octenyl, —$C_9H_{17}$, —$C_{10}H_{19}$ to —$C_{20}H_{39}$, preferably allyl, 2- or 3-butenyl, iso-butenyl, sec-butenyl, furthermore preferably 4-pentenyl, isopentenyl or hexenyl, which may be optionally partially fluorinated.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl, which may be optionally partially fluorinated.

A straight-chain or branched alkoxyalkyl having 2 to 12 C atoms is, for example, methoxymethyl, 1-methoxyethyl, 1-methoxypropyl, 1-methoxy-2-methyl-ethyl, 2-methoxypropyl, 2-methoxy-2-methyl-propyl, 1-methoxybutyl, 1-methoxy-2,2-dimethyl-ethyl, 1-methoxy-pentyl, 1-methoxyhexyl, 1-methoxy-heptyl, ethoxymethyl, 1-ethoxyethyl, 1-ethoxypropyl, 1-ethoxy-2-methyl-ethyl, 1-ethoxybutyl, 1-ethoxy-2,2-dimethyl-ethyl, 1-ethoxypentyl, 1-ethoxyhexyl, 1-ethoxyheptyl, propoxymethyl, 1-propoxyethyl, 1-propoxypropyl, 1-propoxy-2-methyl-ethyl, 1-propoxybutyl, 1-propoxy-2,2-dimethyl-ethyl, 1-propoxypentyl, butoxymethyl, 1-butoxyethyl, 1-butoxypropyl or 1-butoxybutyl. Particularly preferred is methoxymethyl, 1-methoxyethyl, 2-methoxy-propyl, 1-methoxypropyl, 2-methoxy-2-methyl-propyl or 1-methoxybutyl. The numeration begins from the last carbon in the alkyl chain.

Aryl with 6 to 30 C atoms denotes an aryl group with 6 to 30 C atoms and is an aromatic group with aromatic delocalized electrons, optionally substituted one or more times by $R^{1*}$, OR', N(R')$_2$, CN, $NO_2$ or halogen. An aryl group with 6 to 30 C atoms, preferably with 6 to 24 C atoms, is for example 1-, 2-, 3-, 4-, 5- or 6-phenyl, 1-, 2-, 3-, 4-, 6-, 7- or 8-naphthyl, 1-, 2-, 3-, 4-, 6-, 7- or 8-phenanthrenyl, 1-, 2-, 3-, 4-, 5-, 6-, 7-, 8-, 9- or 10-anthracenyl, 1-, 2-, 3-, 4-, 5-, 6-, 7-, 8-, 9-, 10-, 11- or 12-tetracenyl, 1-, 2-, 3-, 4-, 5-, 6-, 7-, 8-, 9-, 10-, 11- or 12-benzo[a]anthracenyl, 1-, 2-, 3-, 4-, 5-, 6-, 7-, 8-, 9-, 10-, 11-, 12-, 13- or 15-pentacenyl, 1-, 2-, 3-, 4-, 5-, 6-, 7-, 8-, 9-, 10-, 11- or 12-chrysenyl, 1-, 2-, 3-, 4-, 5-, 6-, 7-, 8-, 9- or 10-pyrenyl, 1-, 2-, 3-, 4-, 5-, 6-, 7-, 8-, 9-, 10-, 11- or 12-benzo[a]pyrenyl, 1-, 2-, 3-, 4-, 5-, 6-, 7- or 8-azulenyl, 1-, 2-, 3-, 4-, 5-, 6-, 7-, 8-, 9- or 10-fluoranthenyl, 1-, 2-, 3-, 4-, 5-, 6-, 7-, 8-, 9-, 10-, 11- or 12-perylenyl, 1-, 2-, 3-, 4-, 5-, 6- or 7-indenyl or 1-, 2-, 3-, 4-, 5-, 6-, 7-, 8- or 9-fluorenyl which is preferably non-substituted or substituted by $R^{1*}$, OR', N(R')$_2$, CN or halogen. Preferably, aryl denotes 1-, 2-, 3-, 4-, 5- or 6-phenyl and 1-, 2-, 3-, 4-, 6-, 7- or 8-naphthyl which are non-substituted or substituted by $R^{1*}$, OR', $N(R')_2$, CN or halogen. $R^{1*}$ and R' have a meaning as described above.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OH, —OR', —$N(R')_2$, —CN, —C(O)OH, —C(O)N(R')$_2$, —SO$_2$N(R')$_2$, —C(O)X, —C(O)OR', —C(O)R', —SO$_2$OH, —SO$_2$X, —SR', —S(O)R', —SO$_2$R', —NO$_2$ and R' and X have a meaning as described above.

Non-substituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by straight-chain or branched $C_1$- to $C_6$-alkyl groups, where the cycloalkyl group or the cycloalkyl group substituted by straight-chain or branched $C_1$- to $C_6$-alkyl groups may in turn also be substituted by halogen atoms, such as F, Cl, Br or I, in particular F or Cl, or by —OH, —OR', —N(R')$_2$, —CN, —C(O)OH, —C(O)N(R')$_2$, —SO$_2$N(R')$_2$, —C(O)X, —C(O)OR', —C(O)R', —SO$_2$OH, —SO$_2$X, —SR', —S(O)R', —SO$_2$R', —NO$_2$ and R' and X have a meaning as described above.

In the substituents R, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—, where R' is non-fluorinated, partially fluorinated or perfluorinated $C_1$- to $C_{18}$-alkyl, saturated $C_3$- to $C_7$-cycloalkyl, non-substituted or substituted phenyl.

Without restricting generality, examples of substituents R, $R^2$ to $R^{13}$ and $R^{1'}$ to $R^{4'}$ modified in this way are:
—OCH$_3$, —OCH(CH$_3$)$_2$, —CH$_2$OCH$_3$, —CH$_2$—CH$_2$—O—CH$_3$, —C$_2$H$_4$OCH(CH$_3$)$_2$, —C$_2$H$_4$C$_2$H$_5$, —C$_2$H$_4$SCH(CH$_3$)$_2$, —S(O)CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —O—C$_4$H$_8$—O—C$_4$H$_9$, —CF$_3$, —C$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_5$)C$_2$F$_5$, —CHF$_2$, —CH$_2$CF$_3$, —C$_2$F$_2$H$_3$, —C$_3$H$_6$, —CH$_2$C$_3$F$_7$, —C(CFH$_2$)$_3$, —CH$_2$C(O)OH, —CH$_2$C$_6$H$_5$, —C(O)C$_6$H$_5$ or P(O)(C$_2$H$_5$)$_2$.

In R' or in $R^{1*}$, $C_3$- to $C_7$-cycloalkyl is, for example, cyclopropyl, cyclobutyl, cyclopentyl, cyclohexyl or cycloheptyl.

In R' or in $R^{1*}$, substituted phenyl denotes phenyl which is substituted by straight-chain or branched $C_1$- to $C_6$-alkyl, straight-chain or branched $C_1$- to $C_6$-alkenyl, —CN, —NO$_2$, F, Cl, Br, I, —OH, straight-chain or branched-$C_1$-$C_6$-alkoxy, N(R")$_2$, —COOH, —C(O)OR", —C(O)R", —SO$_2$X', —SR", —S(O)R", —SO$_2$R", SO$_2$N(R")$_2$ or SO$_3$H, where X' denotes F, Cl or Br and R" denotes a non-fluorinated, partially fluorinated or perfluorinated straight-chain or branched $C_1$- to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

HetN$^{z+}$ is preferably

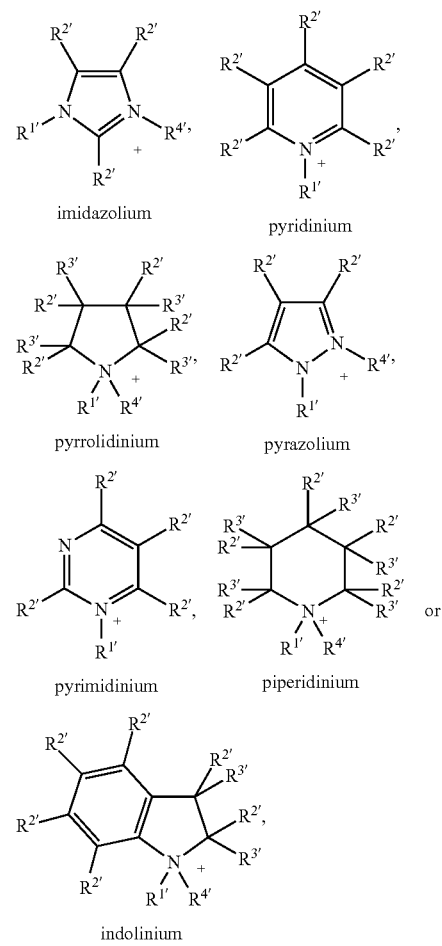

where the substituents $R^{1'}$ to $R^{4'}$ each, independently of one another, have a meaning described above.

HetN$^{z+}$ is particularly preferably

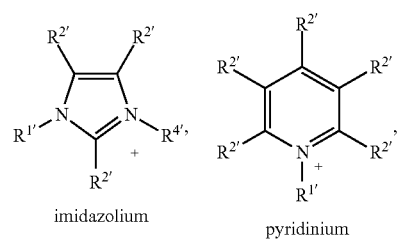

-continued

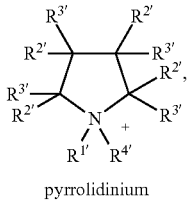
pyrrolidinium where the substituents $R^{1'}$ to $R^{4'}$ each, independently of one another, have a meaning described above.

$HetN^{z+}$ is very particularly preferably

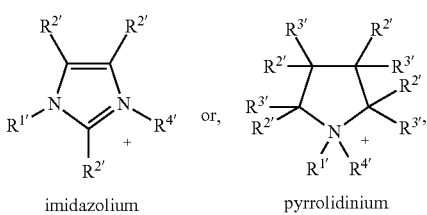
imidazolium     pyrrolidinium where the substituents $R^{1'}$ to $R^{4'}$ each, independently of one another, have a meaning described above. Preferred meanings of $R^{1'}$ to $R^{4'}$ within imidazolium or pyrrolidinium cations are defined in the following terms:

Preferred 1,1-dialkylpyrrolidinium cations are, for example, 1,1-dimethylpyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonylpyrrolidinium, 1-methyl-1-decylpyrrolidinium, 1,1-diethylpyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methylpyrrolidinium, 1-propyl-1-butylpyrrolidinium, 1-propyl-1-pentylpyrrolidinium, 1-propyl-1-hexylpyrrolidinium, 1-propyl-1-heptylpyrrolidinium, 1-propyl-1-octylpyrrolidinium, 1-propyl-1-nonylpyrrolidinium, 1-propyl-1-decylpyrrolidinium, 1,1-dibutylpyrrolidinium, 1-butyl-1-methylpyrrolidinium, 1-butyl-1-pentylpyrrolidinium, 1-butyl-1-hexylpyrrolidinium, 1-butyl-1-heptylpyrrolidinium, 1-butyl-1-octylpyrrolidinium, 1-butyl-1-nonylpyrrolidinium, 1-butyl-1-decylpyrrolidinium, 1,1-dipentylpyrrolidinium, 1-pentyl-1-hexylpyrrolidinium, 1-pentyl-1-heptylpyrrolidinium, 1-pentyl-1-octylpyrrolidinium, 1-pentyl-1-nonylpyrrolidinium, 1-pentyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-diheptylpyrrolidinium, 1-heptyl-1-octylpyrrolidinium, 1-heptyl-1-nonylpyrrolidinium, 1-heptyl-1-decylpyrrolidinium, 1,1-dioctylpyrrolidinium, 1-octyl-1-nonylpyrrolidinium, 1-octyl-1-decylpyrrolidinium, 1,1-dinonylpyrrolidinium, 1-nonyl-1-decylpyrrolidinium or 1,1-didecylpyrrolidinium. Very particular preference is given to 1-butyl-1-methylpyrrolidinium or 1-propyl-1-methylpyrrolidinium.

Preferred 1-alkyl-1-alkoxyalkylpyrrolidinium cations are, for example, 1-methoxymethyl-1-methyl-pyrrolidinium, 1-methoxymethyl-1-ethylpyrrolidinium, 1-(2-methoxyethyl)-1-methylpyrrolidinium, 1-(2-methoxyethyl)-1-ethylpyrrolidinium, 1-(2-methoxyethyl)-1-propylpyrrolidinium, 1-(2-methoxyethyl)-1-butylpyrrolidinium, 1-(2-ethoxyethyl)-1-methylpyrrolidinium, 1-ethoxymethyl-1-methylpyrrolidinium, 1-ethoxymethyl-1-ethylpyrrolidinium. Very particular preference is given to 1-(2-methoxyethyl)-1-methylpyrrolidinium.

Preferred 1,3-dialkylimidazolium cations are, for example, 1-ethyl-3-methylimidazolium, 1-methyl-3-propylimidazolium, 1,2,3-trimethylimidazolium, 1-ethyl-2,3-dimethylimidazolium, 1-propyl-2,3-dimethylimidazolium, 1-butyl-2,3-dimethylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentylimidazolium, 1-butyl-3-propylimidazolium, 1,3-dimethylimidazolium, 1,3-diethylimidazolium, 1,3-dipropylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexylimidazolium, 1-ethyl-3-heptylimidazolium, 1-ethyl-3-octylimidazolium, 1-ethyl-3-nonylimidazolium or 1-decyl-3-ethylimidazolium. Particularly preferred cations are 1-ethyl-3-methylimidazolium, 1-butyl-3-methylimidazolium or 1-methyl-3-propylimidazolium.

Preferred 1-alkoxyalkyl-3-alkylimidazolium cations are, for example 1-methoxymethyl-3-methylimidazolium, 1-methoxymethyl-3-ethylimidazolium, 1-methoxymethyl-3-butylimidazolium, 1-(2-methoxyethyl)-3-methylimidazolium, 1-(2-methoxyethyl)-3-ethylimidazolium, 1-(2-methoxyethyl)-3-propylimidazolium, 1-(2-methoxyethyl)-3-butylimidazolium, 1-(2-ethoxyethyl)-3-methylimidazolium, 1-ethoxymethyl-3-methylimidazolium.

Preferred 1-alkenyl-3-alkylimidazolium cations are, for example 1-allyl-3-methyl-imidazolium or 1-allyl-2,3-dimethylimidazolium.

The organic cations of the compounds of formula I or compounds of formulae IA to IE according to the invention are preferably sulfonium, ammonium, phosphonium cations of formula (2), (3) and (4) or heterocyclic cations of formula (8), particularly preferably sulfonium cations of formula (2) or heterocyclic cations of formula (8) as described above.

The organic cations of the compounds of formula I according to the invention are very particularly preferably heterocyclic cations of formula (8) in which $HetN^{z+}$ is as defined above, where the substituents $R^{1'}$ to $R^{4'}$ each, independently of one another, have a meaning described above, for the application as electrolyte component. The organic cation of the compound of formula I is very particularly preferably imidazolium, where the substituents $R^{1'}$ to $R^{4'}$ each, independently of one another, have a meaning described above or has one of the particularly preferred meanings of 1,3-dialkylimidazolium, 1-alkenyl-3-alkylimidazolium or 1-alkoxyalkyl-3-alkylimidazolium as described above.

Particularly suitable organic cations of the formula I are for this application 1-butyl-1-methylpyrrolidinium, 1-ethyl-3-methylimidazolium, 1-ethyl-2,3-dimethylimidazolium, 1-(2-methoxyethyl)-3-methylimidazolium, 1-butyl-3-methylimidazolium, tributyl-methylammonium, tetra-n-butylammonium, tributyl-methylphosphonium, tetraphenylphosphonium, diethylmethylsulfonium, S-ethyl-N,N,N',N'-tetramethylisothiouronium, 1-allyl-3- methylimidazolium, 1-allyl-2,3-dimethylimidazolium, 1-cyanomethyl-3-methylimidazolium, 1-methyl-3-propinylimidazlium, 1,1-dimethylpyrrolidinium or trimethylsulfonium.

It goes without saying to the person skilled in the art that substituents, such as, for example, C, H, N, O, Cl, F, in the compounds according to the invention may be replaced by the corresponding isotopes.

Compounds of formula I in which $[Kt]^{z+}$ is Li$^+$ can be preferably used as conductive salts in primary batteries, secondary batteries, capacitors, supercapacitors or electrochemical cells, optionally also in combination with further conductive salts and/or additives, as constituent of a polymer electrolyte or phase-transfer medium.

Compounds of formula I or formulae IA to IE, in which $[Kt]^{z+}$ is Na$^+$ or K$^+$ can be preferably used as starting materials for compounds of formula I or formulae IA to IE in which $[Kt]^{z+}$ is an organic cation or another inorganic cation than sodium or potassium.

Compounds of formula I in which $[Kt]^{z+}$ corresponds to formula (2), (5), (6), (9), tritylium, pyrylium, 1-benzopyrylium or 2-benzopyrylium as described above or preferably described above are preferably used as cationic polymerization initiator, photo-polymerization initiator or photo-acid generator.

Particularly preferred organic cations to be used for this technical application corresponds to triarylsulfonium- or diaryliodonium cations in which aryl is defined as described above for the cations of formula (9). Very particularly preferred organic cations to be used for this technical application as cationic polymerization initiator, photo-polymerization initiator or photo-acid generator are triphenylsulfonium, tritolylsulfonium, p-(tertbutyl)phenyl-diphenylsulfonium, p-methoxyphenyl-diphenylsulfonium, p-C$_6$H$_{13}$S-phenyl-diphenylsulfonium, m- or (p-C$_6$H$_5$S-phenyl)diphenylsulfonium, tri[4-(4-acetyl-phenylsulfanyl)phenyl]sulfonium, tri(4-tert.butylphenyl)sulfonium, diphenyliodonium, ditolyliodonium, phenyltolyliodonium, di(p-tert-butylphenyl)iodonium, m- or (p-C$_6$H$_5$S-phenyl)-phenyliodonium or tolyl-(4-sec.-butylphenyl)iodonium.

In addition, the invention relates to a process for the preparation of a compound of formula I as described before in which $[Kt]^{z+}$ is an alkali metal cation, z denotes 1 and the sum of x+y+v denotes 3, which denotes a compound of formula I-1,

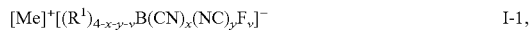

$[Me]^+[(R^1)_{4-x-y-v}B(CN)_x(NC)_yF_v]^-$  I-1, in which [Me]$^+$ denotes an alkali metal cation and R$^1$, x, y and v have a meaning as described or preferably described, comprising the reaction of a compound of formula II

$[Me]^+[(R^1)BF_3]^-$  II in which [Me]$^+$ denotes an alkali metal cation and R$^1$ has a meaning as described or preferably described above with trialkylsilylcyanide, in which the alkyl groups are each independently of one another straight-chain or branched alkyl having 1 to 8 C atoms.

Compounds of formula II are in most cases commercially available or can be synthesized by known processes.

Trialkylsilylcyanide in which the alkyl groups independently denotes straight-chain or branched alkyl groups having 1 to 8 C atoms are in some cases commercially available or can be synthesised by known processes. For example, it is possible to generate trialkylsilylcyanide by the reaction of alkalimetalcyanide with trialkylsilylchloride in the presence of alkalimetaliodide and optionally elemental iodine (M. T. Reetz, I. Chatziiosifidis, Synthesis, 1982, p. 330; J. K. Rasmussen, S. M. Heilmann and L. R. Krepski, The Chemistry of Cyanotrimethylsilane in G. L. Larson (Ed.) "Advances in Silicon Chemistry", Vol. 1, p. 65-187, JAI Press Inc., 1991; WO 2008/102661 A1).

The use of sodium cyanide and sodium iodide or potassium cyanide or potassiumiodide is particular preferred. Preferably, the alkalimetaliodide will be used in 0.1 mol/l related to 1 mol/l alkalicyanide and trialkylsilylchloride. The reaction has to be carried out in a dry atmosphere, for example under dry air, nitrogen or argon.

The alkyl groups of trialkylsilylcyanide may be the same or different. Preferably, they are the same. Examples of trialkylsilylcyanides are such as trimethylsilylcyanide, triethylsilylcyanide, dimethylethylsilylcyanide, triisopropylsilylcyanide, tripropylsilylcyanide or tributylsilylcyanide. Particularly preferred is the use of trimethylsilylcyanide.

This process can be carried out in air, preferably in a dry atmosphere, for example under dry air, nitrogen or argon.

Trialkylsilylchloride can be used as additive in the above described process in excess of 0.1 mol % to 50 mol % to the other described reagents. Addition of catalytic quantities (0.1 mol % to 50 mol %) or excess of trialkylsilylchloride when trialkylsilylcyanide is generated in situ accelerate the reaction of the compound of formula II as described above with trialkylsilylcyanide. Without being bound by said theory it is believed that trialkylsilylchloride acts in this reaction as catalyst.

The reaction for the synthesis of compounds of formula IA as described above in which $[Kt]^{z+}$ is an alkali metal cation is carried out without a solvent or with a solvent using at least 2 equivalents of the trialkylsilylcyanide which is described above.

Preferred organic solvents are acetonitrile, propionitrile, benzonitrile, monoglyme, diglyme, tetrahydrofurane or dioxane, preferably acetonitrile.

The reaction for the synthesis of compounds of formula IA as described above in which $[Kt]^{z+}$ is an alkali metal cation without a solvent is carried out at temperatures between 30° C. and 70° C., preferably at 50° C. and the reaction time is in the range of minutes to hours, preferably 30 minutes. Is the reaction carried out in an organic solvent, the reaction temperature is between 70° C. and 120° C., preferably at 100° C. and the reaction time is in the range of hours, preferably 4 hours. It is possible that this reaction is carried out in the presence of ethoxytrimethylsilane while the reaction temperature is in this case room temperature and the reaction time is in the range of hours, preferably 12 hours. The reaction time can be reduced by addition of catalytic amount of trialkylsilylchloride as additive as described before.

The reaction for the synthesis of compounds of formula IB or IC as described above in which $[Kt]^{z+}$ is an alkali metal cation is carried out without a solvent or with a solvent using at least 3 equivalents of the trialkylsilylcyanide which is described above.

In this type of reaction, the reaction is preferably carried out without a solvent.

The reaction for the synthesis of compounds of formula IB as described above in which $[Kt]^{z+}$ is an alkali metal cation without a solvent is carried out at temperatures between 70° C. and 120° C., preferably at 110° C. and the reaction time is in the range of days, preferably 3 days, followed by an oxidative purification with aqueous H$_2$O$_2$ (5-30 weight. %)

In addition, it is possible to isomerise a compound of formula IC as described above, in which $[Kt]^{z+}$ is an alkali metal cation through heating at temperatures between 70° C. and 120° C. resulting in the corresponding compound of formula IB having the same alkali metal cation as the starting material. The reaction conditions, especially the reaction temperatures and reaction times strongly depend on the kind of the substituent $R^1$. Slight modifications belong to the general knowledge of the artisan in the field of preparative chemistry.

The reaction for the synthesis of compounds of formula IC as described above in which $[Kt]^{z+}$ is an alkali metal cation without a solvent is carried out at temperatures between 30° C. and 100° C., preferably at 50° C. to 80° C. and the reaction time is in the range of days, preferably 3 days.

Additionally, the invention is directed to a process for the preparation of a compound of formula I as described before in which $[Kt]^{z+}$ is an organic cation and the sum of x+y+v denotes 3,
comprising the reaction of a compound of formula III

$$[Kt]^{z+}[(R^1)BF_3]^- \quad\quad III$$

in which $[Kt]^{z+}$ denotes the organic cation and $R^1$ has a meaning as described above with trialkylsilylcyanide, in which the alkyl groups are each independently of one another straight-chain or branched alkyl having 1 to 8 C atoms. The reaction time can be reduced by addition of catalytic amount of trialkylsilylchloride as additive as described before.

The reaction for the synthesis of compounds of formula ID in which $[Kt]^{z+}$ is an organic cation via the above described reaction of a compound of formula III as described before is carried out with a solvent using 1 equivalent of the trialkylsilylcyanide as described before. This reaction is carried out at room temperature within a reaction time of days, preferably 3 days. The reaction time can be reduced by addition of catalytic amount of trialkylsilylchloride as additive as described before.

The reaction for the synthesis of compounds of formula IC in which $[Kt]^{z+}$ is an organic cation via the above described reaction of a compound of formula III as described before is carried out with a solvent using 3 equivalents of the trialkylsilylcyanide as described above. This reaction is carried out at room temperature and heated up to 90° C. within a reaction time of days, preferably 3 days. The reaction time can be reduced by addition of catalytic amount of trialkylsilylchloride as additive as described before.

In addition, the invention relates to a process for the preparation of a compound of formula I as described before in which $[Kt]^{z+}$ is an alkali metal cation, z denotes 1 and the sum of x+y+v denotes 2, comprising the reaction of a compound of formula IV

$$(R^1)_2BOCH_3 \quad\quad IV$$

in which $R^1$ has a meaning as described above with trialkylsilylcyanide in the presence of an alkali metal fluoride, wherein the alkyl groups within the trialkylsilylcyanide are each independently of one another straight-chain or branched alkyl having 1 to 8 C atoms.

This process describes especially the synthesis of compounds of formula IE.

A compound of formula IV which is commercially available, is reacted with at least 2 equivalents of trialkylsilylcyanide in the presence of an alkali metal fluoride followed by an oxidative purification with aqueous $H_2O_2$ (5-30 weight %). This reaction is carried out in an organic solvent, preferably acetonitrile and the reaction temperature is room temperature and the reaction time is hours, preferably 12 hours.

In addition, the invention relates to a process for the preparation of a compound of formula I as described above in which $[Kt]^{z+}$ is another cation than the used alkali metal cation in the starting material in a salt-exchange reaction, characterized in that an alkali metal salt of formula I-1

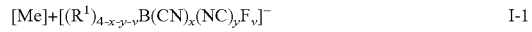

$$[Me]+[(R^1)_{4-x-y-v}B(CN)_x(NC)_yF_v]^- \quad\quad I\text{-}1$$

in which $[Me]^+$ is an alkali metal cation and $R^1$, x, y, v and the sum of x+y+v have a meaning as described or preferably described before 1 is reacted with a compound of formula V

$$KtA \quad\quad V,$$

in which
Kt has a meaning of an organic cation or an inorganic cation other than the alkali metal cation of the compound of formula I-1 and
A denotes $F^-$, $Cl^-$, $Br^-$, $I^-$, $OH^-$, $[HF_2]^-$, $[CN]^-$, $[SCN]^-$, $[R_1COO]^-$, $[R_1OC(O)O]^-$, $[R_1SO_3]^-$, $[R_2COO]^-$, $[R_2SO_3]^-$, $[R_1OSO_3]^-$, $[BF_4]^-$, $[PF_6]^-$, $[HSO_4]^{1-}$, $[NO_3]^-$, $[(R_2)_2P(O)O]^-$, $[R_2P(O)O_2]^{2-}$, $[(R_1O)_2P(O)O]^-$, $[(R_1O)P(O)O_2]^{2-}$, $[(R_1O)R_1P(O)O]^-$, tosylate, malonate which may be substituted by straight-chain or branched alkyl groups having 1 to 4 C atoms, $[HOCO_2]^-$ or $[CO_3]^{2-}$ (merely for the synthesis of other compounds of formula I-1 having an other alkali metal cation than the starting material), in which $R_1$ is each independently of another a straight-chain or branched alkyl group having 1 to 12 C atoms and
$R_2$ is each independently of one another a straight-chain or branched perfluorinated alkyl group having 1 to 12 C atoms and where electroneutrality should be taken into consideration in the formula of the salt KtA.

$R_2$ is particularly preferred trifluoromethyl, pentafluoroethyl or nonafluorobutyl, very particularly preferred trifluoromethyl or pentafluoroethyl.

$R_1$ is particularly preferred methyl, ethyl, n-butyl, n-hexyl or n-octyl, very particularly preferred methyl or ethyl.

Compounds of formula I-1, as described above, are preferably used in the metathesis reaction as described above.

Substituted malonates are for example methyl malonate or ethyl malonate.

The compounds of formula V are in most cases commercially available or can be synthesised by known processes. Known processes for the preparation of compounds of formula V are described, for example, in P. Wasserscheid, T. Welton (Eds.), Ionic Liquids in Synthesis, Second Edition, WILEY-VCH, Weinheim, 2008.

The anion in the formula V is preferably $OH^-$, $Cl^-$, $Br^-$, $I^-$, $[HF_2]^-$, $[CN]^-$, $[SCN]^-$, $[CH_3OC(O)O]^-$, $[CH_3C(O)O]^-$, $[CH_3SO_3]^-$, $[CF_3C(O)O]^-$, $[CF_3SO_3]^-$, $[CH_3OSO_3]^-$, $[SiF_6]^{2-}$, $[BF_4]^-$, $[PF_6]^-$, $[HSO_4]^-$, $[NO_3]^-$, $[C_2H_5OSO_3]^-$, $[(C_2F_5)_2P(O)O]^-$, $[C_2F_5P(O)O_2]^{2-}$, tosylates, malonates or $[SO_4]^{2-}$ and $[CO_3]^{2-}$ with the proviso that $[SO_4]^{2-}$ and $[CO_3]^{2-}$ are used merely for the synthesis of compounds of formula I having another metal cation than the alkali metal cation of the compound of formula I-1, particularly preferably $OH^-$, $Cl^-$, $Br^-$, $I^-$, $[CH_3SO_3]^-$, $[CH_3OSO_3]^-$, $[CF_3COO]^-$, $[CF_3SO_3]^-$, $[(C_2F_5)_2P(O)O]^-$ or $[CO_3]^{2-}$.

The anion in the formula V is very particularly preferably $OH^-$, $Cl^-$, $Br^-$, $[CH_3OSO_3]^-$, $[CF_3SO_3]^-$, $[CH_3SO_3]^-$ for the synthesis of compounds of formula I having an inorganic cation and the anion in the formula V is very particularly preferably $OH^-$, $Cl^-$, $Br^-$, $[PF_6]^-$, $[CH_3OSO_3]^-$, $[CF_3SO_3]^-$, $[CH_3SO_3]^-$ or $[(C_2F_5)_2P(O)O]^-$ for the synthesis of compounds of formula I having an organic cation or alternatively very particularly preferably $OH^-$, $Cl^-$, $Br^-$, $[CH_3OSO_3]^-$, $[CF_3SO_3]^-$, $[CH_3SO_3]^-$ or $[(C_2F_5)_2P(O)O]^-$ for the synthesis of compounds of formula I having an organic cation.

Suitable organic salts for the preparation of the compounds of the formula I in which $[Kt]^{z+}$ is an organic cation are salts with cations of formula (1) to (9) or tritylium or their preferred embodiments together with anions as defined as A described above or its preferred embodiments which means salts of cations of formula (1) to (9) or their preferred embodiments and OH⁻, Cl⁻, Br⁻, [PF$_6$]⁻, [CH$_3$OSO$_3$]⁻, [CF$_3$SO$_3$]⁻, [CH$_3$SO$_3$]⁻ or [(C$_2$F$_5$)$_2$P(O)O]⁻ anions.

Suitable substance for the preparation of the compound of the formula I in which [Kt]$^{z+}$ is H⁺ are aqueous H[BF$_4$] and H[PF$_6$] or H[BF$_4$] and H[PF$_6$] in organic solvents, preferably in diethylether. Reaction of K[R$^1$B(CN)$_3$] or Na[R$^1$B(CN)$_3$] with H[BF$_4$] or H[PF$_6$]results in the formation of H[R$^1$B(CN)$_3$] in solvated form in which R$^1$ has a meaning as described or preferably described above and poorly soluble potassium or sodium hexafluorophosphate or tetrafluoroborate.

Suitable inorganic salts for the preparation of the compounds of the formula I in which [Kt]$^{z+}$ is a metal cation e.g. from the group silver, magnesium, copper, zinc and calcium are, for example, Ag$_2$O, Ag$_2$CO$_3$, MgCO$_3$, CuO, ZnO, Zn[HCO$_3$]$_2$, CaCO$_3$ or Ca(OC(O)CH$_3$)$_2$. Useful salts for metathesis reaction to another alkali metal salt of formula I than potassium are e.g. LiBF$_4$ or LiPF$_6$.

The reaction is advantageously carried out in water in the case of the compounds of formula I-1 or in organic solvent, where temperatures of 10°-100° C., preferably 15°-60° C., particularly preferably room temperature, are suitable.

However, the reaction can alternatively also be carried out for the compounds of formula I in organic solvents at temperatures between 10° and 100° C. Suitable solvents here are acetonitrile, dialkylethers, tetrahydrofurane, dioxane, dichloromethane, dimethoxyethane or an alcohol, for example methanol, ethanol or iso-propanol.

The present invention furthermore relates to the use of the compounds of formula I as described above as media for chemical reactions, as catalyst and/or as media in catalytical processes, as conducting salts, as components of electrolytes for the application in electrochemical cells, as components of supporting electrolytes for electrochemical processes, as surfactants, as phase-transfer catalysts, as entrainer, as extractant; as antistatic additive, as plasticiser; as heat-transfer-medium, as modifier for membranes and textile materials; as lubricant, as additive to lubricant compositions or to other engineering fluids; as hydraulic fluid or as additive to hydraulic fluids.

Preferably, compounds of formula I having inorganic cations as described above are useful as catalyst, as conducting salts, as components of electrolytes for the application in electrochemical cells, as components of supporting electrolytes for electrochemical processes, as surfactants, as phase-transfer catalysts or as antistatic additive.

Preferably, compounds of formula I having organic cations as described above or H⁺ are useful as media for chemical reactions, as catalyst and/or as media in catalytical processes, as conducting salts, as components of electrolytes for the application in electrochemical cells, as components of supporting electrolytes for electrochemical processes, as surfactants, as phase-transfer catalysts, as entrainer, as extractant; as antistatic additive, as plasticiser; as heat-transfer-medium, as modifier for membranes and textile materials; as lubricant, as additive to lubricant compositions or to other engineering fluids; as hydraulic fluid or as additive to hydraulic fluids.

In the case of the use of the said organic salts of formula I as media in catalytical processes or as solvents, these are suitable in any type of reaction known to the person skilled in the art, for example for transition-metal- or enzyme-catalysed reactions, such as, for example, hydroformylation reactions, oligomerisation reactions, esterifications or isomerisations, where the said list is not exhaustive.

On use as extractant, the organic salts of formula I can be employed to separate off reaction products, but also to separate off impurities, depending on the solubility of the respective component in the ionic liquid. In addition, the ionic liquids may also serve as separation media in the separation of a plurality of components, for example in the distillative separation of a plurality of components of a mixture.

Further possible applications are use as plasticiser in polymer materials and as conductive salt or additive in various electrochemical cells and applications, for example in galvanic cells, in capacitors or in fuel cells.

Further fields of applications of the organic salts of formula I, according to this invention are solvents for carbohydrate containing solids in particular biopolymers and derivatives or degradation products thereof. In addition, these new compounds can be applied as lubricants, working fluids for machines, such as compressors, pumps or hydraulic devices. A further field of application is the field of particle or nanomaterial synthesis where these ionic liquids can act as medium or additive.

The compounds of formula I in which [Kt]$^{z+}$ corresponds to formula (2), (5), (6), (9), tritylium, pyrylium, 1-benzopyrylium or 2-benzopyrylium as described above or preferably described above are preferably used as cationic polymerization initiator, photo-polymerization initiator or photo-acid generator.

A cationic polymerization initiator is able to start the polymerization of at least one monomer, for example the polymerization of cationic polymerizable compounds such as isobutylene, styrene, vinylethers, lactones, lactames, cyclic ethers or epoxy-containing compounds.

The process of polymerization is started via radiation in case a photo-polymerization initiator is used which means that the mixture of photoinitiator and at least one monomer is irradiated through energetic rays such as light, electrons or gamma rays. This kind of photo-polymerization normally leads especially to quickly crosslinked end products. The compounds of formula I with cations of formula (2), (5), (6), (9), tritylium, pyrylium, 1-benzopyrylium or 2-benzopyrylium as described above are cationic photo-polymerization initiators. Particularly, compounds of formula I with cations of formula (2) and (9) are preferred.

Photo-polymerization initiators are often components of formulations of lacquers or resins which often need a curing in fractional amounts of seconds. The curing may be initiated through light, laser, electrons or gamma rays, especially through UV-light.

Photo-polymerization is often used in various technical applications for example for curing a coating film, forming a planographic printing plate, a resin letterpress printing plate and a printed circuit board, preparing a photoresist and a photomask, and making a black-and-white or color transfer sheet and a coloring sheet.

In case the compounds of formula I with cations of formula (2), (5), (6), (9), tritylium, pyrylium, 1-benzopyrylium or 2-benzopyrylium are irradiated with light, laser, electrons or gamma rays, they are able to build the corresponding Brønsted acid or Lewis acid on spot which means in a catalytic amount and are therefore able to start the polymerization through this acid. Such compounds which show such a property are commonly known as photo-acid generator (PAG). PAG's are highly active and have been shown to catalyze the deprotection of acid-sensitive organic functional groups with good photospeeds. PAG's are very often used in resists.

Another object of the invention is therefore a curable composition comprising at least one compound of formula I with cations of formula (2), (5), (6), (9), tritylium, pyrylium, 1-benzopyrylium or 2-benzopyrylium as described before and at least one polymerizable compound.

Another object of the invention is therefore a curable composition comprising at least one compound of formula I with cations of formula (2) and (9) as described or preferably described before and at least one polymerizable compound.

The compounds of formula I with organic cations, e.g. ionic liquids according to this invention may be preferably used in electrochemical and/or optoelectronic devices, especially in electrolyte formulations.

The present invention therefore relates furthermore to an electrolyte formulation comprising at least one compound of formula I as described above or preferably described.

Electrolyte formulations comprising compounds of formula I in which $[Kt]^{z+}$ is $Li^+$ or an organic cation can be preferably used in primary batteries, secondary batteries, capacitors, supercapacitors or electrochemical cells, optionally also in combination with further conductive salts and/or additives, as constituent of a polymer electrolyte or phase-transfer medium. Preferred batteries are lithium batteries or lithium-ion batteries. A preferred capacitor is a lithium-ion capacitor.

Electrolyte formulations comprising compounds of formula I as described or preferably described before can be preferably used in electrochemical and/or optoelectronic devices such as a photovoltaic cell, a light emitting device, an electrochromic or photo-electrochromic device, an electrochemical sensor and/or biosensor, particularly preferred in a dye sensitized solar cell.

Such electrolyte formulations form a crucial part of the disclosed devices and the performance of the device largely depends on the physical and chemical properties of the various components of these electrolytes.

Factors which are still impeding the technical application of many electrochemical and/or optoelectronic devices and in particular of dye or quantum dot sensitized solar cells, are reliability problems caused by the volatility of organic solvents based electrolytes. It is very difficult to maintain a tight sealing of the electrolyte in e.g. a DSC panel, which has to withstand the temperature differences of daily day-night cycles and the concomitant thermal expansion of the electrolyte. The abbreviation DSC means dye sensitized solar cell. This problem can be solved in principle by the use of ionic liquid-based electrolytes. For review "Ionic liquid electrolytes for dye-sensitized solar cells" see: William R Pitner et al., "Application of Ionic Liquids in Electrolyte System" *Green Chemistry*. vol. 6, (2010). Ionic liquids or liquid salts are typically ionic species which consist of an organic cation and a generally inorganic anion usually having melting points below 373 K. Various binary ionic liquid electrolytes have recently been applied to dye-sensitized solar cells. WO 2007/093961 and WO 2009/083901 describe so far the best power conversion efficiencies in ionic liquid-based electrolytes for DSC containing a significant quantity of organic salts with tetracyanoborate (TCB) anions.

Electrolyte formulations according to the invention are alternatives to already known electrolyte formulations. They show especially in the field of electrolyte formulations of dye sensitized solar cells an good performance particularly under high temperature. The advantage of the use of compounds of formula I having an organic cation and an alkyl-cyano-borate or alkyl-cyanofluoroborate anion is their low viscosity and good thermal stability.

In chemistry, an electrolyte is any substance containing free ions that make the substance electrically conductive. The most typical electrolyte is an ionic solution, but molten electrolytes and solid electrolytes are also possible.

An electrolyte formulation according to the invention is therefore an electrically conductive medium, basically due to the presence of at least one substance that is present in a dissolved and or in molten state and undergo dissociation into ionic species, i.e. supporting an electric conductivity via motion of ionic species. However, the said electric conductivity may not be of the major relevance to the role of the electrolyte of a dye-sensitised solar cell. Therefore, the scope of this invention is not limited to highly conductive electrolyte media.

The term electrolyte may be used for the term electrolyte formulation as well comprising all ingredients as disclosed for the electrolyte formulation.

Typical molar concentrations of the borate anion as disclosed in formula I as described above or in formulae IA to ID as described above in the electrolyte formulations range from 0.1 to 5.5 M, preferably from 0.8 to 3.5 M. This molar concentration in the electrolyte may be achieved with one or more compounds of formula I in which $Kt^{z+}$ has a meaning as described or preferably described above.

Preferably, the molar concentration is achieved with at least one compound of formula I as described or preferably described above.

For the purpose of the present invention, the molar concentration refer to the concentration at 25° C.

The present invention relates furthermore to an electrolyte formulation comprising at least one compound of formula I as described above or preferably described together with redox active species such as iodide/triiodide, Ferrocene derivatives or Co(II)/Co(III) complex couples such as Co(II)/Co(III)(dbbip)$_2$ in which dbbip means 2,6-bis(1'-butylbenzimidazol-2'-yl)pyridine, Co(II)/Co(III)(bpy)$_3$ where bpy denotes bipyridine or alkylated bipyridine derivates thereof, the counter anion being either perchlorate, fluoroperfluoroalkylphosphate such as perfluoroethylpentafluorophosphate, or (fluoro)cyanoborate, particularly tetracyanoborate, preferably a redox couple of iodine and at least one iodide salt.

The electrolyte formulation of the invention preferably comprises iodine ($I_2$). Preferably, it comprises from 0.0005 to 7 mol/dm$^3$, more preferably 0.01 to 5 mol/dm$^3$ and most preferably from 0.05 to 1 mol/dm$^3$ of $I_2$.

The iodide salt consists of an inorganic or organic cation and r as anion. There exists no limitation to the kind of cation. However, to limit the amount of different cations in the electrolyte formulations, especially for DSC, organic cations preferably be used as already described for the compounds of formula I. Particularly preferably, the electrolyte formulation comprises at least one iodide salt in which the organic cation is independently selected from the group of

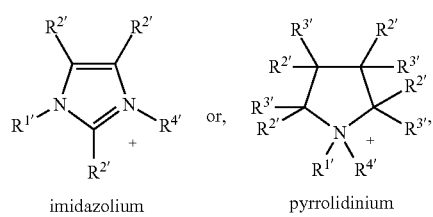

imidazolium      pyrrolidinium in which the substituents $R^{2'}$ and $R^{3'}$ each, independently of one another, denote H or straight-chain or branched alkyl having 1 to 20 C atoms, $R^{1'}$ and $R^{4'}$ each, independently of one another, denote straight-chain or branched alkyl having 1-20 C atoms, which optionally may be partially fluorinated or perfluorinated, straight-chain or branched alkenyl having 2-20 C atoms and one or more double bonds, which optionally may be partially fluorinated, straight-chain or branched alkynyl having 2-20 C atoms and one or more triple bonds, which optionally may be partially fluorinated.

Particularly preferred examples of the at least one iodide salt are 1-ethyl-3-methylimidazolium iodide (emim I), 1-propyl-3-methylimidazolium iodide (pmim I), 1-butyl-3-methyl-imidazolium iodide (bmim I), 1-hexyl-3-methylimidazolium iodide (hmim I), 1,3-dimethyl-imidazolium iodide (mmim I), 1-allyl-3-methylimidazolium iodide (amim I), N-butyl-N-methylpyrrolidinium iodide (bmpl I) or N,N-dimethyl-pyrrolidinium iodide (mmpl I).

Other components of the electrolyte formulation are one or several further salts, solvents, and others, as indicated further below.

If the electrolyte formulation is a binary system, it comprises two salts, one further salt or iodide salt and a compound of formula I as described above. If the electrolyte formulation is a ternary system, it comprises two further salts and/or iodide salts and a compound of formula I as described above. The binary system comprises 90-10 weight %, preferably 70-30 weight %, more preferably 55-40 weight % of the further salt or iodide salt and 10-90 weight %, preferably 30-70 weight % or more preferably 45-60 weight % of the compound of formula I as described above. The percentages in this paragraph are expressed with respect to the total of salts (=100 weight %) present in the electrolyte formulation according to the invention. Amounts of further, generally optional components (additives) indicated below, such as N-containing compounds having unshared electron pairs, iodine, solvents, polymers, and nanoparticles, for example, are not considered therein. The same percentages apply to ternary or quaternary systems which means the total of the further salts has to be used in the given ranges, e.g. two further ionic liquids are comprised in e.g. 90-10 weight. % in the electrolyte formulation according to the invention.

According to another embodiment of the present invention, the electrolyte formulation comprises at least one further salt with organic cations comprising a quaternary nitrogen and an anion selected from a F$^-$, Cl$^-$, a polyhalide ion, a fluoroalkanesulfonate, a fluoroalkanecarboxylate, a tris(fluoroalkylsulfonyl)methide, a bis(fluoroalkylsulfonyl)imide, bis(fluorsulfonyl)imide, a nitrate, a hexafluorophosphate, a tris-, bis- and mono-(fluoroalkyl)fluorophosphate, a tetrafluoroborate, a dicyanamide, a tricyanomethide, a tetracyanoborate, a thiocyanate, an alkylsulfonate or an alkylsulfate, with fluoroalkane-chain having 1 to 20 C atoms, preferably perfluorinated, fluoroalkyl having 1 to 20 C atoms and alkyl having 1 to 20 C atoms. Fluoroalkane-chain or fluoroalkyl is preferably perfluorinated.

Preferably, the further salts are selected from salts comprising anions such as thiocyanate or tetracyanoborate, particularly preferred further salts are tetracyanoborates.

The cation of the at least one further salt or of a preferred further salt may be selected amongst organic cations as defined above for the compounds of formula I including also the preferred meanings.

In another embodiment of the invention, guanidinium thiocyanate may be added to the electrolyte formulation according to the invention.

In a preferred embodiment, the electrolyte formulation of the present invention further comprises at least one compound containing a nitrogen atom having non-shared electron pairs. Examples of such compounds are found in EP 0 986 079 A2, starting on page 2, lines 40-55, and again from page 3, lines 14 extending to page 7, line 54, which are expressly incorporated herein by reference. Preferred examples of compounds having non-shared electron pairs include imidazole and its derivatives, particularly benzimidazole and its derivatives.

The electrolyte formulation of the present invention comprises less than 50 vol. % of an organic solvent. Preferably, the electrolyte formulation comprises less than 40%, more preferably less than 30%, still more preferably less than 20% and even less than 10%. Most preferably, the electrolyte formulation comprises less than 5% of an organic solvent. For example, it is substantially free of an organic solvent. Percentages are indicated on the basis of weight %.

Organic solvents, if present in such amounts as indicated above, may be selected from those disclosed in the literature. Preferably, the solvent, if present, has a boiling point higher than 160 degrees centigrade, more preferably higher than 190 degrees such as propylene carbonate, ethylene carbonate, butylene carbonate, gamma-butyrolactone, gammavalerolactone, glutaronitrile, adiponitrile, N-methyloxazolidinone, N-methylpyrrolidinone, N,N'-dimethylimidazolidinone, N,N-dimethylacetamide, cyclic ureas preferably 1,3-dimethyl-2-imidazolidinone or 1,3-dimethyl-3,4,5,6-tetrahydro-2(1H)-pyrimidinone, glymes preferably tetraglyme, sulfolane, sulfones which are preferably asymmetrically substituted such as 2-ethanesulfonyl-propane, 1-ethanesulfonyl-2-methyl-propane or 2-(propane-2-sulfonyl)-butane, 3-methylsulfolane, dimethylsulfoxide, trimethylphosphate and methoxy-substituted nitriles. Other useful solvents are acetonitrile, benzonitrile and or valeronitrile.

If a solvent is present in the electrolyte formulation, there may further be comprised a polymer as gelling agent, wherein the polymer is polyvinylidenefluoride, polyvinylidenehexafluoropropylene, polyvinylidenehexafluoropropylene-chlorotrifluoroethylene copolymers, nafion, polyethylene oxide, polymethylmethacrylate, polyacrylonitrile, polypropylene, polystyrene, polybutadiene, polyethyleneglycol, polyvinylpyrrolidone, polyaniline, polypyrrole, polythiophene. The purpose of adding these polymers to electrolyte formulations is to make liquid electrolytes into quasi-solid or solid electrolytes, thus improving solvent retention, especially during aging.

The electrolyte formulation of the invention may further comprise metal oxide nanoparticles like $SiO_2$, $TiO_2$, $Al_2O_3$, MgO or ZnO, for example, which are also capable of increasing solidity and thus solvent retention.

The electrolyte formulation of the invention has many applications. For example, it may be used in an optoelectronic and/or electrochemical device such as a photovoltaic cell, a light emitting device, an electrochromic or photo-electrochromic device, an electrochemical sensor and/or biosensor.

The present invention therefore relates further to the use of the electrolyte formulation as described in detail above in an electrochemical and/or optoelectronic device which is a photovoltaic cell, a light emitting device, an electrochromic or photo-electrochromic device, an electrochemical sensor and/or biosensor. Preferably, the electrolyte formulation may be used in dye sensitized solar cells.

The present invention therefore relates furthermore to an electrochemical and/or optoelectronic device which is a photovoltaic cell, a light emitting device, an electrochromic or photo-electrochromic device, an electrochemical sensor and/or biosensor comprising an electrolyte formulation comprising at least one compound of formula I as described or preferably described above.

Preferably, the compound of formula I is a compound of formula I in which [Kt]$^{z+}$ is an organic cation as described above including all preferred meanings for application in dye-sensitized solar cells.

According to a preferred embodiment, the device of the present invention is a dye or quantum dot sensitized solar cell, particularly preferably a dye sensitized solar cell.

Quantum dot sensitized solar cells are disclosed in U.S. Pat. No. 6,861,722, for example. In dye-sensitized solar cells, a dye is used to absorb the sunlight to convert into the electrical energy. There are no restrictions per se with respect to the choice of the dye as long as the LUMO energy state is marginally above the conduction bandage of the photoelectrode to be sensitized. Examples of dyes are disclosed in EP 0 986 079 A2, EP 1 180 774 A2 or EP 1 507 307 A1.

Preferred dyes are organic dyes such as MK-1, MK-2 or MK-3 (its structures are described in FIG. 1 of N. Koumura et al, J. Am. Chem. Soc. Vol 128, no. 44, 2006, 14256-14257), D102 (CAS no. 652145-28-3), D-149 (CAS no. 786643-20-7), D205 (CAS no. 936336-21-9), D358 (CAS no. 1207638-53-6), YD-2 as described in T. Bessho et al, Angew. Chem. Int. Ed. Vol 49, 37, 6646-6649, 2010, Y123 (CAS no. 1312465-92-1), bipyridin-Ruthenium dyes such as N3 (CAS no. 141460-19-7), N719 (CAS no. 207347-46-4), Z907 (CAS no. 502693-09-6), C101 (CAS no. 1048964-93-7), C106 (CAS no. 1152310-69-4), K19 (CAS no. 847665-45-6), HRS-1 (CAS no. 906061-30-1 as disclosed in K. J. Jiang et al, Chem. Comm. 2460, 2006) or terpyridine-Ruthenium dyes such as N749 (CAS no. 359415-47-7). The structure of D205 is

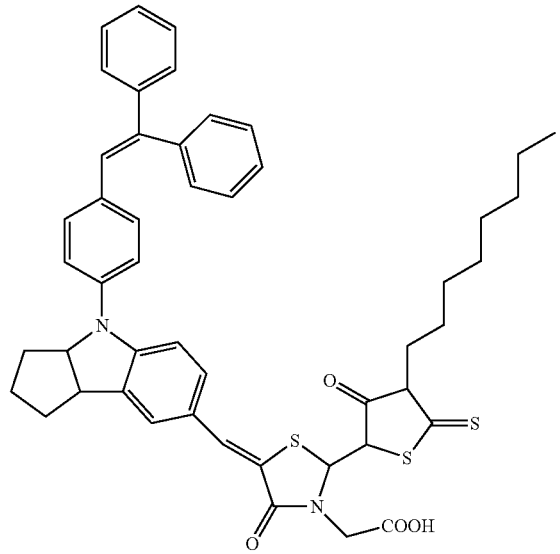 [SMILES: CCCCCCCCC1C(=O)C(C2S/C(=C\c3ccc4c(c3)C3CCCC3N4c3ccc(C=C(c4ccccc4)c4ccccc4)cc3)C(=O)N2CC(=O)O)SC1=S]

The structure of D358 is

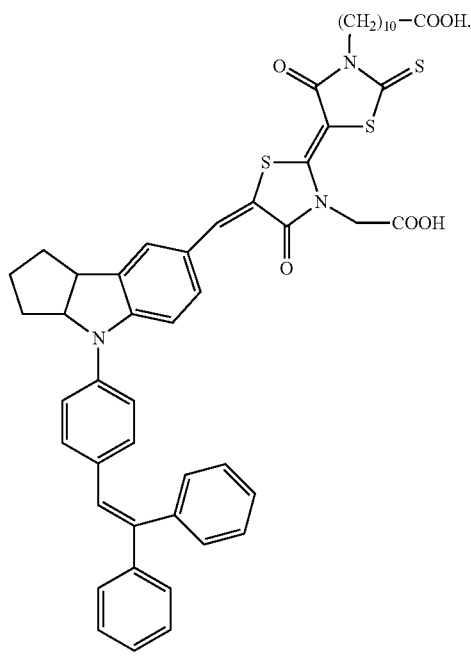

Particularly preferred dyes are Z907 or Z907Na which are both an amphiphilic ruthenium sensitizer, C106, D358 or HRS-1. The dye Z907Na means NaRu(2,2'-bipyridine-4-carboxylic acid-4'-carboxylate)(4,4'-dinonyl-2,2'-bipyridine)(NCS)$_2$.

Very particularly preferred dyes are Z907 or Z907Na and/or D358. Very very particularly preferred dyes are Z907 or Z907Na.

In a preferred embodiment, the dye is coadsorbed with a phosphinic acid. A preferred example of a phosphinic acid is bis(3,3-dimethyl-butyl)-phosphinic acid (DINHOP) as disclosed in M. Wang et al, Dalton Trans., 2009, 10015-10020.

The dye Z907Na means NaRu(2,2'-bipyridine-4-carboxylic acid-4'-carboxylate)(4,4'-dinonyl-2,2'-bipyridine)(NCS)$_2$.

For example, a dye-sensitized solar cell comprises a photoelectrode, a counter electrode and, between the photo-electrode and the counter electrode, an electrolyte formulation or a charge transporting material, and wherein a sensitizing dye is absorbed on the surface of the photo-electrode, on the side facing the counter electrode.

According to a preferred embodiment of the device according to the invention, it comprises a semiconductor, the electrolyte formulation as described above and a counter electrode.

According to a preferred embodiment of the invention, the semiconductor is based on material selected from the group of Si, TiO$_2$, SnO$_2$, Fe$_2$O$_3$, WO$_3$, ZnO, Nb$_2$O$_5$, CdS, ZnS, PbS, Bi$_2$S$_3$, CdSe, GaP, InP, GaAs, CdTe, CuInS$_2$, and/or CuInSe$_2$. Preferably, the semiconductor comprises a mesoporous surface, thus increasing the surface optionally covered by a dye and being in contact with the electrolyte. Preferably, the semiconductor is present on a glass support or plastic or metal foil. Preferably, the support is conductive.

The device of the present invention preferably comprises a counter electrode. For example, fluorine doped tin oxide or tin doped indium oxide on glass (FTO- or ITO-glass, respectively) coated with Pt, carbon of preferably conductive allotropes, polyaniline or poly(3,4-ethylenedioxythiophene) (PEDOT). Metal substrates such as stainless steel or titanium sheet may be possible substrates beside glass.

The device of the present invention may be manufactured as the corresponding device of the prior art by simply replacing the electrolyte by the electrolyte formulation of the present invention. For example, in the case of dye-sensitized solar cells, device assembly is disclosed in numerous patent literature, for example WO 91/16719 (examples 34 and 35), but also scientific literature, for example in Barbé C. J., Arendse, F., Comte, P., Jirousek, M., Lenzmann, F., Shklover, V., Grätzel, M. J. Am. Ceram. Soc. 1997, 80, 3157; and Wang, P., Zakeeruddin, S. M., Comte, P., Charvet, R., Humphry-Baker, R., Grätzel, M. J. Phys. Chem. B 2003, 107, 14336.

Preferably, the sensitized semi-conducting material serves as a photoanode. Preferably, the counter electrode is a cathode.

The present invention provides a method for preparing a photoelectric cell comprising the step of bringing the electrolyte formulation of the invention in contact with a surface of a semiconductor, said surface optionally being coated with a sensitizer. Preferably, the semiconductor is selected from the materials given above, and the sensitizer is preferably selected from quantum dots and/or a dye as disclosed above, particularly preferably selected from a dye.

Preferably, the electrolyte formulation may simply be poured on the semiconductor. Preferably, it is applied to the otherwise completed device already comprising a counter electrode by creating a vacuum in the internal lumen of the cell through a hole in the counter electrode and adding the electrolyte formulation as disclosed in the reference of Wang et al., J. Phys. Chem. B 2003, 107, 14336.

The present invention will now be illustrated, without limiting its scope, by way of the following examples. Even without further comments, it is assumed that a person skilled in the art will be able to utilise the above description in the broadest scope. The preferred embodiments and examples should therefore merely be regarded as descriptive disclosure which is absolutely not limiting in any way.

EXAMPLES

NMR samples were measured in 5 mm precision glass NMR tubes at 25° C. on a Bruker Avance III spectrometer equipped with a 9.3980 T cryomagnet. The $^1$H and $^{19}$F NMR spectra were acquired using a 5 mm combination $^1$H/$^{19}$F probe operating at 400.17 and 376.54 MHz, respectively. The $^{31}$P NMR spectra were obtained using a 5 mm broad-band inverse probe operating at 161.99 MHz. The $^1$H NMR chemical shifts were referenced with respect to tetramethylsilane (TMS) using the chemical shifts 2.05 ppm for the solvent Aceton-D$_6$. The $^{13}$C-NMR chemical shifts were referenced to the chemical shifts 29.9 ppm for the solvent Aceton-D$_6$. The $^{19}$F NMR spectra were referenced with respect to CFCl$_3$ using the internal standard C$_6$H$_5$CF$_3$ (−63.9 ppm). The $^{31}$P NMR spectra were referenced with respect to aqueous H$_3$PO$_4$ (85%).

The aceton-D$_6$ was used as a solvent and Deuterium lock if it is not given separately.

The disclosed viscosities are measured by means of Anton Paar Stabinger Viskosimeter SV 3000.

Example 1

Potassium methyldicyanofluoroborate—K[CH$_3$BF(CN)$_2$]

A)

K[CH$_3$BF$_3$]+2(CH$_3$)$_3$SiCN→K[CH$_3$BF(CN)$_2$]+2(CH$_3$)$_3$SiF

Potassium methyltrifluoroborate, K[CH$_3$BF$_3$] (100 mg, 0.82 mmol), is suspended in trimethylsilyl cyanide (20 ml, 149.9 mmol) and stirred at 50° C. for 30 minutes. All volatile constituents are removed in vacuo, giving a colorless solid. The unreacted trimethylsilyl cyanide is recovered as a mixture with trimethylfluorosilane and can be employed for further reactions.

The yield of potassium methyldicyanofluoroborate, K[CH$_3$BF(CN)$_2$], is 110 mg (0.81 mmol). The purity is about 90%, and about 10% of K[CH$_3$B(CN)$_2$(NC)] are present as by-product.

$^{11}$B{$^1$H}-NMR: δ, ppm=−8.9 (d, $^1J_{F,B}$=56.4 Hz).

$^{19}$F-NMR: δ, ppm=−202.8 (qq, $^1J_{F,B}$=55.7 Hz, $^3J_{F,H}$=13.8 Hz, BF, 1F).

$^1$H{$^{11}$B}-NMR: δ, ppm=−0.11 (d, $^3J_{F,H}$=14.4 Hz, CH$_3$, 3H).

$^1$H-NMR: δ, ppm=−0.11 (dq, $^3J_{F,H}$=14.4 Hz, $^2J_{B,H}$≈4.3 Hz, CH$_3$, 3H).

Raman spectrum: ṽ (CN)=2211 cm$^{-1}$.

The by-product K[MeB(CN)$_2$(NC)] is detected by NMR spectroscopy, and the data are identical to those indicated in Example 3.

B)

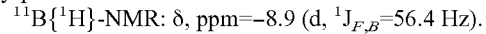

K[CH$_3$BF$_3$] + 2 (CH$_3$)$_3$SiCN $\xrightarrow{CH_3CN}$ K[CH$_3$BF(CN)$_2$] + 2 (CH$_3$)$_3$SiF Potassium methyltrifluoroborate (93.6 mg, 0.768 mmol) is taken up in acetonitrile (5 ml), trimethylsilyl cyanide (1.0 ml, 7.499 mmol) is added, and the mixture is stirred at 100° C. for 4 hours. All volatile constituents are subsequently removed in vacuo, and the residue is dissolved in acetone (1 ml). Potassium methyldicyanofluoroborate is precipitated by addition of chloroform (10 ml).

The yield of potassium methyldicyanofluoroborate is 94 mg (0.691 mmol). The spectroscopic data correspond to those from Example 1A.

C)

Potassium methyltrifluoroborate, K[CH$_3$BF$_3$] (500 mg, 4.10 mmol), is taken up in acetonitrile (5 ml). Trimethylsilyl cyanide (10 ml, 74.99 mmol) and ethoxytrimethylsilane (1.0 ml, 6.40 mmol) are added to the suspension, and the mixture is stirred at room temperature for 12 hours. All volatile constituents are subsequently removed. The residue is dissolved in acetone (5 ml), and K[CH$_3$BF(CN)$_2$] is precipitated by addition of CH$_2$Cl$_2$ (20 ml) and filtered off.

The yield of potassium methyldicyanofluoroborate is 492 mg (3.62 mmol). The spectroscopic data correspond to those from Example 1A.

D)

K[CH$_3$BF$_3$] + 2 (CH$_3$)$_3$SiCl + 2 KCN $\xrightarrow{CH_3CN}$ K[CH$_3$BF(CN)$_2$] + 2 (CH$_3$)$_3$SiF + 2 KCl KCN (400 mg, 6.15 mmol) and K[CH$_3$BF$_3$] (100 mg, 0.819 mmol) are suspended in acetonitrile (2 mL) and a solution of trimethylchlorsilane (0.3 mL, 2.38 mmol) in acetonitrile (5 mL) is added slowly. The suspension is stirred for 20 minutes at room temperature. The reaction mixture is filtered to remove all solid materials (excess of KCN as well as the side-product KCl). The solid material is washed with acetonitrile (2 mL) and the organic phases are combined. All volatile materials are removed under reduced pressure at 50° C.

The yield of potassium methyldicyanofluoroborate is 85 mg (0.63 mmol). The spectroscopic data of the product correspond to those from Example 1A.

Example 2

Potassium methyltricyanoborate—K[CH$_3$B(CN)$_3$]

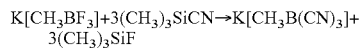

A) Potassium methyltrifluoroborate, K[CH$_3$BF$_3$] (7.00 g, 57.42 mmol), is suspended in trimethylsilyl cyanide (45.0 ml, 337.45 mmol) and warmed at 80° C. for one hour and subsequently stirred at 110° C. for 3 days. All volatile constituents was removed in vacuo, and the residue is dissolved in acetone (10 ml) and precipitated by addition of CHCl$_3$ (50 ml). The crude product is taken up in 20% aqueous hydrogen peroxide solution (50 ml) and stirred overnight. Potassium disulfite K$_2$S$_2$O$_5$ is added until peroxides were no longer detectable (Merckoquant® peroxide test). The product is then extracted with THF (3×25 ml), and the combined organic phases are dried using K$_2$CO$_3$, filtered and evaporated in vacuo to a volume of about 5 ml. CH$_2$Cl$_2$ (100 ml) is added with vigorous stirring, and the white precipitate formed is filtered off and dried in vacuo.

The yield of potassium methyltricyanoborate, K[CH$_3$B(CN)$_3$], is 5.1 g (35.67 mmol).

The NMR spectra of K[CH$_3$B(CN)$_3$] were measured in CD$_3$CN.
$^{11}$B{$^1$H}-NMR: δ, ppm=−32.6 s.
$^1$H{$^{11}$B}-NMR: δ, ppm=0.03 (s, CH$_3$, 3H).
$^1$H-NMR: δ, ppm=0.03 (q, $^2J_{B,H}$=−3 Hz, CH$_3$, 3H).
$^{13}$C{$^1$H}-NMR: δ, ppm=130.8 (q, $^1J_{C,B}$=64 Hz, CN), 3.3 (q, $^1J_{C,B}$=44 Hz, CH$_3$).

B) Potassium methyltrifluoroborate (7.9 g, 64.81 mmol) is suspended in a mixture (100 mL) of recycled trimethylsilylcyanide (90 mol %), fluorotrimethylsilane (4 mol %), chlorotrimethylsilane (2 mol %), acetonitril (4 mol %) and trimethylsilylcyanide (CH$_3$)$_3$SiCN (10.0 mL, 74.99 mmol) and (CH$_3$)$_3$SiCl (as catalyst, 10.0 mL, 79.16 mmol) is added. The mixture is heated to 75° C. and stirred for 9 hours. All volatile compounds are removed in vacuo and the residue is dissolved in water and stirred with aqueous H$_2$O$_2$ (30%, 15 mL) and K$_2$CO$_3$ (~5 g) for 2 hours resulting in a solution. Peroxide is reduced through K$_2$S$_2$O$_5$. The pH of the mixture remains basic through addition of potassium carbonate. The mixture is then extracted with tetrahydrofuran (5×75 mL) and the organic phases are dried with potassium carbonate, filtrated and the organic solvent is removed in vacuum. The resulting concentrated solution is added to CHCl$_3$ and the potassium salt K[CH$_3$B(CN)$_3$] precipitates and is filtrated and dried in vacuum.

The yield of potassium methyltricyanoborate is 7.8 g (54.54 mmol).
Elemental analysis:
Calculated C, 33.60; H, 2.11; N, 29.39.
found: C, 33.29; H, 2.59; N, 27.16.
The spectroscopic data of the product correspond to those from Example 2A.

Example 3

Potassium methyldicyanoisocyanoborate—K[CH$_3$B(CN)$_2$(NC)]

Potassium methyltrifluoroborate, K[CH$_3$BF$_3$] (500 mg, 4.10 mmol), is suspended in trimethylsilyl cyanide (20 ml, 149.9 mmol). The reaction mixture is stirred at 50° C. for 2 days and subsequently at 80° C. for 24 hours. Excess trimethylsilyl cyanide and trimethylfluorosilane formed are distilled off and can be employed for further reactions. A slightly reddish solid is obtained.

The yield of potassium methyldicyanoisocyanoborate, K[CH$_3$B(CN)$_2$(NC)], is 583 mg (4.08 mmol). The product contains about 10% of potassium methyltricyanoborate.

The NMR spectra of K[CH$_3$B(CN)$_2$(NC)]:
$^{11}$B{$^1$H}-NMR: δ, ppm=−23.9 s.
$^1$H{$^{11}$B}-NMR: δ, ppm=−0.02 (s, CH$_3$).
$^1$H-NMR: δ, ppm=−0.02 (broadened, CH$_3$).
MALDI-MS m/e [C$_4$H$_3$BN$_3$]$^-$:
calculated: 104.0 (100.0%), 103.0 (24.8%), 105.0 (4.4%).
found: 103.7 (100.0%), 102.7 (24.4%), 104.7 (4.3%).
Raman spectrum: $\tilde{\nu}$ (CN)=2221 cm$^{-1}$
Raman spectrum: $\tilde{\nu}$ (NC)=2166 cm$^{-1}$ The by-product K[MeB(CN)$_3$] is detected by NMR spectroscopy, and the data are identical to the values indicated in Example 2.

The product, K[CH$_3$B(CN)$_2$(NC)], isomerizes in potassium methyltricyanoborate, K[CH$_3$B(CN)$_3$], on heating in the solid state or in an organic solvent at about 100° C.

Example 4

Potassium n-butyldicyanoisocyanoborate—K[n-C$_4$H$_9$B(CN)$_2$(NC)]

Potassium n-butyltrifluoroborate, K[n-C$_4$H$_9$BF$_3$] (20 mg, 0.122 mmol), is weighed out in an NMR tube with a valve with Teflon spindle (Young, London) and taken up in trimethylsilyl cyanide (1.0 ml, 7.49 mmol). The suspension is stored at room temperature for two days and subsequently at 80° C. for 7 hours. The solution obtained is evaporated to dryness in vacuo.

Yield of potassium n-butyldicyanoisocyanoborate, K[n-C$_4$H$_9$B(CN)$_2$(NC)], is 22 mg (0.12 mmol). The product contains about 7% of potassium n-butyltricyanoborate, K[n-C$_4$H$_9$B(CN)$_3$].

The $^{11}$B-NMR spectrum of K[n-C$_4$H$_9$B(CN)$_2$(NC)]:
$^{11}$B{$^1$H}-NMR: δ, ppm=−22.2 s.
K[n-C$_4$H$_9$B(CN)$_3$]:
$^{11}$B{$^1$H}-NMR: δ, ppm=−30.6 s.
MALDI-MS m/e [C$_7$H$_9$BN$_3$]$^-$:
calculated: 146.1 (100.0%), 145.1 (24.8%), 147.1 (7.8%).
found: 145.8 (100.0%), 144.8 (14.7%), 146.8 (14.1%).

The product, K[n-C$_4$H$_9$B(CN)$_2$(NC)], isomerizes in potassium n-butyltricyanoborate, K[n-C$_4$H$_9$B(CN)$_3$], on heating in the solid state or in an organic solvent at about 100° C.

Example 5

Potassium n-butyltricyanoborate—K[n-C$_4$H$_9$B(CN)$_3$]

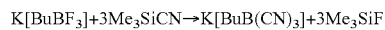

Potassium n-butyltrifluoroborate (5.2 g, 31.7 mmol) is suspended in a mixture (150 mL) of recycled trimethylsilylcyanide (86 mol %), fluorotrimethylsilane (4 mol %), chlorotrimethylsilane (3 mol %), acetonitril (4 mol %). The mixture is heated to 60° C. and stirred for 12 hours. All volatile compounds are removed in vacuo and the residue is dissolved in water (30 mL) and stirred with aqueous $H_2O_2$ (30%, 30 mL) and $K_2CO_3$ (~5 g) for 4 hours resulting in a solution. Peroxide is reduced through $K_2S_2O_5$. The pH of the mixture remains basic through addition of potassium carbonate. The mixture is then extracted with tetrahydrofuran (5×75 mL) and the organic phases are dried with potassium carbonate, filtrated and the organic solvent is removed in vacuum. The resulting concentrated solution is added to hexane and the potassium salt $K[n-C_4H_9B(CN)_3]$ precipitates and is filtrated and dried in vacuum.

The yield of potassium n-butyltricyanoborate is 4.8 g (25.94 mmol).

$^{11}B\{^1H\}$-NMR: δ, ppm=−31.5 (s).

$^{11}$B-NMR: δ, ppm=−31.5 (broad s).

$^1H\{^{11}B\}$-NMR: δ, ppm=1.30 (m, 4H, $CH_2$), 0.86 (m, 3H, $CH_3$), 0.43 (m, 2H, $BCH_2$).

$^1$H-NMR: δ, ppm=1.30 (m, 4H), 0.86 (m, 3H), 0.43 (broad m, $^3J_{H,H}$=7.3 Hz, 2H).

$^{13}C\{^1H\}$-NMR: δ, ppm=138.4 (q, $^1J_{C,B}$≈70 Hz, CN, 3C), 30.6 (s, 1C), 26.3 (s, 1C), 20.5 (q, $^1J_{C,B}$≈50 Hz, 1C), 14.3 (s, 1C).

Elemental analysis:

calculated: C, 45.43; H, 4.90; N, 22.70.

found: C, 44.10; H, 4.95; N, 22.14.

Example 6

1-Ethyl-3-methylimidazolium n-butyltricyanoborate—$EMIM[n-C_4H_9B(CN)_3]$ $EMIMCl+K[nC_4H_9B(CN)_3] \rightarrow EMIM[nC_4H_9B(CN)_3]+KCl$ 1-Ethyl-3-methylimidazolium chloride, (EMIMCl) (3.57 g, 24.36 mmol) and $K[nC_4H_9B(CN)_3]$ (4.1 g, 22.15 mmol) are dissolved in deionized water (50 mL) and the mixture is diluted with $CH_2Cl_2$ (50 mL). The aqueous phase is removed and the organic phase is washed with water (VE, 5×1 mL) and dried with magnesium sulfate. After filtration and distillation of methylene chloride, the ionic liquid is dried for three days at 50° C. in vacuum. The yield of 1-ethyl-3-methylimidazolium n-butyltricyanoborate is 5.1 g (19.83 mmol).

$^{11}B\{^1H\}$-NMR: δ, ppm=−33.5 (s).

$^{11}$B-NMR: δ, ppm=−33.5 (broad s).

$^1H\{^{11}B\}$-NMR: δ, ppm=8.99 (broad dd, $^4J_{H,H}$≈1.6 Hz, CH, 1H), 7.74 (dd, $^3J_{H,H}$≈$^4J_{H,H}$≈1.8 Hz, CH, 1H), 7.67 (dd, $^3J_{H,H}$≈$^4J_{H,H}$≈1.8 Hz, CH, 1H), 4.39 (q, $^3J_{H,H}$=7.4 Hz, $CH_2$, 2H), 4.02 (s, $CH_3$, 3H), 1.57 (t, $^3J_{H,H}$=7.3 Hz, $CH_3$, 3H), 1.31 (m, 4H, $CH_2$), 0.86 (m, 3H, $CH_3$), 0.43 (m, 2H, $CH_2$).

$^1$H-NMR: δ, ppm=8.99 (broad dd, $^4J_{H,H}$≈1.6 Hz, CH, 1H), 7.74 (dd, $^3J_{H,H}$≈$^4J_{H,H}$≈1.8 Hz, CH, 1H), 7.67 (dd, $^3J_{H,H}$≈$^4J_{H,H}$≈1.8 Hz, CH, 1H), 4.39 (q, $^3J_{H,H}$=7.4 Hz, $CH_2$, 2H), 4.02 (s, $CH_3$, 3H), 1.57 (t, $^3J_{H,H}$=7.3 Hz, $CH_3$, 3H), 1.31 (m, 4H, $CH_2$), 0.86 (m, 3H, $CH_3$), 0.43 (broad m, 2H, $CH_2$).

$^{13}C\{^1H\}$-NMR: δ, ppm=137.0 (s, 1C), 130.9 (q, $^1J_{C,B}$=62 Hz, CN, 3C), 124.7 (s, 1C), 123.0 (s, 1C), 45.7 (s, 1C), 36.6 (s, 1C), 30.6 (s, 1C), 26.3 (s, 1C), 20.9 (q, $^1J_{C,B}$≈44 Hz, 1C), 15.6 (s, 1C), 14.3 (s, 1C).

Elemental analysis:

calculated: C, 60.72; H, 7.84; N, 27.24.

found: C, 60.03; H, 8.12; N, 27.63.

Dynamic viscosity:

| ° C. | mPa · s |
|---|---|
| 20 | 49.8 |
| 40 | 21.3 |
| 60 | 11.4 |
| 80 | 7.0 |

Decomposition's temperature: 290° C.

Example 7

Potassium allyltricyanoborate—$K[CH_2=CHCH_2B(CN)_3]$

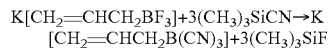

$K[CH_2=CHCH_2BF_3]+3(CH_3)_3SiCN \rightarrow K[CH_2=CHCH_2B(CN)_3]+3(CH_3)_3SiF$ Potassium allyltrifluoroborate, $K[CH_2=CHCH_2BF_3]$ (20 mg, 0.135 mmol), is initially introduced in an NMR tube with a valve with Teflon spindle (Young, London) and taken up in trimethylsilyl cyanide (1.0 ml, 7.49 mmol). The suspension is kept at room temperature for two days and subsequently at 80° C. for 7 hours, at 100° C. for 8 hours and then at 120° C. for 12 hours. All volatile constituents are removed in vacuo. The yield of potassium allyltricyanoborate, $K[CH_2=CHCH_2B(CN)_3]$, is 21 mg (0.124 mmol). The product contains about 2% impurities.

The $^{11}$B-NMR spectrum of $K[CH_2=CHCH_2B(CN)_3]$:

$^{11}B\{^1H\}$-NMR: δ, ppm=−30.8 s.

MALDI-MS m/e $[C_6H_5BN_3]^-$:

calculated: 130.0 (100.0%), 129.0 (24.8%), 131.0 (6.7%).

found: 129.7 (100.0%), 128.7 (31.7%), 130.7 (5.2%).

Example 8

1-Ethyl-3-methylimidazolium methyldicyanofluoroborate—$EMIM[CH_3BF(CN)_2]$

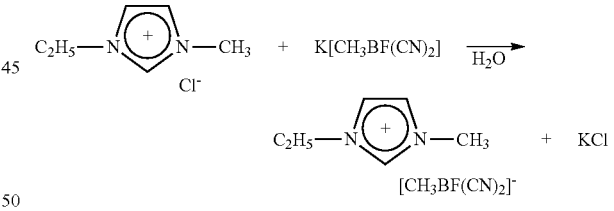

Potassium methyldicyanofluoroborate (50 mg, 0.367 mmol) and 1-ethyl-3-methylimidazolium chloride, EMIM Cl (100 mg, 0.684 mmol), are combined in deionized water (1 ml) and mixed. The reaction solution is extracted with $CH_2Cl_2$ (2×1 ml), and the $CH_2Cl_2$ is subsequently removed in vacuo. The liquid remaining is dried in vacuo for 12 hours.

The yield of EMIM $[CH_3BF(CN)_2]$ is 54 mg (0.259 mmol).

The NMR spectra of EMIM $[CH_3BF(CN)_2]$:

$^{11}B\{^1H\}$-NMR: δ, ppm=−8.9 d ($^1J_{F,B}$=56.5 Hz).

$^{11}$B-NMR: δ, ppm=−8.9 d,q ($^1J_{F,B}$=56.5 Hz, $^2J_{B,H}$≈4.3 Hz).

$^{19}$F-NMR: δ, ppm=−202.8 q,q ($^1J_{F,B}$=56.2 Hz, $^3J_{F,H}$=14.2 Hz, BF).

$^1H\{^{11}B\}$-NMR: δ, ppm=9.03 br. s (CH, 1H), 7.75 t ($^3J_{H,H}$≈$^4J_{H,H}$≈1.8 Hz, CH, 1H), 7.68 t ($^3J_{H,H}$≈$^4J_{H,H}$≈1.7 Hz, CH, 1H), 4.40 q ($^3J_{H,H}$=7.3 Hz, CH$_2$, 2H), 4.05 s (CH$_3$, 3H), 1.57 t ($^3J_{H,H}$=7.3 Hz, CH$_3$, 3H), −0.12 d ($^3J_{F,H}$=14.4 Hz, BCH$_3$, 3H).

$^1$H-NMR: δ, ppm=9.03 br. s (CH, 1H), 7.75 t ($^3J_{H,H} \approx {}^4J_{H,H}$≈1.8 Hz, CH, 1H), 7.68 t ($^3J_{H,H} \approx {}^4J_{H,H}$≈1.7 Hz, CH, 1H), 4.40 q ($^3J_{H,H}$=7.3 Hz, CH$_2$, 2H), 4.05 s (CH$_3$, 3H), 1.57 t ($^3J_{H,H}$=7.3 Hz, CH$_3$, 3H), −0.12 d,q ($^3J_{F,H}$=14.4 Hz, $^2J_{B,H}$≈4.3 Hz, BCH$_3$, 3H).

$^{13}$C{$^1$H}-NMR: δ, ppm=136.4 s (EMIM, 1C), 134.0 q,q ($^1J_{C,B}$=62 Hz, $^2J_{F,C}$=39 Hz, 2CN, 2C), 124.0 s (EMIM, 1C), 122.3 s (EMIM, 1C), 45.0 s (EMIM, 1C), 35.9 s (EMIM, 1C), 14.8 s (EMIM, 1C), 8.1 m (BCH$_3$, 1C).

Example 9

1-Ethyl-3-methylimiazolium methylcyanodifluoroborate—EMIM [CH$_3$BF$_2$(CN)]

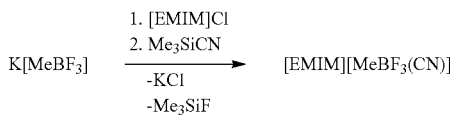

A suspension of potassium methyltrifluoroborate (5.22 g, 42.81 mmol) in H$_2$O (10 ml) is added to an aqueous solution of [EMIM]Cl (6.5 g, 44.34 mmol) and mixed, and the solution is evaporated to dryness. The residue is taken up in dichloromethane (20 ml), undissolved precipitate is separated off, and the CH$_2$Cl$_2$ is removed in vacuo. The ionic liquid [EMIM]-[CH$_3$BF$_3$] obtained (7.93 g, 40.87 mmol) is dissolved in acetonitrile (15 ml), and trimethylsilyl cyanide (5.45 ml, 40.87 mmol) is added. The reaction mixture is stirred at room temperature for 3 days. All volatile constituents are subsequently removed in vacuo.

The yield of [EMIM][CH$_3$BF$_2$(CN)] is 8.2 g (40.79 mmol).

(The purity is about 70%; the product contains about 22% of [EMIM][MeBF$_3$]$^-$ and 8% of further impurities.)

NMR data of the [CH$_3$BF$_2$(CN)]$^-$ anion (70%):

$^{11}$B{$^1$H}-NMR: δ, ppm=2.5 t ($^1J_{F,B}$=62.3 Hz).

$^{11}$B-NMR: δ, ppm=2.5 t,q ($^1J_{F,B}$=62.3 Hz, $^2J_{B,H}$=2.6 Hz).

$^{19}$F-NMR: δ, ppm=−147.7 t,q ($^3J_{F,H}$=10.4 Hz, 3H).

$^1$H{$^{11}$B}-NMR: δ, ppm=−0.32 t ($^3J_{F,H}$=11.8 Hz, CH$_3$, 3H).

$^1$H-NMR: δ, ppm=−0.32 br. t ($^3J_{F,H}$=11.8 Hz, CH$_3$, 3H).

NMR data of the [CH$_3$BF$_3$]$^-$ anion (22%):

$^{11}$B{$^1$H}-NMR: δ, ppm=5.3 q ($^1J_{F,B}$=62.1 Hz).

$^{11}$B-NMR: δ, ppm=5.3 q,q ($^1J_{F,B}$=62.1 Hz, $^2J_{B,H}$=~3 Hz).

$^{19}$F-NMR: δ, ppm=−132.9 q,q ($^1J_{F,B}$=61.4 Hz, $^3J_{F,H}$=5.1 Hz, 3F).

$^1$H{$^{11}$B}-NMR: δ, ppm=−0.44 q ($^3J_{F,H}$=8.2 Hz, CH$_3$, 3H).

$^1$H-NMR: δ, ppm=−0.44 br. q ($^3J_{F,H}$=8.2 Hz, CH$_3$, 3H).

NMR data of the [EMIM]$^+$ cation:

$^1$H{$^{11}$B}-NMR: δ, ppm=9.25 s (CH, 1H), 7.78 m (CH, 1H), 7.70 m (CH, 1H), 4.38 q ($^3J_{H,H}$=7.4 Hz, CH$_2$, 2H), 4.03 s (CH$_3$, 3H), 1.54 t ($^3J_{H,H}$=7.3 Hz, CH$_3$, 3H).

$^1$H-NMR: δ, ppm=9.25 s (CH, 1H), 7.78 m (CH, 1H), 7.70 m (CH, 1H), 4.38 q ($^3J_{H,H}$=7.4 Hz, CH$_2$, 2H), 4.03 s (CH$_3$, 3H), 1.54 t ($^3J_{H,H}$=7.3 Hz, CH$_3$, 3H).

Raman spectrum [EMIM][MeBF$_2$(CN)]: $\tilde{\nu}$ (CN)=2189 cm$^{-1}$

Example 10

1-Ethyl-3-methylimidazolium tricyanomethylborate—[EMIM][CH$_3$B(CN)$_3$]

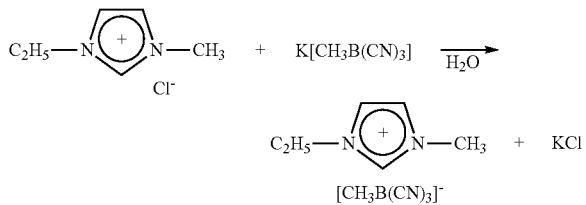

A solution of ethylmethylimidazolium chloride, [EMIM]Cl, (4.50 g, 30.69 mmol), in bidistilled water (10 ml) and a solution of potassium methyltricyanoborate (4.33 g, 30.28 mmol) in bidistilled water (5 ml) are combined and mixed. The reaction solution is extracted with CH$_2$Cl$_2$ (4×50 ml). The combined dichloromethane phases are dried using MgSO$_4$, and the solvent is removed using a rotary evaporator. The ionic liquid obtained is dried in vacuo.

The yield of 1-ethyl-3-methylimidazolium tricyanomethylborate is 6.35 g (29.53 mmol).

The NMR spectra of EMIM [CH$_3$B(CN)$_3$]:

$^{11}$B{$^1$H}-NMR: δ, ppm=−32.5 s.

$^{11}$B-NMR: δ, ppm=−32.5 q ($^2J_{B,H}$=4.2 Hz).

$^1$H{$^{11}$B}-NMR: δ, ppm=8.91 br. s (CH, 1H), 7.68 t ($^3J_{H,H} \approx {}^4J_{H,H}$≈1.7 Hz, CH, 1H), 7.62 t ($^3J_{H,H} \approx {}^4J_{H,H}$≈1.7 Hz, CH, 1H), 4.36 q ($^3J_{H,H}$=7.3 Hz, CH$_2$, 2H), 4.02 s (CH$_3$, 3H), 1.57 t ($^3J_{H,H}$=7.3 Hz, CH$_3$, 3H), −0.03 s (BCH$_3$, 3H).

$^1$H-NMR: δ, ppm=8.91 br. s (CH, 1H), 7.68 t ($^3J_{H,H} \approx {}^4J_{H,H}$≈1.7 Hz, CH, 1H), 7.62 t ($^3J_{H,H} \approx {}^4J_{H,H}$≈1.7 Hz, CH, 1H), 4.36 q ($^3J_{H,H}$=7.3 Hz, CH$_2$, 2H), 4.02 s (CH$_3$, 3H), 1.57 t ($^3J_{H,H}$=7.3 Hz, CH$_3$, 3H), −0.03 q ($^2J_{B,H}$=4.4 Hz, BCH$_3$, 3H).

$^{13}$C{$^1$H}-NMR: δ, ppm=131.5 q ($^1J_{C,B}$=63.9 Hz, BCN, 3C), 136.7 s (1C), 124.5 s (1C), 122.9 s (1C), 45.6 s (1C), 36.5 s (1C), 15.4 s (1C), 4.7 q ($^1J_{C,B}$=45 Hz, BCH$_3$, 1C).

Analysis:

Water content (Karl-Fischer titration): 37 ppm.

Halogen impurities (ion chromatography): Cl$^-$=97 ppm.

Dynamic viscosity:

| °C. | mPa · s |
|---|---|
| 20 | 21.1 |
| 30 | 14.9 |
| 40 | 11.0 |
| 50 | 8.5 |
| 60 | 6.8 |
| 70 | 5.5 |
| 80 | 4.6 |

Example 11

1-Butyl-3-methylimidazolium methyltricyanoborate—BMIM[CH$_3$B(CN)$_3$]

BMIMCl+K[CH$_3$B(CN)$_3$]→BMIM[CH$_3$B(CN)$_3$]+KCl

A suspension of potassium methyltricyanoborate (5.0 g, 34.96 mmol) and 1-butyl-3-methylimidazolium chloride (6.72 g; 38.45 mmol) in deionised $H_2O$ (10 ml) is prepared and $CH_2Cl_2$ (50 mL) is added. The aqueous phase is removed and the organic phase is washed with deionised $H_2O$ (5×1 mL) and dried with magnesium sulfate. After filtration, the organic solvent $CH_2Cl_2$ is removed under reduced pressure. The resulting liquid is dried in vacuum at 50° C. for three days.

The Yield of 1-butyl-3-methylimidazolium methyltricyanoborate is 6.9 g (28.38 mmol).

$^{11}B\{^1H\}$-NMR: δ, ppm=−33.5 (s).
$^{11}B$-NMR: δ, ppm=−33.5 (broad s).
$^1H\{^{11}B\}$-NMR: δ, ppm=8.98 (dd, $^4J_{H,H}$≈1.5 Hz, CH, 1H), 7.73 (dd, $^3J_{H,H}$≈$^4J_{H,H}$≈1.6 Hz, CH, 1H), 7.68 (dd, $^3J_{H,H}$≈$^4J_{H,H}$≈1.5 Hz CH, 1H), 4.35 (t, $^3J_{H,H}$=7.28 Hz, $CH_2$, 2H), 4.05 (s, $CH_3$, 3H), 1.93 (m, $CH_2$, 2 H), 1.39 (m, $CH_2$, 2H), 0.95 (t, $^3J_{H,H}$=7.40 Hz, $CH_3$, 3H), −0.05 (s, $BCH_3$, 3H).
$^1H$-NMR: δ, ppm=8.98 (dd, $^4J_{H,H}$≈1.5 Hz, CH, 1H), 7.73 (dd, $^3J_{H,H}$≈$^4J_{H,H}$≈1.6 Hz, CH, 1H), 7.68 (dd, $^3J_{H,H}$≈$^4J_{H,H}$≈1.5 Hz CH, 1H), 4.35 (t, $^3J_{H,H}$=7.28 Hz, $CH_2$, 2H), 4.05 (s, $CH_3$, 3H), 1.93 (m, $CH_2$, 2 H), 1.39 (m, $CH_2$, 2H), 0.95 (t, $^3J_{H,H}$=7.40 Hz, $CH_3$, 3H), −0.05 (deformed q, $^2J_{B,H}$≈4 Hz, $BCH_3$, 3H).
$^{13}C\{^1H\}$-NMR: δ, ppm=137.3 (s, CH, 1C), 131.4 (q, $^1J_{C,B}$=63.3 Hz, CN, 3C), 124.7 (s, CH, 1C), 123.4 (s, CH, 1C), 50.2 (s, $CH_2$, 1C), 36.7 (s, $CH_3$, 1C), 32.6 (s, $CH_2$, 1C), 19.9 (s, $CH_2$, 1C), 13.6 (s, $CH_3$, 1C), 4.6 (q, $^1J_{C,B}$=44.3 Hz, $BCH_3$, 1C).

Elemental analysis:
Calc.: C, 59.04; H, 7.84; N, 28.69.
Found: C, 58.53; H, 7.64; N, 29.40.
Dynamic viscosity:

| ° C. | mPa · s |
|---|---|
| 20 | 39.2 |
| 40 | 17.4 |
| 60 | 9.6 |
| 80 | 6.1 |

Decomposition's temperature: 240° C.

Example 12

Triethylsulfonium methyltricyanoborate—$[(C_2H_5)_3S][CH_3B(CN)_3]$

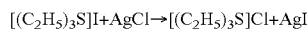

A mixture of triethylsulfonium iodide, $[(C_2H_5)_3S]I$ (8.6 g, 34.96 mmol), and AgCl (10.0 g, 69.78 mmol) in deionised water (50 mL) is stirred in the dark for four hours. The suspension is then filtered and the filtrate is treated with $K[CH_3B(CN)_3]$ (5.0 g, 34.96 mmol) thus forming two phases. The mixture is extracted with dichloromethane (3×25 mL) and the combined organic phases are washed with deionised water (5×25 mL) and dried over magnesium sulfate. After filtration, the organic solvent $CH_2Cl_2$ is removed under reduced pressure. The resulting liquid is dried in vacuum at 50° C. for three days.

The yield of triethylsulfonium methyltricyanoborate is 5.8 g (25.99 mmol).

$^{11}B\{^1H\}$-NMR: δ, ppm=−33.5 (s).
$^{11}B$-NMR: δ, ppm=−33.5 (s, broad).
$^1H\{^{11}B\}$-NMR: δ, ppm=3.61 (q, $^3J_{H,H}$=7.4 Hz, $SCH_2$, 6H), 1.65 (t, $^3J_{H,H}$=7.4 Hz, $CH_3$, 3H), 0.09 (s, $BCH_3$, 3H).
$^1H$-NMR: δ, ppm=3.61 (q, $^3J_{H,H}$=7.4 Hz, $SCH_2$, 6H), 1.65 (t, $^3J_{H,H}$=7.4 Hz, $CH_3$, 3H), 0.09 (m, $BCH_3$, 3H).
$^{13}C\{^1H\}$-NMR: δ, ppm=131.4 (q, $^1J_{C,B}$=63.3 Hz, CN, 3C), 33.3 (s, 3C), 9.0 (s, 3C), 4.4 (q, $^1J_{C,B}$=44.9 Hz, $BCH_3$, 1C).

Elemental analysis:
calculated: C, 53.82; H, 8.13; N, 18.83; S 14.37.
found: C, 53.13; H, 8.20; N, 18.9; S, 14.07.
Dynamic viscosity:

| ° C. | mPa · s |
|---|---|
| 20 | 22.8 |
| 40 | 12.0 |
| 60 | 7.3 |
| 80 | 4.9 |

Decomposition's temperature: 160° C.

Example 13

Methyldiphenylsulfonium methyltricyanoborate—$[(CH_3)(C_6H_5)_2S][CH_3B(CN)_3]$

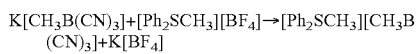

A solution of methyldiphenylsulfonium tetrafluoroborate, $[(CH_3)(C_6H_5)_2S][BF_4]$, (4.50 g, 30.69 mmol), 100 mg, 0.347 mmol in acetonitrile (2 ml) and a solution of potassium methyltricyanoborate (50 mg, 0.347 mmol in acetonitril (2 ml) are combined and mixed. The salt potassium tetrafluoroborate is filtered at 0° C. and all volatile components are removed under reduced pressure resulting in the compound methyldiphenylsulfonium methyltricyanoborate.

The yield of methyldiphenylsulfonium methyltricyanoborate is 101 mg (0.33 mmol). The product contains 2% tetrafluoroborate.

$^{11}B\{^1H\}$-NMR: δ, ppm=−33.5 (s).
$^{11}B$-NMR: δ, ppm=−33.5 (s, broad).
$^1H\{^{11}B\}$-NMR: δ, ppm=8.10 (m, $C_{arom}H$, 4H), 7.84 (m, $C_{arom}H$, 2H), 7.78 (m, $C_{arom}$ H, 4H), 3.97 (5, $CH_3$, 3H), −0.02 (5, $BCH_3$, 3H).
$^1H$-NMR: δ, ppm=8.10 (m, $C_{arom}H$, 4H), 7.84 (m, $C_{arom}H$, 2H), 7.78 (m, $C_{arom}$ H, 4H), 3.97 (s, $CH_3$, 3H), −0.02 (verzerrtes q, $^2J_{B,H}$~5 Hz, $BCH_3$, 3H).
$^{13}C\{^1H\}$-NMR: δ, ppm=134.7 (s, $C_{arom}$, 2C), 131.6 (s, $C_{arom}$, 4C), 131.1 (q, $^1J_{C,B}$=63 Hz, CN, 3C), 130.4 (s, $C_{arom}$, 4C), 127.4 (s, $C_{arom}$, 2C), 27.6 (s, $CH_3$, 1C), 4.3 (q, $^1J_{C,B}$=44 Hz, $BCH_3$, 1C).

Example 14

Triphenylsulfonium methyltricyanoborate—$[(C_6H_5)_3S][CH_3B(CN)_3]$

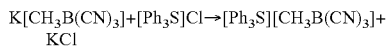

$K[CH_3B(CN)_3]$ (70 mg, 0.489 mmol) is added to a solution of triphenylsulfonium chloride, $[(C_6H_5)_3S]Cl$, (50 mg, 0.167 mmol) in 2 mL $CH_2Cl_2$. The suspension is vigorously stirred for 2 hours and filtered. The volatile components are removed under reduced pressure and the crystalline product triphenylsulfonium methyltricyanoborate is received.

The yield of triphenylsulfonium methyltricyanoborate is 57 mg (0.155 mmol).

$^{11}$B{$^1$H}-NMR: δ, ppm=−33.5 (s).
$^{11}$B-NMR: δ, ppm=−33.5 (q, $^2J_{B,H}$=4.4 Hz).
$^1$H{$^{11}$B}-NMR: δ, ppm=7.9 (m, $C_{arom}$H, 15H), −0.03 (s, BCH$_3$, 3H).
$^1$H-NMR: δ, ppm=7.9 (m, $C_{arom}$H, 15H), −0.03 (deformed q, $^2J_{B,H}$≈5 Hz, BCH$_3$, 3H).
$^{13}$C{$^1$H}-NMR: δ, ppm=135.7 (s, $C_{arom}$, 3C), 132.6 (s, $C_{arom}$, 6C), 132.2 (s, $C_{arom}$, 6C), 131.5 (q, $^1J_{C,B}$=64 Hz, CN, 3C), 125.9 (s, $C_{arom}$, 3C), 4.8 (q, $^1J_{C,B}$=45.0 Hz, BCH$_3$, 1C).

Example 15

Diphenyliodonium methyltricyanoborate—[(C$_6$H$_5$)$_2$I][CH$_3$B(CN)$_3$]

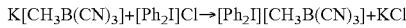

K[CH$_3$B(CN)$_3$] (50 mg, 0.157 mmol) is added to a suspension of diphenyliodonium chloride, [(C$_6$H$_5$)$_2$I]Cl, (50 mg, 0.157 mmol) in 2 mL CH$_2$Cl$_2$. The suspension is vigorously stirred for 2 hours and filtered. The volatile components are removed under reduced pressure and the crystalline product diphenyliodonium methyltricyanoborate is received.

The yield of diphenyliodonium methyltricyanoborate is 58 mg (0.150 mmol).

$^{11}$B{$^1$H}-NMR: δ, ppm=−33.5 (s).
$^{11}$B-NMR: δ, ppm=−33.5 (s, broad).
$^1$H{$^{11}$B}-NMR: δ, ppm=8.32 (m, $C_{arom}$H, 4H), 7.76 (m, $C_{arom}$H, 2H), 7.61 (m, $C_{arom}$H, 4H), −0.02 (s, BCH$_3$, 3H).
$^1$H-NMR: δ, ppm=8.32 (m, $C_{arom}$H, 4H), 7.76 (m, $C_{arom}$H, 2H), 7.61 (m, $C_{arom}$H, 4H), −0.02 (verzerrtes q, $^2J_{B,H}$~5 Hz, BCH$_3$, 3H).
$^{13}$C{$^1$H}-NMR: δ, ppm=136.3 (s, $C_{arom}$, 4C), 133.6 (s, $C_{arom}$, 2C), 133.2 (s, $C_{arom}$, 4C), 131.5 (q, $^1J_{C,B}$=64 Hz, CN, 3C), 115.7 (s, $C_{arom}$, 2C), 4.7 (q, $^1J_{C,B}$=45 Hz, BCH$_3$, 1C).

Example 16

2,4,6-Triphenylpyrylium methyltricyanoborate—TPP[CH$_3$B(CN)$_3$]

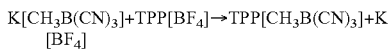

A solution of triphenylpyrylium tetrafluoroborate, [TPP][BF$_4$], (100 mg, 0.252 mmol), in acetonitrile (2 ml) and a solution of potassium methyltricyanoborate (36 mg, 0.252 mmol) in acetonitril (2 ml) are combined and mixed. The salt potassium tetrafluoroborate is filtered at 0° C. and all volatile components are removed under reduced pressure resulting in the solid compound 2,4,6-triphenylpyrylium methyltricyanoborate.

The yield of 2,4,6-triphenylpyrylium methyltricyanoborate is 95 mg (0.2298 mmol) containing 1% [BF$_4$]$^−$).

$^{11}$B{$^1$H}-NMR (CD$_3$CN): δ, ppm=−33.5 (s).
$^{11}$B-NMR (CD$_3$CN): δ, ppm=−33.5 (s).
$^1$H{$^{11}$B}-NMR: δ, ppm=8.69 (s, $C_{arom}$, 2H), 8.41 (m, $C_{arom}$, 4H), 8.29 (m, $C_{arom}$, 2H), 7.85 (m, $C_{arom}$, 3H), 7.76 (m, $C_{arom}$, 6H), −0.03 (s, BCH$_3$, 3H).
$^1$H-NMR: δ, ppm=8.69 (s, $C_{arom}$, 2H), 8.41 (m, $C_{arom}$, 4H), 8.29 (m, $C_{arom}$, 2H), 7.85 (m, $C_{arom}$, 3H), 7.76 (m, $C_{arom}$, 6H), −0.03 (verzerrtes q, $^2J_{B,H}$≈5 Hz, BCH$_3$, 3H).
$^{13}$C{$^1$H}-NMR: δ, ppm=6, 171.8 (s, $C_{arom}$), 167.4 (s, $C_{arom}$), 136.4 (s, $C_{arom}$), 136.3 (s, $C_{arom}$), 133.8 (s, $C_{arom}$), 131.7 (q, $^1J_{C,B}$=64 Hz, CN, 3C), 131.04 (s, $C_{arom}$), 131.02 (s, $C_{arom}$), 130.6 (s, $C_{arom}$), 129.9 (s, $C_{arom}$), 129.7 (s, $C_{arom}$), 116.7 (s, $C_{arom}$), 4.3 (q, $^1J_{C,B}$=45 Hz, BCH$_3$, 1C).

Example 17

Triphenylcarbenium methyltricyanoborate—[Ph$_3$C][CH$_3$B(CN)$_3$]

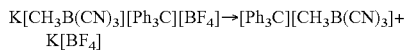

A solution of triphenylcarbenium (tritylium)tetrafluoroborate, [Ph$_3$C][BF$_4$], (100 mg, 0.303 mmol), in acetonitrile (2 ml) and a solution of potassium methyltricyanoborate (43 mg, 0.301 mmol) in acetonitril (2 ml) are combined and mixed. The salt potassium tetrafluoroborate is filtered at 0° C. and all volatile components are removed under reduced pressure resulting in the compound tritylium methyltricyanoborate.

The yield of triphenylcarbenium methyltricyanoborate is 102 mg (0.29 mmol) containing 1% [BF$_4$]$^−$ and 19% unknown boron species.

$^{11}$B{$^1$H}-NMR (CD$_3$CN): δ, ppm=−33.5 (s).
$^{11}$B-NMR (CD$_3$CN): δ, ppm=−33.5 (s).
$^1$H{$^{11}$B}-NMR: δ, ppm=8.25 (m, $C_{arom}$, 3H), 7.86 (m, $C_{arom}$, 6H), 7.69 (m, $C_{arom}$, 6H), 0.00 (s, BCH$_3$, 3H).
$^1$H-NMR: δ, ppm=8.25 (m, $C_{arom}$, 3H), 7.86 (m, $C_{arom}$, 6H), 7.69 (m, $C_{arom}$, 6H), 0.00 (m, BCH$_3$, 3H).

Example 18

1-Ethyl-3-methylimidazolium Vinyltricyanoborate—EMIM[H$_2$C═HCB(CN)$_3$]

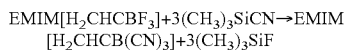

A mixture of trimethylsilylcyanide (86 mol %), fluorotrimethylsilane (4 mol %), chlorotrimethylsilane (3 mol %) and acetonitril (4 mol %) is added to 1-Ethyl-3-methylimidazolium vinyltrifluoroborate, EMIM[H$_2$C═HCBF$_3$], (1.48 g, 7.18 mmol) and stirred for 12 hours at room temperature. All volatile components are removed under reduced pressure.

The yield of EMIM[H$_2$C═HCB(CN)$_3$] is 1.55 g (6.82 mmol) containing 2% [H$_2$C═HCBF$_2$(CN)]$^−$ and 2.5% [H$_2$C═HCB(NC)(CN)$_2$]$^−$).

$^{11}$B{$^1$H}-NMR: δ, ppm=−31.4 (s).
$^{11}$B-NMR: δ, ppm=−31.4 (s, verbreitert).
$^1$H{$^{11}$B}-NMR: δ, ppm=8.89 (verbreitertes s, CH, 1H), 7.67 (dd, $^3J_{H,H}$≈$^4J_{H,H}$≈1.8 Hz, CH, 1H), 7.62 (dd, $^3J_{H,H}$≈$^4J_{H,H}$≈1.8 Hz, CH, 1H), 5.75 (dd, $J_{H,H}$=19.0 Hz, $J_{H,H}$=12.4 Hz, 1H), 5.40 (m, 2H), 4.35 (q, $J_{H,H}$=7.3 Hz, CH$_2$, 2H), 4.00 (s, CH$_3$, 3H), 1.55 (t, $^3J_{H,H}$=7.3 Hz, CH$_3$, 3H).
$^1$H-NMR: δ, ppm=8.89 (breites s, CH, 1H), 7.67 (dd, $^3J_{H,H}$≈$^4J_{H,H}$≈1.8 Hz, CH, 1H), 7.62 (dd, $^3J_{H,H}$≈$^4J_{H,H}$≈1.8 Hz, CH, 1H), 5.75 (dd, verbreitert, $J_{H,H}$=19.0 Hz, $J_{H,H}$=12.4 Hz, 1H), 5.40 (m, 2H), 4.35 (q, $^3J_{H,H}$=7.3 Hz, CH$_2$, 2H), 4.00 (s, CH$_3$, 3H), 1.55 (t, $^3J_{H,H}$=7.3 Hz, CH$_3$, 3H).
$^{13}$C{$^1$H}-NMR: δ, ppm=139.29 (q, $^1J_{C,B}$=55.3 Hz, BCH, 1C), 136.69 (s, 1C), 129.04 (q, $^1J_{C,B}$=63.7 Hz, BCN, 3C), 124.5 (s, 1C), 123.7 (s, 1C), 122.8 (s, 1C), 45.5 (s, 1C), 36.5 (s, 1C), 15.4 (s, 1C).

Example 19

Butylmethylpyrrolidinium tricyanomethylborate—[BMPL][CH$_3$B(CN)$_3$]

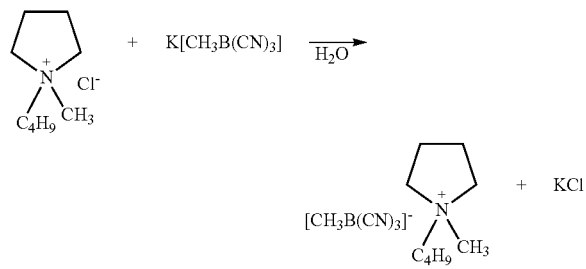

Butylmethylpyrrolidinium chloride, [BMPL]Cl, (190 mg, 1.07 mmol), and potassium methyltricyanoborate (168 mg, 1.18 mmol) are suspended in chloroform (5 ml) and stirred for one hour. The potassium chloride formed and excess potassium methyltricyanoborate are subsequently filtered off.

The filtrate is evaporated in vacuo, giving an ionic liquid. Yield: 243 mg (0.987 mmol).

The NMR spectra of BMPL [CH$_3$B(CN)$_3$]:
$^{11}$B{$^{1}$H}-NMR: δ, ppm=−32.5 s.
$^{11}$B-NMR: δ, ppm=−32.5 q ($^2J_{B,H}$=4.2 Hz).
$^{1}$H{$^{11}$B}-NMR: δ, ppm=3.75-3.67 m (CH$_2$, 4H), 3.56-3.52 m (CH$_2$, 2H), 3.25 (CH$_3$, 3H), 2.37-2.29 m (CH$_2$, 4H), 1.95-1.87 m (CH$_2$, 2H), 1.49-1.40 m (CH$_2$, 2H), 0.99 t ($^3J_{H,H}$=7.4 Hz, CH$_3$, 3H), −0.03 s (BCH$_3$, 3H).
$^{1}$H-NMR: δ, ppm=3.75-3.67 m (CH$_2$, 4H), 3.56-3.52 m (CH$_2$, 2H), 3.25 s (CH$_3$, 3H), 2.37-2.29 m (CH$_2$, 4H), 1.95-1.87 m (CH$_2$, 2H), 1.49-1.40 m (CH$_2$, 2H), 0.99 t ($^3J_{H,H}$=7.4 Hz, CH$_3$, 3H), −0.03 q ($^2J_{B,H}$=4.4 Hz, BCH$_3$, 3H).
$^{13}$C{$^{1}$H}-NMR: δ, ppm=131.5 q ($^1J_{C,B}$=63.9 Hz, BCN, 3C), 65.3 t ($^1J_{N,C}$=3.2 Hz, NCH$_2$, 2C), 65.1 t ($^1J_{N,C}$=2.9 Hz, NCH$_2$, 1C), 49.1 t ($^1J_{N,C}$=4.0 Hz, NCH$_3$, 1C), 26.3 s (CH$_2$, 1C), 22.4 s (1C), 20.4 t ($^2J_{N,C}$=1.4 Hz, NCH$_2$CH$_2$, 1C), 13.8 s (CH$_3$, 1C), 4.7 q ($^1J_{C,B}$=45 Hz, BCH$_3$, 1C).

Example 20

Tetrabutylammonium tricyanomethylborate—[TBA][CH$_3$B(CN)$_3$]

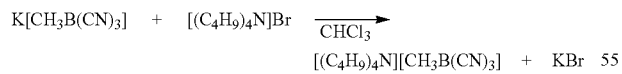

Tetrabutylammonium bromide, [TBA]Br, (200 mg, 0.620 mmol), and potassium methyltricyanoborate (98 mg, 0.685 mmol) are suspended in chloroform (5 ml) and stirred for one hour. The potassium chloride formed and excess potassium methyltricyanoborate are subsequently filtered off, and the filtrate is evaporated in vacuo. A slightly yellow solid is obtained.

The yield of tetrabutylammonium tricyanomethylborate is 211 mg (0.609 mmol), corresponding to 98%, based on the [TBA]Br employed.

The NMR spectra of TBA [CH$_3$B(CN)$_3$]:
$^{11}$B{$^{1}$H}-NMR: δ, ppm=−32.5 s.
$^{11}$B-NMR: δ, ppm=−32.5 q ($^2J_{B,H}$=4.2 Hz, 1B).
$^{1}$H{$^{11}$B}-NMR: δ, ppm=3.43-3.38 m (CH$_2$, 8H), 1.85-1.77 m (CH$_2$, 8H), 1.48-1.39 m (CH$_2$, 8H), 0.98 t ($^3J_{H,H}$=7.4 Hz, CH$_3$, 12H), −0.02 s (BCH$_3$, 3H).
$^{1}$H-NMR: δ, ppm=3.43-3.38 m (CH$_2$, 8H), 1.85-1.77 m (CH$_2$, 8H), 1.48-1.39 m (CH$_2$, 8H), 0.98 t ($^3J_{H,H}$=7.4 Hz, CH$_3$, 12H), −0.02 q ($^2J_{B,H}$=4.4 Hz, BCH$_3$, 3H).
$^{13}$C{$^{1}$H}-NMR: δ, ppm=131.5 q ($^1J_{C,B}$=63.3 Hz, BCN, 3C), 59.4 s (4C), 24.4 s (CH$_2$, 4C), 20.4 s (CH$_2$, 4C), 13.9 s (CH$_3$, 4C), 4.8 q ($^1J_{C,B}$=45 Hz, BCH$_3$, 1C).

Example 21

Tetraphenylphosphonium diethyldicyanoborate—[PPh$_4$][(C$_2$H$_5$)$_2$B(CN)$_2$]

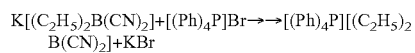

Potassium fluoride, KF (1.0 g, 17.24 mmol), is suspended in acetonitrile (4 ml). (C$_2$H$_5$)$_2$BOCH$_3$ (2.26 ml, 1.72 g, 17.24 mmol) and trimethylsilyl cyanide (5.0 ml, 37.49 mmol) are added at 0° C. The reaction mixture is stirred overnight at room temperature, and the yellow suspension obtained is then taken up in aqueous H$_2$O$_2$ (20%, 15 ml). Tetraphenylphosphonium bromide, [PPh$_4$]Br (7.5 g, 17.88 mmol), is added to the solution under stirring, and the reaction mixture is extracted with CH$_2$Cl$_2$ (2×20 ml) after 30 min stirring. The combined dichloromethane phases are dried using MgSO$_4$ and evaporated to dryness. The residue obtained is dissolved in acetone (5 ml) and precipitated by addition of Et$_2$O (15 ml) and subsequently filtered.

The yield of solid tetraphenylphosphonium diethyldicyanoborate is 3.52 g (7.64 mmol).

The NMR spectra of [PPh$_4$][(C$_2$H$_5$)$_2$B(CN)$_2$]:
$^{11}$B-NMR: δ, ppm=−22.1 s.
$^{1}$H{$^{11}$B}-NMR: δ, ppm=8.05-7.98 m (p-H, 4Ph, 4H), 7.90-7.83 m (o- and m-H, 4Ph, 16H), 0.85 t ($^3J_{H,H}$=7.7 Hz, 2CH$_2$, 4H), 0.23 q ($^3J_{H,H}$=7.6 Hz, 2CH$_3$, 6H).
$^{1}$H-NMR: δ, ppm=8.05-7.98 m (p-H, 4Ph, 4H), 7.90-7.83 m (o- and m-H, 4Ph, 16H), 0.85 br. t ($^3J_{H,H}$=7.7 Hz, 2CH$_2$, 4H), 0.23 br. q ($^3J_{H,H}$=7.6 Hz, 2CH$_3$, 6H).
$^{13}$C{$^{1}$H}-NMR: δ, ppm=138.4 q ($^1J_{C,B}$=53.1 Hz, 2CN, 2C), 136.4 d ($^4J_{P,C}$=3.1 Hz, 4C), 135.7 d ($^2J_{P,C}$=10.3 Hz, 8C), 131.4 d ($^3J_{P,C}$=12.8 Hz, 8C), 119.0 d ($^1J_{P,C}$=89.6 Hz, 4C), 15.0 q ($^1J_{C,B}$=46.8 Hz, 2CH$_2$, 2C), 12.3 s (2CH$_3$, 2C).
$^{13}$C-NMR (only [(C$_2$H$_5$)$_2$B(CN)$_2$] anion): δ, ppm=138.4 q ($^1J_{C,B}$=53.1 Hz, 2CN, 2C), 15.0 t,q ($^1J_{H,C}$=113.7 Hz, $^1J_{C,B}$=46.8 Hz, 2CH$_2$, 2C), 12.3 q,t ($^1J_{H,C}$=122.9 Hz, $^2J_{H,C}$=4.2 Hz, 2CH$_3$, 2C).
MALDI-MS m/e [C$_6$H$_{10}$BN$_2$]$^-$:
calculated: 120 (24%), 121 (100%), 122 (7%).
found: 120 (26%), 121 (100%), 122 (10%).
Raman spectrum: ν (CN)=2185 cm$^{-1}$
Melting point (DSC, onset): 116° C.
Decomposition (DSC, onset): 336° C.

Example 22

1-Ethyl-3-methylimidazolium vinyldicyanoisocyanoborate—[EMIM][(CH$_2$=CH)B(CN)$_2$(NC)]

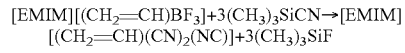

Trimethylsilyl cyanide (15 ml, 112.48 mmol) is condensed at −196° C. into a reaction vessel filled with 1-ethyl-3-methylimidazolium vinyltrifluoroborate, [EMIM][(CH$_2$=CH)BF$_3$] (0.5 g, 2.42 mmol), and the mixture is warmed to room temperature. The solution obtained is stirred overnight, then warmed at 65° C. for three hours, at 80° C. for two hours and finally at 90° C. for four hours. The excess trimethylsilyl cyanide is subsequently distilled off (recovered) as a mixture with trimethylfluorosilane formed and employed for further reactions. A colorless ionic liquid is isolated.

The yield of ethylmethylimidazolium vinyldicyanoisocyanoborate, [EMIM]-[(CH$_2$=CH)B(CN)$_2$(NC)], (93% purity), is 0.52 g (2.41 mmol). The liquid contains about 3% of [EMIM][(CH$_2$=CH)B(CN)$_3$], 3% of [EMIM][(CH$_2$=CH)B(CN)$_2$F] and about 1% of [EMIM][B(CN)$_2$F$_2$].

NMR data of the [(CH$_2$=CH)B(CN)$_2$(NC)]$^-$ anion:
$^{11}$B{$^1$H}-NMR: δ, ppm=−23.0 s.
$^{11}$B-NMR: δ, ppm=−23.0 s.
$^1$H{$^{11}$B}-NMR: δ, ppm=5.89-5.71 m (CH$_2$=CH, 1H), 5.45-5.28 m (CH$_2$=CH, 2H).
$^1$H-NMR: δ, ppm=5.89-5.71 br. m (CH$_2$=CH, 1H), 5.45-5.28 br. m (CH$_2$=CH, 2H).
$^{13}$C{$^1$H}-NMR: δ, ppm=170.0 s (BNC, 1C), 141.3 q ($^1J_{C,B}$=59.0 Hz, BCH=CH$_2$, 1C), 129.8 q ($^1J_{C,B}$=67.8 Hz, BCN, 2C), 122.6 s (BCH=CH$_2$, 1C).

NMR data of the [(CH$_2$=CH)B(CN)$_3$]$^-$ anion:
$^{11}$B{$^1$H}-NMR: δ, ppm=−30.4 s.
$^{11}$B-NMR: δ, ppm=−30.4 s.

NMR data of the [(CH$_2$=CH)B(CN)$_2$F]$^-$ anion:
$^{11}$B{$^1$H}-NMR: δ, ppm=−9.2 d ($^1J_{F,B}$=54.6 Hz).
$^{11}$B-NMR: δ, ppm=−9.2 d ($^1J_{F,B}$=54.6 Hz).
$^{19}$F-NMR: δ, ppm=−132.9 q ($^1J_{F,B}$=51.9 Hz).

NMR data of the [BF$_2$(CN)$_2$]$^-$ anion:
$^{11}$B{$^1$H}-NMR: δ, ppm=−7.3 t ($^1J_{F,B}$=41.2 Hz).
$^{11}$B-NMR: δ, ppm=−7.3 t ($^1J_{F,B}$=41.2 Hz).

NMR data of the [EMIM]$^+$ cation:
$^1$H{$^{11}$B}-NMR: δ, ppm=8.91 br. s (CH, 1H), 7.68 t ($^3J_{H,H}$≈$^4J_{H,H}$≈1.7 Hz, CH, 1H), 7.62 t ($^3J_{H,H}$≈$^4J_{H,H}$≈1.7 Hz, CH, 1H), 4.36 q ($^3J_{H,H}$=7.3 Hz, CH$_2$, 2H), 4.02 s (CH$_3$, 3H), 1.57 t ($^3J_{H,H}$=7.3 Hz, CH$_3$, 3H).
$^1$H-NMR: δ, ppm=8.91 br. s (CH, 1H), 7.68 t ($^3J_{H,H}$≈$^4J_{H,H}$≈1.7 Hz, CH, 1H), 7.62 t ($^3J_{H,H}$≈$^4J_{H,H}$≈1.7 Hz, CH, 1H), 4.36 q ($^3J_{H,H}$=7.3 Hz, CH$_2$, 2H), 4.02 s (CH$_3$, 3H), 1.57 t ($^3J_{H,H}$=7.3 Hz, CH$_3$, 3H).
$^{13}$C{$^1$H}-NMR: δ, ppm=136.7 s (1C), 124.5 s (1C), 122.9 s (1C), 45.6 s (1C), 36.5 s (1C), 15.4 s (1C).

Example 23

Potassium methyldicyanofluoroborate—K[CH$_3$BF(CN)$_2$]

A)

Potassium methyltrifluoroborate (3.00 g, 24.6 mmol) is suspended in trimethylsilyl cyanide (40.0 ml, 300.0 mmol) and stirred for 3 days at room temperature. After 3 days, the reaction mixture is stirred for 1 hour at 60° C. and 2 hours at 70° C. until the reaction mixture is clear. All volatile constituents are removed in vacuo. The unreacted trimethylsilyl cyanide and trimethylfluorosilane can be employed for further reactions. The residue is dissolved in acetone (30 ml) and filtered. CHCl$_3$ (100 ml) is added to the organic phase and K[CH$_3$BF(CN)$_2$] precipitates (batch I). Said precipitate is dried in vacuo. The organic solvent of the filtrate is distilled in vacuo until 5 ml are received and 50 ml CHCl$_3$ are added. K[CH$_3$BF(CN)$_2$] precipitates (batch II).

Batch I: 2.3 g (16.9 mmol) without by-product as described in Example 1A. The spectroscopic data correspond to those from Example 1A.

Batch II: 0.53 g of a mixture of K[CH$_3$BF(CN)$_2$] (82%) and K[CH$_3$B(NC)(CN)$_2$] (17%) and other impurities (1%).

B)

Potassium methyltrifluoroborate (8.00 g, 65.6 mmol) is suspended in trimethylsilyl cyanide (120.0 ml, 900.0 mmol, 30 ml trimethylsilyl cyanide recovered from Example 22 and stirred 2 hours at 70° C. until the solution is nearly clear. All volatile constituents are removed in vacuo. The residue is dissolved in acetone (40 ml) and filtered. The filtrate is stirred and 400 ml CHCl$_3$ is added within 45 minutes. The precipitate of K[CH$_3$BF(CN)$_2$] is filtered and dried in vacuo (6.71 g (49.3 mmol)). The spectroscopic date correspond to those from Example 1A.

Example 24

1-Ethyl-3-methylimidazolium methyldicyanofluoroborate—EMIM [CH$_3$BF(CN)$_2$]

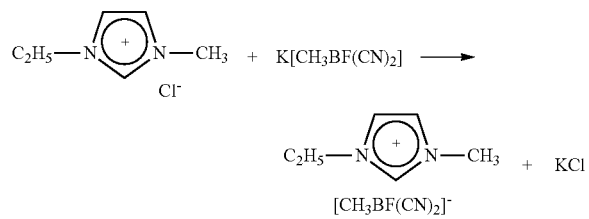

K[CH$_3$BF(CN)$_2$] (6.0 g, 44.1 mmol) and 1-ethyl-3-methylimidazolium chloride, [EMIM]Cl, (6.45 g, 44.0 mmol) are suspended in CH$_2$Cl$_2$ (50 mL) and stirred for 5 hours at room temperature. Magnesium sulfate is added (1 g) and the reaction mixture is stirred for 30 min and filtered. The precipitate is washed with 15 ml of CH$_2$Cl$_2$ and the organic phases are combined. All volatile compounds are removed in vacuo and the resulted ionic liquid is dried in vacuo for 2 days.

8.8 g (42.31 mmol) of EMIM [CH$_3$BF(CN)$_2$]

The spectroscopic data correspond to Example 8.

Dynamic viscosity:

| ° C. | mPa·s |
|---|---|
| 20 | 16.2 |
| 40 | 9.3 |
| 60 | 6.0 |
| 80 | 4.2 |

Example 25

1-Butyl-1-methylpyrrolidinium methyldicyanofluoroborate—[BMPL][CH$_3$BF(CN)$_2$]

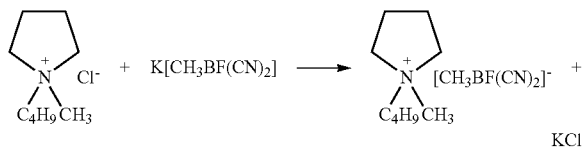

KCl

K[CH$_3$BF(CN)$_2$] (2.8 g, 20.6 mmol) and 1-butyl-1-methylpyrrolidinium Chloride, [BMPL]Cl (3.6 g, 20.5 mmol) are suspended in CH$_2$Cl$_2$ (25 mL) and stirred for 5 hours at room temperature. Magnesium sulfate is added (1 g) and the reaction mixture is stirred for 30 min and filtered. The precipitate is washed with 10 ml of CH$_2$Cl$_2$ and the organic phases are combined. All volatile compounds are removed in vacuo and the resulted ionic liquid is dried in vacuo for 2 days.

The yield of [BMPL][CH$_3$BF(CN)$_2$] is 4.3 g (18.0 mmol)

The NMR spectra of [BMPL][CH$_3$BF(CN)$_2$]:

$^{11}$B{$^1$H}-NMR: δ, ppm=−8.9 d ($^1J_{F,B}$=56.6 Hz).

$^{11}$B-NMR: δ, ppm=−8.9 br. d ($^1J_{F,B}$=56.5 Hz).

$^{19}$F-NMR: δ, ppm=−202.7 q,q ($^1J_{F,B}$=56.2 Hz, $^3J_{F,H}$=14.1 Hz, BF).

$^1$H{$^{11}$B}-NMR: δ, ppm=3.78-3.72 m (2CH$_2$, 4H), 3.75-3.60 m (CH$_2$, 2H), 3.27 s (CH$_3$, 3H), 2.35-2.30 m (2CH$_2$, 4H), 1.95-1.88 m (CH$_2$, 2H), 1.49-1.42 m (CH$_2$, 2H), 0.99 t ($^3J_{H,H}$=7.4 Hz, CH$_3$, 3H), −0.10 d ($^3J_{F,H}$=14.3 Hz, BCH$_3$, 3H).

$^1$H-NMR: δ, ppm=3.78-3.72 m (2CH$_2$, 4H), 3.75-3.60 m (CH$_2$, 2H), 3.27 s (CH$_3$, 3H), 2.35-2.30 m (2CH$_2$, 4H), 1.95-1.88 m (CH$_2$, 2H), 1.49-1.42 m (CH$_2$, 2H), 0.99 t ($^3J_{H,H}$=7.4 Hz, CH$_3$, 3H), −0.10 d ($^3J_{F,H}$=14.3 Hz, $^2J_{B,H}$≈4.6 Hz, BCH$_3$, 3H).

Dynamic viscosity:

| °C. | mPa·s |
|---|---|
| 20 | 46.0 |
| 40 | 22.8 |
| 60 | 13.1 |
| 80 | 8.4 |

Example 26

Potassium cyanomethyldicyanofluoroborate—K[NCCH$_2$BF(CN)$_2$]

A)

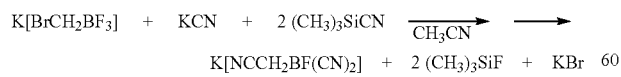

K[BrCH$_2$BF$_3$] (86 mg, 0.428 mmol) and KCN (200 mg, 3.07 mmol) are suspended in trimethylsilylcyanide (2.0 mL, 14.99 mmol). The reaction mixture is warmed to 60° C. over night, to 70° C. for 5 days, and to 80° C. for further 2 days. All volatile materials were removed under reduced pressure and the remaining solid material is extracted with acetone (5 mL). Extract is evaporated in vacuum yielding a light-brown solid.

The yield of potassium cyanomethyldicyanofluoroborate is 55 mg (0.34 mmol).

The spectroscopic data of K[NCCH$_2$BF(CN)$_2$]:

$^{11}$B{$^1$H}-NMR: δ, ppm=−10.5 d ($^1J_{F,B}$=54.2 Hz).

$^{11}$B-NMR: δ, ppm=−10.5 dt, ($^1J_{F,B}$=54.2 Hz, $^2J_{H,B}$=5.6 Hz).

$^{19}$F-NMR: δ, ppm=−205.6 qt ($^1J_{F,B}$=54.2 Hz, $^3J_{F,H}$=10.9 Hz, BF).

$^1$H{$^{11}$B}-NMR: δ, ppm=1.38 d ($^3J_{F,H}$=10.9 Hz, CH$_2$).

$^1$H-NMR: δ, ppm=1.38 dq ($^3J_{F,H}$=10.9 Hz, $^2J_{B,H}$≈6 Hz, CH$_2$).

$^{13}$C{$^1$H}-NMR: δ, ppm=130.45 qd ($^1J_{C,B}$=69.7 Hz, $^2J_{F,C}$=38.2 Hz, B-CN, 2C), 121.18 s (CH$_2$—CN, 1C), 10.37 qd ($^1J_{C,B}$=45.9 Hz, $^2J_{F,C}$=28.8 Hz, CH$_2$, 1C).

$^{13}$C-NMR: δ, ppm=130.45 dq ($^1J_{C,B}$=69.7 Hz, $^2J_{F,C}$=38.2 Hz, B-CN, 2C), 121.18 broad t ($^3J_{C,H}$≈7 Hz, CH$_2$—CN, 1C), 10.37 qd ($^1J_{C,B}$=45.9 Hz, $^2J_{F,C}$=28.8 Hz, CH$_2$, 1C).

MALDI-MS m/z [C$_4$H$_2$BFN$_3$]$^-$:

calculated: 122 (100%), 121 (25%), 123 (5%).

found: 122 (100%), 121 (26%), 123 (4%).

B)

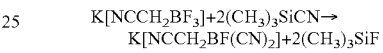

A mixture (50 mL) of trimethylsilylcyanide (86 mol %), fluorotrimethylsilane (4 mol %), chlorotrimethylsilane (3 mol %) and acetonitril (4 mol %) and 15 ml trimethylsilylcyanide (112.5 mmol) are added to potassium cyanomethyltrifluoroborate (5.7 g, 38.77 mmol) and the suspension is stirred for 2 hours at room temperature. All volatile components are removed under reduced pressure. These volatile components can be stored and be used for further syntheses. If the remaining product still contains [NCCH$_2$BF$_3$]$^-$ and [NCCH$_2$BF$_2$(CN)]$^-$, the mixture will be added to a mixture of [(CH$_3$)$_3$SiCN, (CH$_3$)$_3$SiF, (CH$_3$)$_3$SiCl, CH$_3$CN] and pure (CH$_3$)$_3$SiCN (15 mL, 112.5 mmol) and said suspension should be stirred for another two days. All volatile compounds are removed under reduced pressure again. The remainder is solved in acetone (10 mL) and 120 mL dichloromethane are added. The resulting precipitate of potassium cyanomethyldicyanofluoroborate is filtered and dried under reduced pressure.

The yield of potassium cyanomethyldicyanofluoroborate is 4.5 g (27.95 mmol).

Elemental analysis:

Calculated: C, 29.84; H, 1.25; N, 26.10.

Found: C, 30.08; H, 1.16; N, 26.06.

The spectroscopic data of the product correspond to those from Example 26A.

Example 27

1-Ethyl-3-methylimidazolium cyanomethyldicyanofluoroborate—EMIM[NCCH$_2$BF(CN)$_2$]

Dichloromethane (60 mL) is added to a mixture of potassium cyanomethyldicyanofluoroborate, K[NCCH$_2$BF(CN)$_2$], (4.3 g, 26.71 mmol) and 1-ethyl-3-methylimidazolium chloride (EMIMCl) (4.3 g, 29.32 mmol) in H$_2$O (deionised, 30 mL). The aqueous phase is removed and the organic phase is washed with deionised water (5×1 mL) and dried over magnesium sulfate. The sulfate is filtered and dichloromethane is removed under reduced pressure. The product is dried for three days at 50° C. in vacuum.

The yield of 1-ethyl-3-methylimidazolium cyanomethyldicyanofluoroborate is 4.9 g (21.03 mmol).

$^{11}$B{$^1$H}-NMR: δ, ppm=−11.4 (d, $^1J_{B,F}$=54.3 Hz).
$^{11}$B-NMR: δ, ppm=−11.4 (dt, $^1J_{B,F}$=54.3 Hz, $^2J_{B,H}$=5.7 Hz).
$^{19}$F-NMR: δ, ppm=−205.5 qt ($^1J_{F,B}$=54.3 Hz, $^3J_{F,H}$=11.0 Hz, BF).
$^1$H{$^{11}$B}-NMR: δ, ppm=8.90 (broad dd, $^4J_{H,H}$≈1.6 Hz, CH, 1H), 7.69 (dd, $^3J_{H,H}$≈$^4J_{H,H}$≈1.8 Hz, CH, 1H), 7.62 (dd, $^3J_{H,H}$≈$^4J_{H,H}$≈1.8 Hz, CH, 1H), 4.36 (q, $^3J_{H,H}$=7.4 Hz, CH$_2$, 2H), 4.02 (s, CH$_3$, 3H), 1.55 (t, $^3J_{H,H}$=7.3 Hz, CH$_3$, 3H), 1.40 (d, $^3J_{F,H}$=10.9 Hz, 2H, CH$_2$).
$^1$H-NMR: δ, ppm=8.90 (broad dd, $^4J_{H,H}$≈1.6 Hz, CH, 1H), 7.69 (dd, $^3J_{H,H}$≈$^4J_{H,H}$≈1.8 Hz, CH, 1H), 7.62 (dd, $^3J_{H,H}$≈$^4J_{H,H}$≈1.8 Hz, CH, 1H), 4.36 (q, $^3J_{H,H}$=7.4 Hz, CH$_2$, 2H), 4.02 (s, CH$_3$, 3H), 1.55 (t, $^3J_{H,H}$=7.3 Hz, CH$_3$, 3H), 1.40 (m, 2H, CH$_2$).
$^{13}$C{$^1$H}-NMR: δ, ppm=136.8 (s, 1C), 131.2 (qd, $^1J_{C,B}$=69 Hz, $^2J_{F,C}$=37 Hz, CN, 2C), 124.6 (s, 1C), 122.9 (s, 1C), 122.1 (broad, s, 1C, CH$_2$CN), 45.6 (s, 1C), 36.6 (s, 1C), 15.5 (s, 1C), 10.9 (qd, $^1J_{C,B}$=47 Hz, $^2J_{F,C}$≈28 Hz, 1C).

Elemental analysis:
calculated: C, 51.54; H, 5.62; Z 30.05.
found: C, 50.86; H, 5.79, N, 30.35.

Dynamic viscosity:

| ° C. | mPa · s |
| --- | --- |
| 20 | 27.0 |
| 40 | 13.5 |
| 60 | 8.0 |
| 80 | 5.3 |

Decomposition's temperature: 180° C.

Example 28

1-Ethyl-3-methylimidazolium Cyanomethylcyanodifluoroborate—[EMIM][NCCH$_2$BF$_2$(CN)]

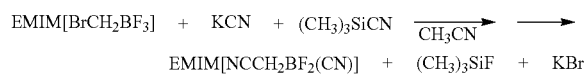

1-Ethyl-3-methylimidazolium cyanomethyltrifluoroborate, EMIM[BrCH$_2$BF$_3$], (120 mg, 0.439 mmol) and KCN (500 mg, 7.678 mmol) are added to stirred solution of trimethylsilyl cyanide in acetonitrile (2.5 mol/L, 2 mL, 5.0 mmol).

The reaction mixture is stirred at 75° C. (temperature in the oil-bath) for 24 hours and 4 days at 100° C. All volatiles are removed in vacuum and residue is dissolved in 2 mL of acetone. The non-soluble solids (presumably excess of KCN and KBr) are filtered off and the solution is evaporated in vacuum. The residue (oily material) is dissolved in acetone-D6 and analysed by means of mass- and NMR-spectroscopy. The NMR spectra confirm the formation of the [EMIM][NCCH$_2$BF$_2$(CN)] in 90% yield. The product contains of about 7% [EMIM][NCCH$_2$BF(CN)$_2$].

The spectroscopic data of the anion [NCCH$_2$BF$_2$(CN)]$^-$:
$^{11}$B{$^1$H}-NMR: δ, ppm=0.0 t ($^1J_{F,B}$=55.8 Hz).
$^{11}$B-NMR: δ, ppm=0.0 tt ($^1J_{F,B}$=55.8 Hz, $^2J_{H,H}$=6.1 Hz).
$^{19}$F-NMR: δ, ppm=−152.7 qt ($^1J_{F,B}$=55.8 Hz, $^3J_{F,H}$=8.0 Hz, BF).
$^1$H{$^{11}$B}-NMR: δ, ppm=1.13 t ($^3J_{F,H}$=8.2 Hz, CH$_2$).
$^1$H-NMR: δ, ppm=1.13 tq ($^3J_{F,H}$≈9 Hz, $^2J_{B,H}$≈6 Hz, CH$_2$).

NMR spectroscopic data of the cation [EMIM]+:
$^1$H-NMR: δ, ppm=9.00 s (CH, 1H), 7.72 broad s (CH, 1H), 7.65 broad s (CH, 1H), 4.37 q ($^3J_{H,H}$=7.3 Hz, CH$_2$, 2H), 4.03 (s, Me, 3H), 1.55 (t, $^3J_{H,H}$=7.3 Hz, Me, 3H).

MALDI-MS m/z [C$_3$H$_2$BF$_2$N$_2$]$^-$:
calculated: 115 (100%), 114 (25%), 116 (4%).
found: 115 (100%), 114 (23%), 116 (2%).

The NMR spectroscopic data of the anion [NCCH$_2$BF(CN)$_2$]$^-$, that is formed in approximately 7% yield are consistent with those of the anion as found for K[NCCH$_2$BF(CN)$_2$] in Example 26.

Example 29

Potassium diethyldicyanoborate—K[(C$_2$H$_5$)$_2$B(CN)$_2$]

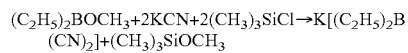

A suspension of potassium cyanide (35.0 g, 537.46 mmol) in acetonitril (100 mL) is prepared and (C$_2$H$_5$)$_2$BOCH$_3$ (25.0 mL, 192.31 mmol) is added (moderate exothermic reaction) and to said mixture, chlorotrimethylsilane (30.0 mL, 237.48 mmol) is added (exothermic reaction). The suspension is stirred for two days at 65° C. and filtered. The filtrate is washed with 100 mL acetonitrile. The content of acetonitrile is reduced within the combined organic phases through distillation under reduced pressure. After addition of pentane, the product potassium diethyldicyanoborate precipitates and is filtered and dried in vacuum.

The yield of potassium diethyldicyanoborate is 29.1 g (181.85 mmol).

$^{11}$B-NMR (CD$_3$CN): δ, ppm=−23.1 (s, broad).
$^{11}$B{$^1$H}-NMR (CD$_3$CN): δ, ppm=−23.1 (s).
$^1$H{$^{11}$B}-NMR (CD$_3$CN): δ, ppm=0.83 (t, broad, $^3J_{H,H}$=7.6 Hz, CH$_3$, 6H), 0.19 (q, $^3J_{H,H}$=7.6 Hz, CH$_2$, 4H).
$^1$H-NMR (CD$_3$CN): δ, ppm=0.83 (t, $^3J_{H,H}$=7.5 Hz, CH$_3$, 6H), 0.19 (q, broad, $^3J_{H,H}$=7.6 Hz, CH$_2$, 4H).
$^{13}$C{$^1$H}-NMR (CD$_3$CN): δ, ppm=139.3 (m, broad, CN, 2C), 14.6 (q, broad, $^1J_{C,B}$=48 Hz, CH$_2$, 2C), 12.0 (s, CH$_3$, 2C).

Example 30

1-Butyl-3-methylimidazolium diethyldicyanoborate—BMIM[C$_2$H$_5$)$_2$B(CN)$_2$]

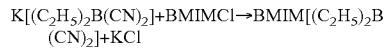

Dichloromethane (50 mL) is added to a mixture of potassium diethyldicyanoborate (6.0 g, 37.48 mmol) and 1-butyl-3-methylimidazolium chloride (BMIMCl) (6.5 g, 37.21 mmol) in H$_2$O (deionised, 20 mL). The aqueous phase is removed and the organic phase is washed with deionised water (5×1 mL) and dried over magnesium sulfate. The sulfate is filtered and dichloromethane is removed under reduced pressure. The product is dried for three days at 50° C. in vacuum.

The yield of 1-butyl-3-methylimidazolium diethyldicyanoborate is 8.9 g (34.21 mmol).

$^{11}$B{$^1$H}-NMR: δ, ppm=−23.1 (s).
$^{11}$B-NMR: δ, ppm=−23.1 (s, broad).

$^1$H{$^{11}$B}-NMR: δ, ppm=8.90 (dd, $^4J_{H,H}$≈1.7 Hz, CH, 1H), 7.63 (dd, $^3J_{H,H}$≈$^4J_{H,H}$≈1.7 Hz, CH, 1H), 7.57 (dd, $^3J_{H,H}$≈$^4J_{H,H}$≈1.7 Hz, CH, 1H), 4.22 (t, $^3J_{H,H}$=7.28 Hz, CH$_2$, 2H), 3.92 (s, CH$_3$, 3H), 1.80 (m, CH$_2$, 2 H), 1.26 (m, CH$_2$, 2H), 0.82 (t, $^3J_{H,H}$=7.40 Hz, CH$_3$, 3H), 0.83 (t, $^3J_{H,H}$=7.7 Hz, CH$_3$, 6H), 0.20 (q, $^3J_{H,H}$=7.7 Hz, CH$_2$, 4H).

$^1$H-NMR: δ, ppm=8.90 (dd, $^4J_{H,H}$≈1.7 Hz, CH, 1H), 7.63 (dd, $^3J_{H,H}$≈$^4J_{H,H}$≈1.7 Hz, CH, 1H), 7.57 (dd, $^3J_{H,H}$≈$^4J_{H,H}$≈1.7 Hz, CH, 1H), 4.22 (t, $^3J_{H,H}$=7.28 Hz, CH$_2$, 2H), 3.92 (s, CH$_3$, 3H), 1.80 (m, CH$_2$, 2 H), 1.26 (m, CH$_2$, 2H), 0.82 (t, $^3J_{H,H}$=7.40 Hz, CH$_3$, 3H), 0.83 (t, verbreitert, $^3J_{H,H}$=7.7 Hz, CH$_3$, 6H), 0.20 (q, broad, $^3J_{H,H}$=7.7 Hz, CH$_2$, 4H).

$^{13}$C{$^1$H}-NMR: δ, ppm=138.7 (q, $^1J_{C,B}$=53 Hz, CN, 2C), 137.2 (s, CH, 1C), 124.6 (s, CH, 1C), 123.3 (s, CH, 1C), 50.1 (s, CH$_2$, 1C), 36.6 (s, CH$_3$, 1C), 32.6 (s, CH$_2$, 1C), 19.8 (s, CH$_2$, 1C), 14.6 (q, $^1J_{C,B}$=44 Hz, BCH$_2$, 2C), 13.6 (s, CH$_3$, 1C), 12.1 (s, CH$_3$, 2C).

Elemental analysis:
calculated: C, 64.63; H, 9.68; N, 21.53.
found: C, 63.38; H, 9.82; N, 21.41.

Dynamic viscosity:

| °C. | mPa·s |
|---|---|
| 20 | 63.1 |
| 40 | 26.7 |
| 60 | 13.9 |
| 80 | 8.3 |

Decomposition's temperature: 190° C.

Example 31

N-Butyl-N-methylpyrrolidinium diethyldicyanoborate—BMPL[(C$_2$H$_5$)$_2$B(CN)$_2$]

K[(C$_2$H$_5$)$_2$B(CN)$_2$]+BMPLCl→BMPL[(C$_2$H$_5$)$_2$B(CN)$_2$]+KCl

Dichloromethane (50 mL) is added to a mixture of potassium diethyldicyanoborate (5.0 g, 31.23 mmol) and 1-butyl-1-methylpyrrolidinium chloride (BMPLCl) (5.5 g, 31.23 mmol) in H$_2$O (deionised, 50 mL). The aqueous phase is removed and the organic phase is washed with deionised water (5×1 mL) and dried over magnesium sulfate. The sulfate is filtered and dichloromethane is removed under reduced pressure. The product is dried for three days at 50° C. in vacuum.

The yield of N-butyl-N-methylpyrrolidinium diethyldicyanoborate is 7.5 g (28.49 mmol).

Elemental analysis:
calculated: C, 68.44; H, 11.49; N, 15.96.
found: C, 67.91; H, 11.57; N, 15.99.

$^{11}$B{$^1$H}-NMR: δ, ppm=−23.1 (s).
$^{11}$B-NMR: δ, ppm=−23.1 (s, broad).
$^1$H{$^{11}$B}-NMR: δ, ppm=3.7 (m, CH$_2$, 4H), 3.52 (m, CH$_2$, 2H), 3.22 (s, CH$_3$, 3H), 2.30 (m, 2CH$_2$, 4H), 1.87 (m, CH$_2$, 2H), 1.44 (m, CH$_2$, 2H), 0.84 (t, $^3J_{H,H}$=7.4 Hz, CH$_3$, 3H), 0.83 (t, $^3J_{H,H}$=7.5 Hz, CH$_3$, 6H), 0.22 (q, $^3J_{H,H}$=7.6 Hz, CH$_2$, 4H).

$^1$H-NMR: δ, ppm=3.7 (m, CH$_2$, 4H), 3.52 (m, CH$_2$, 2H), 3.22 (s, CH$_3$, 3H), 2.30 (m, CH$_2$, 4H), 1.87 (m, CH$_2$, 2H), 1.44 (m, CH$_2$, 2 H), 0.84 (t, broad, $^3J_{H,H}$=7.4 Hz, CH$_3$, 3H), 0.83 (t, $^3J_{H,H}$=7.5 Hz, CH$_3$, 6H), 0.22 (q, broad, $^3J_{H,H}$=7.6 Hz, CH$_2$, 4H).

$^{13}$C{$^1$H}-NMR: δ, ppm=138.7 (q, $^1J_{C,B}$=53 Hz, 2C, CN), 65.0 (s, CH$_2$, 2C), 64.8 (s, CH$_2$, 1C), 48.9 (s, CH$_3$, 1C), 26.2 (s, CH$_2$, 1C), 22.3 (s, CH$_2$, 2C), 20.3 (s, CH$_2$, 1C), 14.7 (q, $^1J_{C,B}$=45 Hz, CH$_2$, 2C), 13.8 (s, CH$_3$, 1C), 12.2 (s, CH$_3$, 2C).

Dynamic viscosity:

| °C. | mPa·s |
|---|---|
| 20 | 83.0 |
| 40 | 35.1 |
| 60 | 18.1 |
| 80 | 10.7 |

Decomposition's temperature: 190° C.

Example 32

N-Butylpyridinium diethyldicyanoborate—BPYR[(C$_2$H$_5$)$_2$B(CN)$_2$]

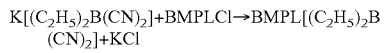

Dichloromethane (50 mL) is added to a mixture of potassium diethyldicyanoborate (6.0 g, 37.48 mmol) and N-butylpyridinium chloride (BPYRCl) (6.5 g, 37.86 mmol) in H$_2$O (deionised, 30 mL). The aqueous phase is removed and the organic phase is washed with deionised water (5×1 mL) and dried over magnesium sulfate. The sulfate is filtered and dichloromethane is removed under reduced pressure. The product is dried for three days at 50° C. in vacuum.

The yield of N-butylpyridinium diethyldicyanoborate is 9.2 g (35.77 mmol).

$^{11}$B{$^1$H}-NMR: δ, ppm=−23.1 (s).
$^{11}$B-NMR: δ, ppm=−23.1 (s, broad).
$^1$H{$^{11}$B}-NMR: δ, ppm=9.17 (m, C$_{arom}$H, 2H), 8.73 (m, C$_{arom}$H, 1H), 8.27 (m, C$_{arom}$H, 2H), 4.83 (t, $^3J_{H,H}$=7.5 Hz, CH$_2$, 2H), 2.10 (m, CH$_2$, 2H), 1.45 (m, CH$_2$, 2 H), 0.83 (t, $^3J_{H,H}$=7.30 Hz, CH$_3$, 3H), 0.83 (t, $^3J_{H,H}$=7.6 Hz, CH$_3$, 6H), 0.20 (q, $^3J_{H,H}$=7.6 Hz, CH$_2$, 4H).

$^1$H-NMR: δ, ppm=9.17 (m, C$_{arom}$H, 2H), 8.73 (m, C$_{arom}$H, 1H), 8.27 (m, C$_{arom}$H, 2H), 4.83 (t, $^3J_{H,H}$=7.5 Hz, CH$_2$, 2H), 2.10 (m, CH$_2$, 2H), 1.45 (m, CH$_2$, 2 H), 0.83 (t, $^3J_{H,H}$=7.30 Hz, CH$_3$, 3H), 0.83 (t, broad, $^3J_{H,H}$=7.7 Hz, CH$_3$, 6H), 0.20 (q, broad, $^3J_{H,H}$=7.7 Hz, CH$_2$, 4H).

$^{13}$C{$^1$H}-NMR: δ, ppm=146.6 (s, C$_{arom}$, 1C), 145.6 (t, $^1J_{N,C}$=8.0 Hz, NC$_{arom}$, 2C), 138.8 (q, $^1J_{C,B}$=54 Hz, CN, 2C), 129.3 (s, C$_{arom}$, 2C), 62.4 (s, CH$_2$, 1C), 33.9 (s, CH$_2$, 1C), 19.8 (s, CH$_2$, 1C), 14.6 (q, $^1J_{C,B}$=44 Hz, BCH$_2$, 2C), 13.6 (s, CH$_3$, 1C), 12.1 (s, CH$_3$, 2C).

Elemental analysis:
calculated: C, 70.05; H, 9.41; N, 16.34.
found: C, 69.22; H, 9.46; N, 16.50.

Dynamic viscosity:

| °C. | mPa·s |
|---|---|
| 20 | 78.5 |
| 40 | 31.4 |
| 60 | 15.7 |
| 80 | 9.3 |

Decomposition's temperature: 160° C.

Example A

The following electrolyte formulations are synthesized to demonstrate the application of electrolyte formulations according to the invention relative to electrolyte formulations of the prior art containing emim TCB in dye sensitized solar cells.

The electrolyte formulations are prepared through mixing of one or more of 1,3-dimethylimidazolium iodide (mmiml), 1-propyl-3-methylimidazolium iodide (pmiml), iodine, N-butylbenzimidazole (NBB) and guanidinium thiocyanate (guaSCN) and the corresponding ionic liquid as indicated such as emim TCB and EMIM [$(CH)_3BF(CN)_2$] (N-ethyl-3-methylimidazolium methylfluorodicyano-borate or bmpl TCB and BMPL [$(CH_3)BF(CN)_2$] (N-butyl-N-methylpyrrolidinium methylfluorodicyanoborate in weight % as listed below.

| Electrolyte 1 | weight % |
|---|---|
| $I_2$ | 1.6 |
| mmim I | 35 |
| guaSCN | 0.7 |
| NBB | 2.7 |
| emim TCB | 60 |
| total | 100 |

| Electrolyte 2 | weight % |
|---|---|
| $I_2$ | 1.6 |
| mmim I | 35 |
| guaSCN | 0.7 |
| NBB | 2.7 |
| emim [$(CH_3)BF(CN)_2$] | 60 |
| total | 100 |

| Electrolyte 3 | weight % |
|---|---|
| $I_2$ | 1.6 |
| mmim I | 35 |
| guaSCN | 0.7 |
| NBB | 2.7 |
| bmpl TCB | 60 |
| total | 100 |

| Electrolyte 4 | weight % |
|---|---|
| $I_2$ | 1.6 |
| mmim I | 35 |
| guaSCN | 0.7 |
| NBB | 2.7 |
| bmpl [$(CH)_3BF(CN)_2$] | 60 |
| total | 100 |

| Electrolyte 5 | weight % |
|---|---|
| $I_2$ | 1.6 |
| mmim I | 35 |
| guaSCN | 0.7 |
| NBB | 2.7 |
| emim [$(CH_3)B(CN)_3$] | 60 |
| total | 100 |

The Electrolytes 1 to 5 are measured using two different dyes (Z907 and D205) at 10° C. and 25° C.

The above cited compounds are commercially available or are synthesized according to known literature methods.

The dye sensitized solar cells are fabricated as disclosed in U.S. Pat. No. 5,728,487 or WO 2007/093961:

A double-layer, mesoporous $TiO_2$ electrode was prepared as disclosed in Wang P et al., J. Phys. Chem. B 2003, 107, 14336, in particular page 14337, in order to obtain a photo-anode consisting of a double layer structure. To prepare a transparent nanoporous $TiO_2$ electrode, a screen printing paste containing terpineol solvent and nanoparticulate $TiO_2$ of anatase phase with 20 nm diameter was deposited on a transparent conductive substrate to 5 mm×5 mm squared shape by using a hand printer. The paste was dried for 10 minutes at 120 degrees Celsius. Another screen printing paste containing $TiO_2$ with 400 nm diameter was then deposited on top of the nanoporous layer to prepare an opaque layer. The double layer film was then sintered at 500 degrees Celsius for an hour with the result of an underlying transparent layer (7 microns thick) and a top opaque layer (4 microns thick). After sintering, the electrode was immersed in 40 mM aqueous solution of $TiCl_4$ (Merck) for 30 minutes at 70 degrees Celsius and then rinsed with pure water sufficiently. Thus $TiCl_4$-treated electrode was dried at 500 degrees Celsius for 30 minutes just before dye sensitization. The electrode was dipped into a 0.3 mM Z907 dye solution of acetonitrile (Merck HPLC grade) and tert-butyl alcohol (Merck), v:v=1:1 for 60 hours at 19 degrees Celsius. The counter electrode was prepared with thermal pyrolysis method as disclosed in the reference above. A droplet of 5 mM solution of platinic acid (Merck) was casted at 8 µl/cm2 and dried on a conductive substrate. The dye sensitized solar cell was assembled by using 30 micron thick Bynel (DuPont, USA) hot-melt film to seal up by heating. The internal space was filled with each of the electrolyte formulations as described above to produce the corresponding devices.

The dye Z907 is an amphiphilic ruthenium sensitizer Ru(2,2'-bipyridine 4,4'-dicarboxylic acid) (4,4'-dinonyl-2,2'-bipyridine)$(NCS)_2$ or synonymously [Ru(H2dcbpy)(dnbpy)$(NCS)_2$].

The indolin dye D205 is described before.

In order to obtain accurate light intensity level, Air Mass 1.5 Global (AM 1.5G) simulated sunlight is calibrated spectrally according to Seigo Ito et al, "Calibration of solar simulator for evaluation of dye-sensitized solar cells", Solar Energy Materials & Solar Cells, 82, 2004, 421.

The measurements of photocurrent-voltage curves are carried out under Air Mass 1.5 simulated sunlight (AM 1.5) with temperature control for devices fabricated as described above containing electrolytes 1 to 4 placed on a black plate chilled down to 25° C. under 1 Sun illumination. A photomask of 4 mm×4 mm is placed on top of the devices to define the light projection area. The cell gap is around 20 micron.

Energy conversion efficiency is generally the ratio between the useful output of an energy conversion machine and the input of light radiation, in energy terms, determined by using adjustable resistant load to optimize the electric power output.

Table 1 summarises the results of the measurements of the above cited electrolyte formulations at 10° C.:

| Dye | electrolyte | 1* | 3* | 5 | 2 | 4 |
|---|---|---|---|---|---|---|
| Z907 | $J_{SC}$ (mA/cm2) | 8.26 | 5.57 | 9.90 | 10.45 | 8.51 |
| | $V_{OC}$ (V) | 0.74 | 0.73 | 0.72 | 0.69 | 0.72 |
| | FF | 0.65 | 0.59 | 0.57 | 0.66 | 0.40 |

-continued

| Dye | electrolyte | 1* | 3* | 5 | 2 | 4 |
|---|---|---|---|---|---|---|
|  | η(%) | 3.94 | 2.38 | 4.04 | 4.70 | 2.48 |
| D205 | $J_{SC}$ (mA/cm2) | 10.94 | 10.36 | 11.87 | 11.85 | 11.40 |
|  | $V_{OC}$(V) | 0.73 | 0.75 | 0.74 | 0.74 | 0.72 |
|  | FF | 0.67 | 0.67 | 0.70 | 0.73 | 0.61 |
|  | η (%) | 5.21 | 5.19 | 6.10 | 6.12 | 5.05 |

Table 2 summarises the results of the measurements of the above cited electrolyte formulations at 25° C.:

| Dye | electrolyte | 1* | 3* | 5 | 2 | 4 |
|---|---|---|---|---|---|---|
| Z907 | $J_{SC}$ (mA/cm2) | 10.45 | 7.57 | 10.27 | 10.47 | 9.14 |
|  | $V_{OC}$(V) | 0.69 | 0.68 | 0.70 | 0.66 | 0.70 |
|  | FF | 0.70 | 0.62 | 0.59 | 0.68 | 0.47 |
|  | η (%) | 4.98 | 3.20 | 4.18 | 4.72 | 2.99 |
| D205 | $J_{SC}$ (mA/cm2) | 11.73 | 10.17 | 11.63 | 12.17 | 11.42 |
|  | $V_{OC}$(V) | 0.70 | 0.73 | 0.71 | 0.70 | 0.70 |
|  | FF | 0.70 | 0.65 | 0.69 | 0.70 | 0.63 |
|  | η (%) | 5.74 | 4.83 | 5.62 | 5.95 | 5.00 |

*not according to the invention
$J_{SC}$ = short circuit current
$V_{OC}$ = open circuit voltage
FF = fill factor
η = power conversion efficiency Table 1 and 2 document that electrolytes comprising methylfluorodicyanoborate as anion perform better or equal than electrolytes comprising TCB as anion if the same cation is used particularly at lower temperature like 10 degrees Celsius due to aforementioned lower negative temperature coefficient of viscosity.

Example B

The following electrolyte formulations are synthesized to demonstrate the application of electrolyte formulations according to the invention relative to electrolyte formulations of the prior art containing 1-butyl-1-methylpyrrolidinium TCB and N-butyl-pyridinium TCB in dye sensitized solar cells.

The electrolyte formulations are prepared through mixing of one or more of 1,3-dimethylimidazolium iodide (mmimI), iodine, N-butylbenzimidazole (NBB) and guanidinium thiocyanate (guaSCN) and the corresponding ionic liquid in weight % as listed below.

| Electrolyte 6 | weight % |
|---|---|
| $I_2$ | 1.3 |
| mmim I | 35 |
| guaSCN | 0.7 |
| NBB | 3.0 |
| Triethylsulfonium methyltricyanoborate | 60 |
| total | 100 |

| Electrolyte 7 | weight % |
|---|---|
| $I_2$ | 1.3 |
| mmim I | 35 |
| guaSCN | 0.7 |
| NBB | 3.0 |
| bmpl diethyldicyanoborate | 60 |
| total | 100 |

| Electrolyte 8* | weight % |
|---|---|
| $I_2$ | 1.3 |
| mmim I | 35 |
| guaSCN | 0.7 |
| NBB | 3.0 |
| bmpl TCB | 60 |
| total | 100 |

| Electrolyte 9 | weight % |
|---|---|
| $I_2$ | 1.3 |
| mmim I | 35 |
| guaSCN | 0.7 |
| NBB | 3.0 |
| emim n-butyltricyanoborate | 60 |
| total | 100 |

| Electrolyte 10 | weight % |
|---|---|
| $I_2$ | 1.3 |
| mmim I | 35 |
| guaSCN | 0.7 |
| NBB | 3.0 |
| bmim diethyldicyanoborate | 60 |
| total | 100 |

| Electrolyte 11 | weight % |
|---|---|
| $I_2$ | 1.3 |
| mmim I | 35 |
| guaSCN | 0.7 |
| NBB | 3.0 |
| BPYR diethyldicyanoborate | 60 |
| total | 100 |

| Electrolyte 12* | weight % |
|---|---|
| $I_2$ | 1.3 |
| mmim I | 35 |
| guaSCN | 0.7 |
| NBB | 3.0 |
| BPYR TCB | 60 |
| total | 100 |

The electrolytes marked with * are not according to the invention.

The Electrolytes 6 to 12 are measured using 0.3 mM Z907 solution at 25° C.

The above cited compounds are commercially available or are synthesized according to known literature methods.

The dye sensitized solar cells are fabricated as disclosed in Example A and the measurements are done as disclosed in Example A.

Table 3 summarises the results of the measurements of the above cited electrolyte formulations at 25° C.:

| electrolyte | 6 | 7 | 8* | 9 | 10 |
|---|---|---|---|---|---|
| $J_{SC}$ (mA/cm2) | 12.27 | 11.85 | 12.24 | 6.58 | 11.24 |
| $V_{OC}$ (V) | 0.67 | 0.72 | 0.72 | 0.70 | 0.77 |
| FF | 0.68 | 0.69 | 0.68 | 0.69 | 0.72 |
| η (%) | 5.60 | 5.92 | 5.98 | 3.21 | 6.15 |

| electrolyte | 11 | 12* |
|---|---|---|
| $J_{SC}$ (mA/cm2) | 11.06 | 10.21 |
| $V_{OC}$ (V) | 0.76 | 0.74 |
| FF | 0.73 | 0.69 |
| η (%) | 6.12 | 5.20 |

*not according to the invention
$J_{SC}$ = short circuit current
$V_{OC}$ = open circuit voltage
FF = fill factor
η = power conversion efficiency Table 3 documents that electrolytes comprising diethyldicyanoborate as anion perform better or equal than electrolytes comprising TCB as anion if the same cation or similar heterocyclic cations are used.

The invention claimed is:

1. A compound of formula I $$[Kt]^{z+}z[(R^1)_{4-x-y-v}B(CN)_x(NC)_yF_v]^-$$  I in which
R¹ in each case independently denotes a straight-chain or branched alkyl group having 1 to 20 C atoms, which optionally contains at least one Cl, Br or I atom, at least one CN group and/or one or more oxygen or sulphur atoms, a straight-chain or branched alkenyl group having 2 to 20 C atoms having one or more double bonds, which optionally contains at least one Cl, Br or I atom and/or one or more oxygen or sulphur atoms, a straight-chain or branched alkynyl group having 1 to 20 C atoms having one or more triple bonds, which optionally contains at least one Cl, Br or I atom and/or one or more oxygen or sulphur atoms and optionally may have a double bond, or unsubstituted phenyl,
z is 1, 2, 3 or 4,
x is 1, 2 or 3,
y is 0, 1 or 2,
v is 0, 1 or 2,
the sum of x+y+v is 2 or 3,
$Kt^{z+}$ denotes an inorganic cation selected from $NO^+$, $H^+$, $Li^+$, $Na^+$, $K^+$, $Rb^+$, $Cs^+$, $Mg^{2+}$, $Cu^+$, $Cu^{2+}$, $Zn^{2+}$, $Ag^+$, $Ca^{2+}$, $Y^{+3}$, $Yb^{+3}$, $La^{+3}$, $Sc^{+3}$, $Ce^{+3}$, $Nd^{+3}$, $Tb^{+3}$, $Sm^{+3}$ or complex (ligands containing) metal cations which include rare-earths, transitions or noble metals or an organic cation selected from
   (a) a tritylium cation, in which the phenyl groups may be substituted by straight-chain or branched alkyl groups having 1 to 20 C atoms, straight-chain or branched alkenyl having 2 to 20 C atoms and one or more double bonds or straight-chain or branched alkynyl having 2 to 20 C atoms and one or more triple bonds,
   (b) an oxonium cation of formula (1) or a sulfonium cation of formula (2))

$[(R^o)_3O]^+$ (1)

$[(R^o)_3S]^+$ (2), where $R^o$ each, independently of one another, denotes a straight-chain or branched alkyl group having 1-8 C atoms, non-substituted phenyl or phenyl which is substituted by $R^{1*}$, OR', N(R')₂, CN or halogen and in case of sulfonium cations of formula (2) additionally denotes each independently (R''')₂N,
R' is independently of each other H, non-fluorinated, partially fluorinated or perfluorinated straight-chain or branched $C_1$- to $C_{18}$-alkyl, saturated $C_3$- to $C_7$-cycloalkyl, non-substituted or substituted phenyl,
$R^{1*}$ is independently of each other non-fluorinated, partially fluorinated or perfluorinated straight-chain or branched $C_1$- to $C_{18}$-alkyl, saturated $C_3$- to $C_7$-cycloalkyl, non-substituted or substituted phenyl, and
R''' is independently of each other straight-chain or branched $C_1$ to $C_6$ alkyl,
(c) an ammonium cation, which conforms to the formula (3)

$[NR_4]^+$ (3), where R in each case, independently of one another, denotes H, OR', N(R')₂, with the proviso that a maximum of one R in formula (3) is OR' or N(R')₂,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, saturated, partially or fully unsaturated cycloalkyl having 3-7 C atoms, which may be substituted by straight-chain or branched alkyl groups having 1-6 C atoms,
where one or two R may be fully substituted by halogens, and one or more of the substituents R may be partially substituted by halogens, and/or by —OH, —OR', —CN, —N(R')₂, —C(O)OH, —C(O)OR', —C(O)R', —C(O)N(R')₂, —SO₂N(R')₂, —C(O)X, —SO₂OH, —SO₂X, —NO₂, —SR', —S(O)R', or —SO₂R' and where one or two non-adjacent carbon atoms in R which are not in the α-position may each be replaced by —O—, —S—, —S(O)—, —SO₂—, —SO₂O—, —C(O)—, —C(O)O—, —N⁺(R')₂—, —P(O)R'O—, —C(O)NR'—, —SO₂NR'—, —OP(O)R'O—, —P(O)(N(R')₂)NR'—, —P(R')₂=N— or —P(O)R'—,
R' in each case independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl, and
X in each case, independently of one another, is halogen;
(d) a phosphonium cation, which conforms to the formula (4)

$[P(R^2)_4]^+$ (4), where $R^2$ in each case, independently of one another, denotes H, OR' or N(R')₂,
straight-chain or branched alkyl having 1-20 C atoms, straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two $R^2$ may be fully substituted by halogens, and one or more of the substituents $R^2$ may be partially substituted by halogens, and/or by —OH, —OR', —CN, —N(R')$_2$, —C(O)OH, —C(O)OR', —C(O)R', —C(O)N(R')$_2$, —SO$_2$N(R')$_2$, —C(O)X, —SO$_2$OH, —SO$_2$X, —NO$_2$, —SR', —S(O)R', or —SO$_2$R', and where one or two non-adjacent carbon atoms in $R^2$ which are not in the α-position may each be replaced by —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—,
R' in each case independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl, and
X in each case independently is halogen,
(e) a uronium cation, which conforms to the formula (5)

[C(NR$^3$R$^4$)(OR$^5$)(NR$^6$R$^7$)]$^+$ (5), where $R^3$ to $R^7$ each, independently of one another, denote H, where H is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two of the substituents $R^3$ to $R^7$ may be fully substituted by halogens, and one or more of the substituents $R^3$ to $R^7$ may be partially substituted by halogens, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', or —NO$_2$, and where one or two non-adjacent carbon atoms in $R^3$ to $R^7$ which are not in the α-position may each be replaced by —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—,
R' in each case independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl, and
X in each case independently is halogen, (f) a thiouronium cation, which conforms to the formula (6)

[C(NR$^3$R$^4$)(SR$^5$)(NR$^6$R$^7$)]$^+$ (6), where $R^3$ to $R^7$ each, independently of one another, denote H, where H is excluded for $R^5$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two of the substituents $R^3$ to $R^7$ may be fully substituted by halogens, and one or more of the substituents $R^3$ to $R^7$ may be partially substituted by halogens, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', or —NO$_2$, and where one or two non-adjacent carbon atoms in $R^3$ to $R^7$ which are not in the α-position may each be replaced by —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—,
R' in each case independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl, and
X in each case independently is halogen, (g) a guanidinium cation, which conforms to the formula (7)

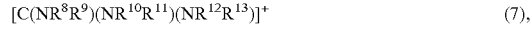

[C(NR$^8$R$^9$)(NR$^{10}$R$^{11}$)(NR$^{12}$R$^{13}$)]$^+$ (7), where $R^8$ to $R^{13}$ each, independently of one another, denote H, —CN, N(R')$_2$, —OR',
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by straight-chain or branched alkyl groups having 1-6 C atoms,
where one or two of the substituents $R^8$ to $R^{13}$ may be fully substituted by halogens and one or more of the substituents $R^8$ to $R^{13}$ may be partially substituted by halogens, and/or by —OH, —OR', —N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', or —NO$_2$, and where one or two non-adjacent carbon atoms in $R^8$ to $R^{13}$ which are not in the α-position may each be replaced by —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—, where
R' in each case independently is H, non-fluorinated, partially fluorinated or perfluorinated straight-chain or branched $C_1$- to $C_{18}$-alkyl, saturated $C_3$- to $C_7$-cycloalkyl, non-substituted or substituted phenyl, and X in each case independently is halogen;

(h) a heterocyclic cation which conforms to the formula (8)

$$[HetN]^{z+} \quad (8)$$

where $HetN^{z+}$ denotes a heterocyclic cation selected from

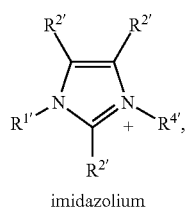
imidazolium

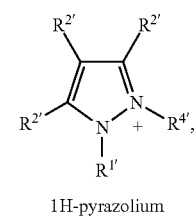
1H-pyrazolium

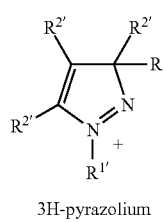
3H-pyrazolium

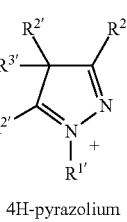
4H-pyrazolium 1-pyrazolinium

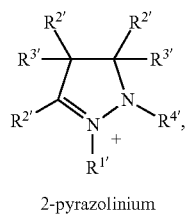
2-pyrazolinium

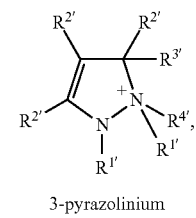
3-pyrazolinium

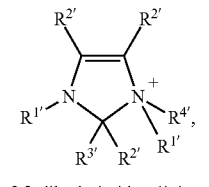
2,3-dihydroimidazolinium

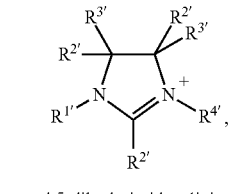
4,5-dihydroimidazolinium

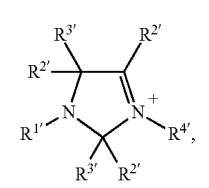
2,5-dihydroimidazolinium

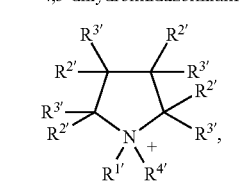
pyrrolidinium

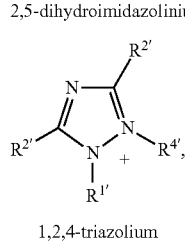
1,2,4-triazolium    1,2,4-triazolium    1,2,3-triazolium

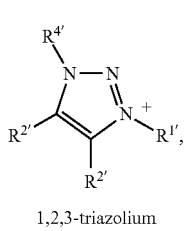
1,2,3-triazolium

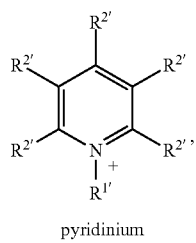
pyridinium

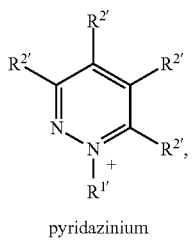
pyridazinium

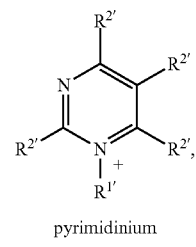
pyrimidinium

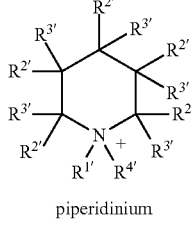
piperidinium

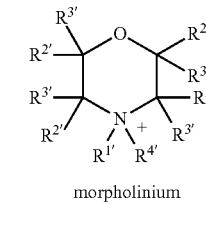
morpholinium

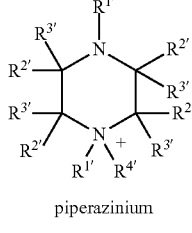
piperazinium

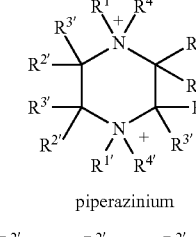
piperazinium

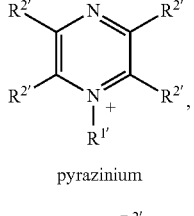
pyrazinium thiazolium    oxazolium

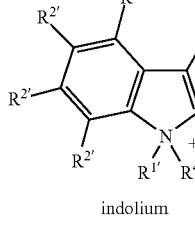
indolium

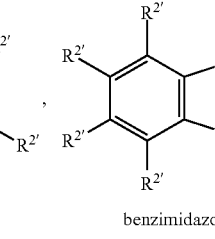
benzimidazolium

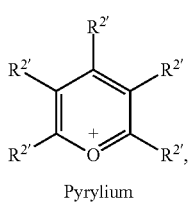
Pyrylium

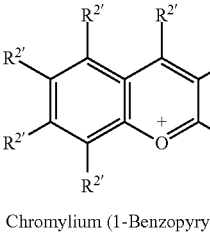
and

Chromylium (1-Benzopyrylium)

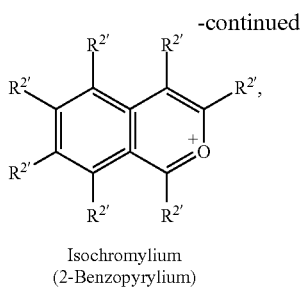

Isochromylium
(2-Benzopyrylium)

where the substituents $R^{1\prime}$ to $R^{4\prime}$ each, independently of one another, denote H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, and $R^{2\prime}$ each, independently of one another, additionally denotes F, Cl, Br, I, —CN, —OR', —N(R')$_2$, —P(O)(R')$_2$, —P(O)(OR')$_2$, —P(O)(N(R')$_2$)$_2$, —C(O)R', —C(O)OR', —C(O)X, —C(O)N(R')$_2$, —SO$_2$N(R')$_2$, —SO$_2$OH, —SO$_2$X, —SR', —S(O)R', —SO$_2$R' or NO$_2$, with the proviso that $R^{1\prime}$, $R^{3\prime}$, $R^{4\prime}$ are in this case independently of each other H and/or a straight-chain or branched alkyl having 1-20 C atoms, straight-chain or branched alkenyl having 2-20 C atoms and one or more double bonds, where one to three substituents $R^{1\prime}$ to $R^{4\prime}$ may be fully substituted by halogens, and one or more substituents $R^{1\prime}$ to $R^{4\prime}$ may be partially substituted by halogens, and/or by —OH, —OR', N(R')$_2$, —CN, —C(O)OH, —C(O)OR', —C(O)R', —C(O)N(R')$_2$, —SO$_2$N(R')$_2$, —C(O)X, —SO$_2$OH, —SO$_2$X, —SR', —S(O)R', —SO$_2$R', or —NO$_2$, but where $R^{1\prime}$ and $R^{4\prime}$ cannot simultaneously be fully substituted by halogens, and where, in the substituents $R^{1\prime}$ to $R^{4\prime}$, one or two non-adjacent carbon atoms which are not bonded to the heteroatom may each be replaced by —O—, —S—, —S(O)—, —SO$_2$—, —SO$_2$O—, —C(O)—, —C(O)O—, —N$^+$(R')$_2$—, —P(O)R'O—, —C(O)NR'—, —SO$_2$NR'—, —OP(O)R'O—, —P(O)(N(R')$_2$)NR'—, —P(R')$_2$=N— or —P(O)R'—, R' in each case independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl, and X in each case independently is halogen, or
(i) a iodonium cation which conforms to the formula (9)

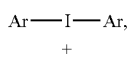

where the aryl group Ar denotes each independently of each other aryl with 6 to 30 C atoms which is non-substituted or substituted with at least a straight-chain or branched alkyl group having 1 to 20 C atoms, a straight-chain or branched alkenyl group having 2 to 20 C atoms and one or more double bonds, a straight-chain or branched alkynyl group having 2 to 20 C atoms and one or more triple bonds, R$^{1*}$, NO$_2$, SR', N(R')$_2$, CN and/or halogen, and R' each independently is H, non-fluorinated, partially fluorinated or perfluorinated straight-chain or branched C$_1$- to C$_{18}$-alkyl, saturated C$_3$- to C$_7$-cycloalkyl, non-substituted or substituted phenyl, R$^{1*}$ each independently is non-fluorinated, partially fluorinated or perfluorinated straight-chain or branched C$_1$- to C$_{18}$-alkyl, saturated C$_3$- to C$_7$-cycloalkyl, non-substituted or substituted phenyl, and halogen is F, Cl, Br or I, with the proviso that potassium (18-crone-6) tricyano-n-octylborate and tetraethylammonium phenyl-tricyanoborate are excluded.

2. A compound according to claim 1, wherein R$^1$ in each case independently is a straight-chain or branched alkyl group having 1 to 4 C atoms, which optionally contains at least one Br atom or at least one CN group or at least one oxygen atom or a straight-chain or branched alkenyl having 2 to 4 C atoms.

3. A process for the preparation of a compound according to claim 1 in which [Kt]$^{z+}$ is an alkali metal cation, z denotes 1 and the sum of x+y+v denotes 3, which denotes a compound of formula I-1, $$[Me]^+[(R^1)_{4-x-y-z}B(CN)_x(NC)_yF_v]^- \qquad \text{I-1,}$$

in which [Me]$^+$ denotes an alkali metal cation and R$^1$, x, y and v have the meanings according to claim 1, said process comprising:
reacting a compound of formula II $$[Me]^+[(R^1)BF_3]^- \qquad \text{II}$$

in which [Me$^1$]$^+$ denotes an alkali metal cation and R$^1$ has a meaning according to claim 1,
with a trialkylsilylcyanide, in which the alkyl groups are each independently of one another straight-chain or branched alkyl having 1 to 8 C atoms.

4. A process for the preparation of a compound according to claim 1 in which [Kt]$^{z+}$ is an organic cation and the sum of x+y+v denotes 3, said process comprising:
reacting a compound of formula III $$[Kt]^{z+}[(R^1)BF_3]^- \qquad \text{III}$$

in which [Kt]$^{z+}$ denotes the organic cation and R$^1$ has a meaning according to claim 1,
with a trialkylsilylcyanide, in which the alkyl groups are each independently of one another straight-chain or branched alkyl having 1 to 8 C atoms.

5. A process for the preparation of a compound according to claim 1 in which [Kt]$^{z+}$ is alkali metal cation, z denotes 1 and the sum of x+y+v denotes 2, said process comprising:
reacting a compound of formula IV $$(R^1)_2BOCH_3 \qquad \text{IV}$$

in which R$^1$ has a meaning according to claim 1,
with a trialkylsilylcyanide in the presence of an alkali metal fluoride, wherein the alkyl groups within the trialkylsilylcyanide are each independently of one another straight-chain or branched alkyl having 1 to 8 C atoms.

6. A process for the preparation of a compound according to claim 1 in which [Kt]$^{z+}$ is another cation than the used alkali metal cation in the starting material in a salt-exchange reaction, said process comprising:

reacting an alkali metal salt of formula I-1

$$[Me]^+[(R^1)_{4-x-y-v}B(CN)_x(NC)_yF_v]^-  \qquad I\text{-}1$$

in which [Me]$^+$ is an alkali metal cation and R$^1$, x, y, v and the sum of x+y+v have the meanings according to claim 1, with a compound of formula V $$KtA \qquad V,$$

in which

Kt has a meaning of an organic cation or an inorganic cation other than the alkali metal cation of the compound of formula I-1, and A denotes F$^-$, Cl$^-$, Br$^-$, I$^-$, OH$^-$, [HF$_2$]$^-$, [CN]$^-$, [SCN]$^-$, [R$_1$COO]$^-$, [R$_1$OC(O)O]$^-$, [R$_1$SO$_3$]$^-$, [R$_2$COO]$^-$, [R$_2$SO$_3$]$^-$, [R$_1$OSO$_3$]$^-$, [BF$_4$]$^-$, [PF$_6$]$^-$, [HSO$_4$]$^{1-}$, [NO$_3$]$^-$, [(R$_2$)$_2$P(O)O]$^-$, [R$_2$P(O)O$_2$]$^{2-}$, [(R$_1$O)$_2$P(O)O]$^-$, [(R$_1$O)P(O)O$_2$]$^{2-}$, [(R$_1$O)R$_1$P(O)O]$^-$, tosylate, malonate which may be substituted by straight-chain or branched alkyl groups having 1 to 4 C atoms, [HOCO$_2$]$^-$ or [CO$_3$]$^{2-}$ (merely for the synthesis of other compounds of formula I-1 having another alkali metal cation than the starting material), R$_1$ is each independently of another a straight-chain or branched alkyl group having 1 to 12 C atoms, and R$_2$ is each independently of one another a straight-chain or branched perfluorinated alkyl group having 1 to 12 C atoms and where electroneutrality should be taken into consideration in the formula of the salt KtA.

7. An electrolyte formulation comprising at least one compound according to claim 1.

8. An electrochemical and/or optoelectronic device comprising an electrolyte formulation according to claim 7.

9. A catalyst, conducting salt, electrolyte, surfactant, phase-transfer catalyst, entrainer, extractant, antistatic additive, plasticizer, heat-transfer-medium, modifier for membranes and textile materials, lubricant, or hydraulic fluid comprising a compound according to claim 1 in which [Kt]$^{z+}$ is an organic cation or H$^+$ and z is 1, 2, 3 or 4.

10. An electrolyte according to claim 7, in which [Kt]$^{z+}$ is Li$^+$ as conducting salt and/or component of electrolytes.

11. A catalyst, conducting salt, electrolyte, surfactant, phase-transfer catalyst, or antistatic additive comprising a compound according to claim 1 in which [Kt]$^{z+}$ is an inorganic cation.

12. A process according to claim 6, in which [Kt]$^{z+}$ is an organic cation and z is 1, 2, 3 or 4.

13. A cationic polymerization initiator, photo-polymerization initiator or photo-acid generator comprising a compound according to claim 1 in which [Kt]$^{z+}$ is a cation of formula (2), (5), (6), (9), tritylium, pyrylium, 1-benzopyrylium or 2-benzopyrylium.

14. A curable composition comprising at least one compound according to claim 1 with cations of formula (2), (5), (6), (9), tritylium, pyrylium, 1-benzopyrylium or 2-benzopyrylium, and at least one polymerizable compound.

15. A compound according to claim 1, wherein R$^1$ in each case independently denotes a straight-chain or branched alkyl group having 1 to 20 C atoms, which optionally contains at least one Cl, Br or I atom, at least one CN group and/or one or more oxygen or sulphur atoms, a straight-chain or branched alkenyl group having 2 to 20 C atoms having one or more double bonds, which optionally contains at least one Cl, Br or I atom and/or one or more oxygen or sulphur atoms, or a straight-chain or branched alkinyl group having 1 to 20 C atoms having one or more triple bonds, which optionally contains at least one Cl, Br or I atom and/or one or more oxygen or sulphur atoms and optionally may have a double bond.

16. A compound according to claim 1, wherein said compound is potassium methyldicyanofluoroborate, potassium methyltricyanoborate, potassium methyldicyanoisocyanoborate, potassium n-butyldicyanoisocyanoborate, potassium n-butyltricyanoborate, 1-ethyl-3-methylimidazolium n-butyltricyanoborate, potassium allyltricyanoborate, 1-ethyl-3-methylimidazolium methyldicyanofluoroborate, 1-ethyl-3-methylimiazolium methylcyanodifluoroborate, 1-ethyl-3-methylimidazolium tricyano-methylborate, 1-butyl-3-methylimidazolium methyltricyanoborate, triethylsulfonium methyltricyanoborate, methyldiphenylsulfonium methyltricyanoborate, triphenylsulfonium methyltricyanoborate, diphenyliodonium methyltricyanoborate, 2,4,6-triphenylpyrylium methyltricyanoborate, triphenylcarbenium methyltricyanoborate, 1-ethyl-3-methyl-imidazolium vinyltricyanoborate, butylmethylpyrrolidinium tricyanomethylborate, tetrabutylammonium tricyanomethylborate, tetraphenylphosphonium diethyldicyanoborate, 1-ethyl-3-methylimidazolium vinyldicyano-isocyanoborate, potassium methyldicyano-fluoroborate, 1-ethyl-3-methylimidazolium methyldicyanofluoroborate, 1-butyl-1-methylpyrrolidinium methyldicyanofluoroborate, potassium cyanomethyldicyanofluoroborate, 1-ethyl-3-methylimidazolium cyanomethyldicyanofluoroborate, 1-ethyl-3-methylimidazolium cyanomethylcyanodifluoroborate, potassium diethyldicyanoborate, 1-butyl-3-methylimidazolium diethyldicyanoborate, N-butyl-N-methylpyrrolidinium diethyldicyanoborate, or N-butylpyridinium diethyldicyanoborate.

17. A compound according to claim 1, wherein said compound is of formula IA:

$$[Kt]^{z+}z[(R^1)B(CN)_2F]^- \qquad IA,$$

wherein [Kt]$^{z+}$, z and R$^1$ have the meanings defined in claim 1.

18. A compound according to claim 1, wherein said compound is of formula IB:

$$[Kt]z+z[(R^1)B(CN)_3]^- \qquad IB,$$

wherein [Kt]$^{z+}$, z and R$^1$ have the meanings defined in claim 1.

19. A compound according to claim 1, wherein said compound is of formula IC:

$$[Kt]^{z+}z[(R^1)B(CN)_2(NC)]^- \qquad IC,$$

wherein [Kt]$^{z+}$, z and R$^1$ have the meanings defined in claim 1.

20. A compound according to claim 1, wherein said compound is of formula ID:

$$[Kt]^{z+}z[(R^1)B(CN)F_2]^- \qquad ID,$$

wherein [Kt]$^{z+}$, z and R$^1$ have the meanings defined in claim 1.

21. A compound according to claim 1, wherein said compound is of formula IE:

$$[Kt]z+z[(R^1)_2B(CN)_2]^- \qquad \text{IE,}$$

wherein [Kt]$^{z+}$, z and R$^1$ have the meanings defined in claim 1.

22. A compound according to claim 1, wherein said cation is of formula (2) and is selected from diethyl-methylsulfonium, triethylsulfonium, triphenylsulfonium, diphenyltolylsulfonium, diphenylethylsulfonium, diphenyl-2,2,2-trifluorethyl sulfonium, diphenyl-2-ethoxy-ethylsulfonium, diphenyl-2-chlorethylsulfonium, diphenyl-3-brompropylsulfonium, diphenyl-3-chlorpropylsulfonium, diphenyl-3-cyanopropylsulfonium, diphenylallylsulfonium, diphenyl-4-pentenylsulfonium, diphenylpropargylsulfonium, diphenylbenzylsulfonium, diphenyl(p-cyanobenzyl)sulfonium, diphenyl(p-methylbenzyl)sulfonium, diphenyl(p-phenylthiobenzyl)sulfonium, diphenyl(3,3-dicyano-2-phenyl-2-propenyl)sulfonium, diphenyl(p-methylphenacyl)sulfonium, diphenyl(ethylcarboxy)methylsulfonium, diphenyl(n-octyl)sulfonium, diphenyl(n-octadecyl)sulfonium, diphenyl(ω-carboxytridecyl)sulfonium, diphenyl(3-oxypropyl)sulfonium, diphenyl(ω-carboxydodecyl)sulfonium, dihexylphenylsulfonium, ditolylphenylsulfonium, tritolylsulfonium, m- or p-(tert-butyl)phenyl-diphenylsulfonium, m- or p-methoxyphenyl-diphenylsulfonium, m- or p-CN-phenyl-diphenylsulfonium, m- or p-C$_6$H$_{13}$S-phenyl-diphenylsulfonium, m- or p-C$_6$H$_5$S-phenyl-diphenylsulfonium, Tri(p-methoxyphenyl)sulfonium, tri[4-(4-acetyl-phenylsulfanyl)phenyl]sulfonium, or tri(4-tert.-butylphenyl)sulfonium.

23. A compound according to claim 1, wherein said cation is of formula (3) and R in each case is independently selected from methyl, ethyl, isopropyl, propyl, n-butyl, sec-butyl, pentyl, hexyl, octyl, decyl or tetradecyl.

24. A compound according to claim 1, wherein said cation is of formula (4) and R$^2$ in each case is independently selected from methyl, ethyl, isopropyl, propyl, n-butyl, sec-butyl, pentyl, hexyl, octyl, decyl or tetradecyl.

25. A compound according to claim 1, wherein said cation is of formula (8) and is selected from:

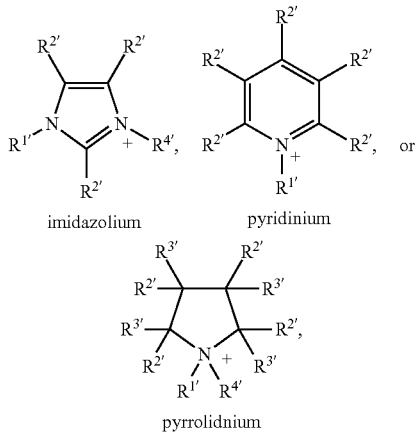

where the substituents R$^{1'}$ to R$^{4'}$ each, independently of one another, have the meanings indicated in claim 1.

26. A compound according to claim 1, wherein said cation is selected from 1-butyl-1-methylpyrrolidinium, 1-ethyl-3-methylimidazolium, 1-ethyl-2,3-dimethylimidazolium, 1-(2-methoxyethyl)-3-methylimidazolium, 1-butyl-3-methylimidazolium, tributyl-methylammonium, tetra-n-butylammonium, tributyl-methylphosphonium, tetraphenylphosphonium, diethyl-methylsulfonium, S-ethyl-N,N,N',N'-tetramethylisothiouronium, 1-allyl-3-methylimidazolium, 1-allyl-2,3-dimethylimidazolium, 1-cyanomethyl-3-methylimidazolium, 1-methyl-3-propinylimidazlium, 1,1-dimethylpyrrolidinium, or trimethylsulfonium.

\* \* \* \* \*